United States Patent
Park et al.

(10) Patent No.: US 9,359,592 B2
(45) Date of Patent: *Jun. 7, 2016

(54) METHOD FOR DIFFERENTIATION INTO RETINAL CELLS FROM STEM CELLS

(75) Inventors: Sung Sup Park, Seoul (KR); Ji Yeon Kim, Seoul (KR)

(73) Assignee: SNU R&DB Foundation, Seoul (KR)

( * ) Notice: Subject to any disclaimer, the term of this patent is extended or adjusted under 35 U.S.C. 154(b) by 562 days.

This patent is subject to a terminal disclaimer.

(21) Appl. No.: 13/055,709

(22) PCT Filed: Oct. 6, 2010

(86) PCT No.: PCT/KR2010/006832
§ 371 (c)(1),
(2), (4) Date: Jan. 24, 2011

(87) PCT Pub. No.: WO2011/043591
PCT Pub. Date: Apr. 14, 2011

(65) Prior Publication Data
US 2011/0223140 A1    Sep. 15, 2011

(30) Foreign Application Priority Data

Oct. 6, 2009   (KR) .................. 10-2009-0094854

(51) Int. Cl.
| | | |
|---|---|---|
| *C12N 5/07* | (2010.01) | |
| *A61P 27/02* | (2006.01) | |
| *C12Q 1/02* | (2006.01) | |
| *A61K 35/44* | (2015.01) | |
| *C12N 5/079* | (2010.01) | |

(52) U.S. Cl.
CPC ........ *C12N 5/0621* (2013.01); *C12N 2501/105* (2013.01); *C12N 2501/155* (2013.01); *C12N 2501/998* (2013.01); *C12N 2506/02* (2013.01); *C12N 2506/45* (2013.01)

(58) Field of Classification Search
None
See application file for complete search history.

(56) References Cited

U.S. PATENT DOCUMENTS 7,541,186 B2    6/2009   Reh et al.

OTHER PUBLICATIONS

Kubo, Fumi; Nakagawa, Shinichi; "Wnt signaling in retinal stem cells and regeneration" Development, Growth & Differentiation, 50, 245-251, 2008.*
D'Amour, et al., "Production of pancreatic hormone-expressing endocrine cells from human embryonic stem cells", Nature Biotechnology, 2006, vol. 24, No. 11, pp. 1392-1401.
Pankratz, et al., "Directed neural differentiation of human embryonic stem cells via an obligated primitive anterior stage", Stem Cells, 2007, vol. 25, pp. 1511-1520.
Barberi, et al., "Derivation of engraftable skeletal myoblasts from human embryonic stem cells", Nature Medicine, 2007, vol. 13, No. 5, pp. 642-648.
Wang, et al., "Endothelial cells derived from human embryonic stem cells form durable blood vessels in vivo", Nature Biotechnoly, 2007, vol. 25, No. 3, pp. 317-318.
Lamba et al., "Efficient generation of retinal progenitor cells from human embryonic stem cells", Proceedings of National Academy of Science, USA, 2006, vol. 203, No. 2, pp. 12769-12774.
Osakada, et al., "Toward the generation of rod and cone photoreceptors from mouse, monkey and human embryonic stem cells", Nature Biotechnology, 2008, vol. 26, pp. 215-224.
Bi, Y., et al., "Stem/progenitor cells: A potential source of retina-specific cells fro retinal repair", Neuroscience Research, Jul. 30, 2009, vol. 65, pp. 215-221.
Erceg, S., et al., "Human embryonic stem cell differentiation toward regional specific neural precursors", Stem Cells, Oct. 9, 2008, vol. 27, pp. 78-87.
International Search Report dated Jun. 16, 2011 of PCT/KR2010/006832 which is the parent application—5 pages.
Ryan and Goss, "The emerging role of the insulin-like growth factor pathway as a therapeutic target in cancer", Oncologist, 2008, vol. 13, No. 1, pp. 16-24.
Yamamoto and Oelgeschlager, "Regulation of bone morphogenetic proteins in early embryonic development", Naturwissenschaften, 2004, vol. 91, pp. 519-534.
Yanagita, "BMP antagonists: Their roles in development and involvement in pathophysiology", Cytokine Growth Factor Reviews, 2005, vol. 16, pp. 309-317.
Bottcher and Niehrs, "Fibroblast growth factor signaling during early vertebrate development", Endocrine Reviews, 2005, vol. 26, No. 1, pp. 63-77.
Logan and Nusse, "The Wnt signaling pathway in development and disease", Annu. Rev. Cell Dev. Biol., 2004, vol. 20, pp. 781-810.
Kawano and Kypta, "Secreted antagonists of the Wnt Signaling pathway", Journal of Cell Science, 2003, vol. 116, pp. 2627-2634.
Piccolo et al., "The head inducer Cerberus is a multifunctional antagonist of Nodal, BMP and Wnt signals", Letters to Nature, 1999, vol. 397, pp. 707-710.
Baumer et al., "Retinal pigmented epithelium determination requires the redundant activities of Pax2 and Pax6", Development, 2003, vol. 130, pp. 2903-2915.
Hirami et al., "Generation of retinal cells from mouse and human induced pluripotent stem cells," Neuroscience Letters 458: 126-131, 2009.

* cited by examiner

*Primary Examiner* — Renee Claytor
*Assistant Examiner* — David Berke-Schlessel

(57) ABSTRACT

Disclosed is a method for inducing stem cells to differentiate into retinal cells at high yield within a short period of time, without gene implantation and co-culture with retinal tissues, by implementing a differentiation process similar to the in vivo embryonic development in chemically defined conditions. Also, retinal cells including the photoreceptor cells and their progenitor cells, and various types of other retinal cells, generated according to the method, are disclosed. A composition comprising the retinal cells and a method are provided for treating retinal degeneration-related diseases. The differentiated photoreceptor cells, when transplanted into degenerated or injured retinas, can be engrafted and fused within the retinas to prevent or cure retinal degeneration.

17 Claims, 22 Drawing Sheets

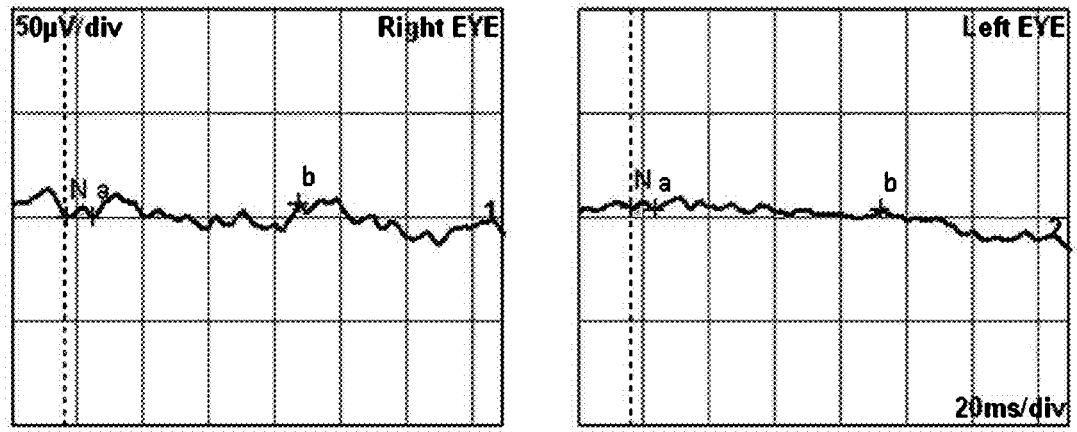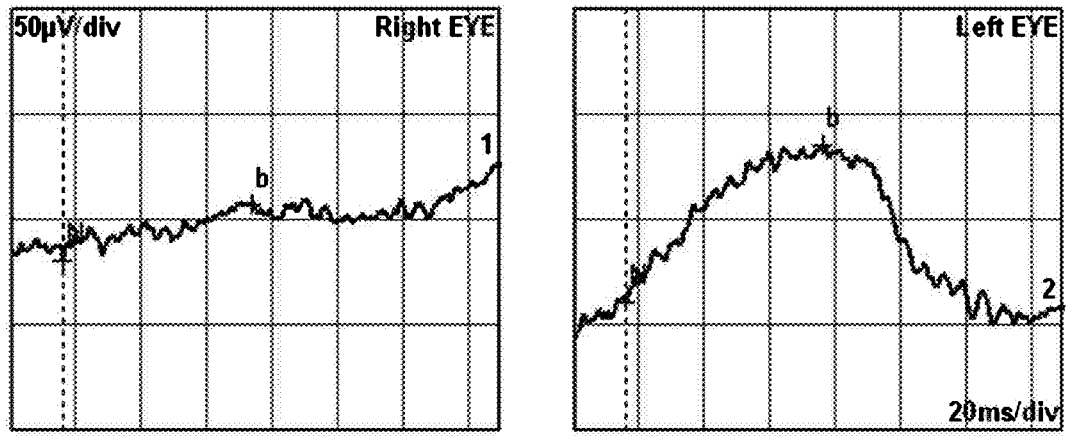
FIG. 18

METHOD FOR DIFFERENTIATION INTO RETINAL CELLS FROM STEM CELLS

CROSS-REFERENCES TO RELATED APPLICATIONS

This application is a U.S. national phase application of International PCT Patent Application No. PCT/KR2010/006832, which was filed on Oct. 6, 2010, which claims priority to Korean Patent Application No. 10-2009-0094854, filed Oct. 6, 2009.

TECHNICAL FIELD

The present invention relates to a method for differentiating stem cells into retinal cells within a short period of time at high yield. More particularly, the present invention relates to a method for differentiating stem cells into neural retinal progenitor cells, photoreceptor cell precursors, photoreceptor cells and other retinal cells, by culturing in different media and time periods specifically adapted to differentiation steps. Also, the present invention is concerned with neural retinal progenitor cells, photoreceptor cell precursors, photoreceptor cells and other retinal cells generated according to the method, a composition for the treatment of retinal degeneration-related diseases, comprising the cells, and a method for the treatment of retinal degeneration-related diseases using the composition.

BACKGROUND ART

Blindness is the medical condition of lacking visual perception for physiological or neurological reasons. As many as tens of millions of people, which accounts for 0.2-0.5% of the population of the world, are affected with blindness, and are suffering from great losses in personal, social and economical respects. Retinal photoreceptor degeneration is one of the more dominant etiologies of blindness, caused innately or by other various factors, including retinal dysplasia, retinal degeneration, aged macular degeneration, diabetic retinopathy, retinitis pigmentosa, congenital retinal dystrophy, Leber congenital amaurosis, retinal detachment, glaucoma, optic neuropathy, and trauma. No drugs have been developed for the fundamental treatment of these diseases thus far. To date, the replacement of dysfunctional photoreceptor cells, the alpha and omega of these retinal diseases, with new ones is regarded as the only promising therapy. Photoreceptor cell implantation is thought to prevent blindness or recover imperfect eyesight by delaying or restraining retinal degeneration, regenerating degenerated retina, and enhancing retinal functions.

Stem cells have become a candidate useful for cell therapy of retinal diseases including bone marrow stem cells (BMSC), cord blood stem cells, amniotic fluid stem cells, fat stem cells, retinal stem cells (RSC), embryonic stem cells (ESC), induced pluripotent stem cells (iPSC) and somatic cell nuclear transfer cells (SCNT).

No significant research results have been yet suggested regarding the differentiation of stem cells into retinal cells (particularly, photoreceptor cells) and cell therapy based thereon. The differentiation of these stem cells into retinal cells might make it possible 1) to guarantee an infinite cell source for efficient cell therapy, 2) to identify the differentiation mechanism from embryonic cells and retinal progenitors into retinal cells, which has remained unclear, 3) to find retina differentiation-related genes and molecules and lesions thereby, 4) to understand the pathogenesis of retinal degenerative diseases, and 5) to develop drugs for preventing retinal degeneration and protecting the retina.

Since the first establishment thereof, human embryonic stem cell lines have been suggested to have the ability to differentiate into various types of cells which are useful for the cellular therapy of various diseases. Human embryonic stem cells appear to have a high potential when it comes to allowing the accurate examination of pathogenetic mechanisms and supplying fresh cells that can substitute for dysfunctional cells in clinical treatment. The production of human ESC derived-retinal photoreceptor cells under a completely identified reproducible condition and the use thereof in transplantation would guarantee a highly potential and effective therapy for retinal photoreceptor cell-related diseases. It has been assumed that human ESC derived-cells will have the same properties and functions as did the cells formed that were formed through a normal differentiation processes. Based on this assumption, differentiation has been induced under circumstances similar to those of the developmental stages to produce pancreatic hormone-expressing endocrine cells (D'Amour, et al., Nat. Biotechnol., 2006; 24: 1392-401), neurons (Pankratz, et al., Stem Cells 2007; 25: 1511-20), muscle cells (Barberi et al., Nat. Med., 2007; 13: 642-8), and vascular endothelial cells (Wang, et al., Nat. Biotechnol., 2007; 25: 317-8). Also, many attempts have been made to differentiate human ESC into photoreceptor cells which may be effectively used to treat retinal diseases, but this ended with failure for most cases.

In fact, differentiation into retinal progenitor cells from human embryonic stem cells is the greatest achievement made thus far in this field, but the differentiation of retinal progenitor cells into photoreceptor cells failed (differentiation rate of less than 0.01%) (Lamba, Proc. Natl. Acad. Sci. USA, 2006; 103: 12769-74). One report held that human embryonic stem cells were successfully induced to differentiate into photoreceptor cells, but the method used therein requires more than 200 days in total for the differentiation, with a differentiation rate of as low as 8%, and thus is impossible to apply to the clinical treatment of blindness (Osakada et al., Nat. Biotechnol., 2008; 26: 215-24).

DISCLOSURE

Technical Problem

Leading to the present invention, intensive and thorough research into the differentiation of human ESC into photoreceptor cells, conducted by the present inventors, resulted in the finding that chemically defined, in vitro conditions for differentiation into photoreceptor cells, similar to in vivo conditions, allow human stem cells to differentiate into photoreceptor cells at high yield within four weeks with neither gene implantation nor co-culturing with retinal tissues. Also, the finally differentiated cells were 260-fold higher in population than the starting human embryonic stem cells, and thus can be applied to clinical transplantation.

Technical Solution

It is therefore an object of the present invention to provide a method for inducing stem cells to differentiate into retinal cells including a multitude of photoreceptor cells and progenitor cells thereof, at high yield within a short period of time, without gene implantation and co-culture with retinal tissues, by implementing a differentiation process similar to the in vivo embryonic development in chemically defined conditions.

It is another object of the present invention to provide photoreceptor cells and their progenitor cells, and retinal cells including them, generated according to the method, which, when transplanted into degenerated or injured retinas, can be engrafted and fused therein.

It is a further object of the present invention to provide a composition for the treatment of retinal degeneration-related diseases, comprising retinal cells including the photoreceptor cells and their progenitor cells and other types of retinal cells.

It is still a further object of the present invention to provide a method for the treatment of retinal degeneration-related diseases, comprising administering the composition to a subject in need thereof.

Advantageous Effects

As described above, stem cells can be differentiated into a multitude of photoreceptor cells at high yield within a short period of time by implementing a differentiation process similar to the in vivo embryonic development and the differentiated photoreceptor cells, when transplanted into degenerated or injured retinas, can be engrafted and fused within the retinas to prevent or cure retinal degeneration. Also, novel genes and molecules involved in retinal differentiation, found by the present invention, can be used to examine the etiology of retinal degeneration-related diseases caused thereby and to develop drugs for preventing retinal degeneration and protecting retinal neurons.

(A) Left. Typical cell floc of hESCs in an undifferentiated state (29 passages; 40× magnification), after being cultured for 5 days from cells of passage number 28. Characterized by a definite separation from adjacent MEF feeder cells. Having plain surface and uniform morphology.

(A) Right. Floating aggregates (40× magnification), being cultured for 4 days in ultra-low attachment plates after isolation from the hESC floc of FIG. 1A Left. Spherical morphology. Consisting of approx. 292±53 cells per floating aggregate.

(B)-(D). Morphological microphotographs of cells differentiating into retinal cells.

(B). Cells on Day 14 after induction of the differentiation, that is, after the floating aggregates were transferred to poly-D-lysine/laminin-coated plates and cultured for 10 days therein, which was on Day 14 after the induction of the differentiation of the undifferentiated hESCs. The cells were observed to be separated from the floating aggregates and to undergo differentiation. Morphology of cells in the early stage of differentiation, with meager cytoplasm and round, large nuclei.

(C). Cells on Day 19 after the induction of the differentiation, that is, cells after the undifferentiated hESCs were induced to differentiate for 19 days. They differentiated into retinal progenitor cells, with concomitant active proliferation. Cell flocs under active proliferation and differentiation formed an eddy formation or a rosette configuration.

(D). Cells on Day 21 after induction of the differentiation, showing an increased number of cells resulting from active proliferation. The cells became richer in cytoplasm and the size of their nucleus was smaller than those of FIG. 1C as the differentiation progressed. The cells appeared to function in response to light.

(E)-(H). Various morphologies of cell flocs on Day 29 after induction of the differentiation.

(E). The morphology of most cells, particularly observed in densely populated regions. With the progress of differentiation, the cells showed the same cellularity, but had a richer cytoplasm and smaller and denser nuclei, compared to those on Day 21 after induction.

(F). The morphology of cells in a scarcely populated region. The cell flocs showed directivity and moved towards a certain point which depended on the cell cluster. More plentiful, opposite end-pointed cytoplasms and spindle-like nuclei were observed.

(G). Cell flocs, some having a multiple of nerve bundles.

(H) Left. Cell flocs some of which show long neural axons.

(H) Right. Cell flocs some of which show the morphology of differentiated neurons.

*Microscopic field: (A) (left, right: 40× magnification); (B)-(G) (left: 50× magnification; right: 200× magnification); (H) (left and right: 200× magnification).

Figure 2:
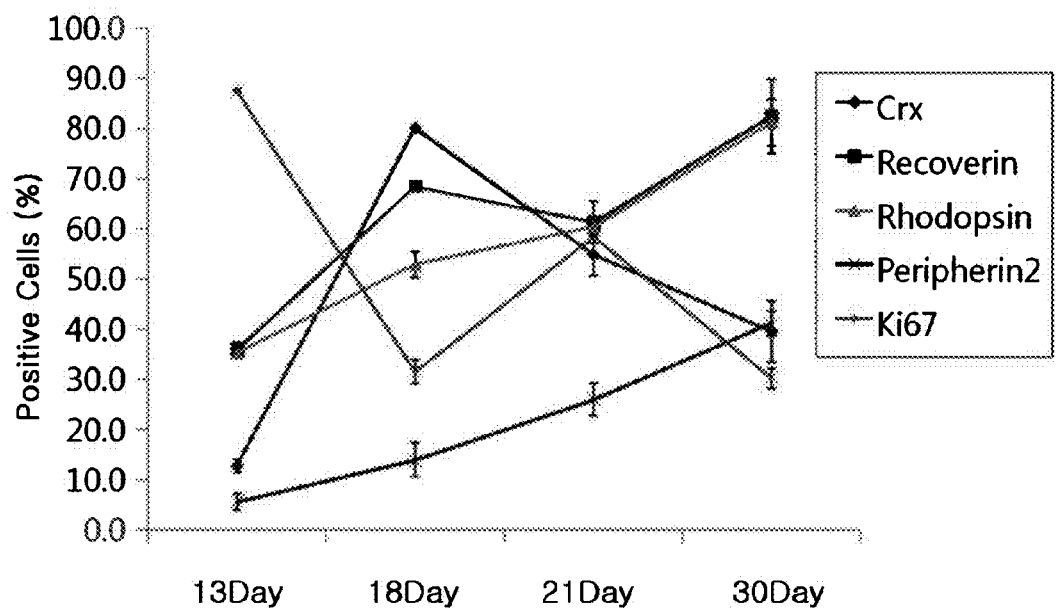

FIG. 2 is a graph showing changes in expression levels of the retinal cell markers Crx, recoverin, rhodopsin, peripherin2 and Ki67 with culture time period.

Figure 3:
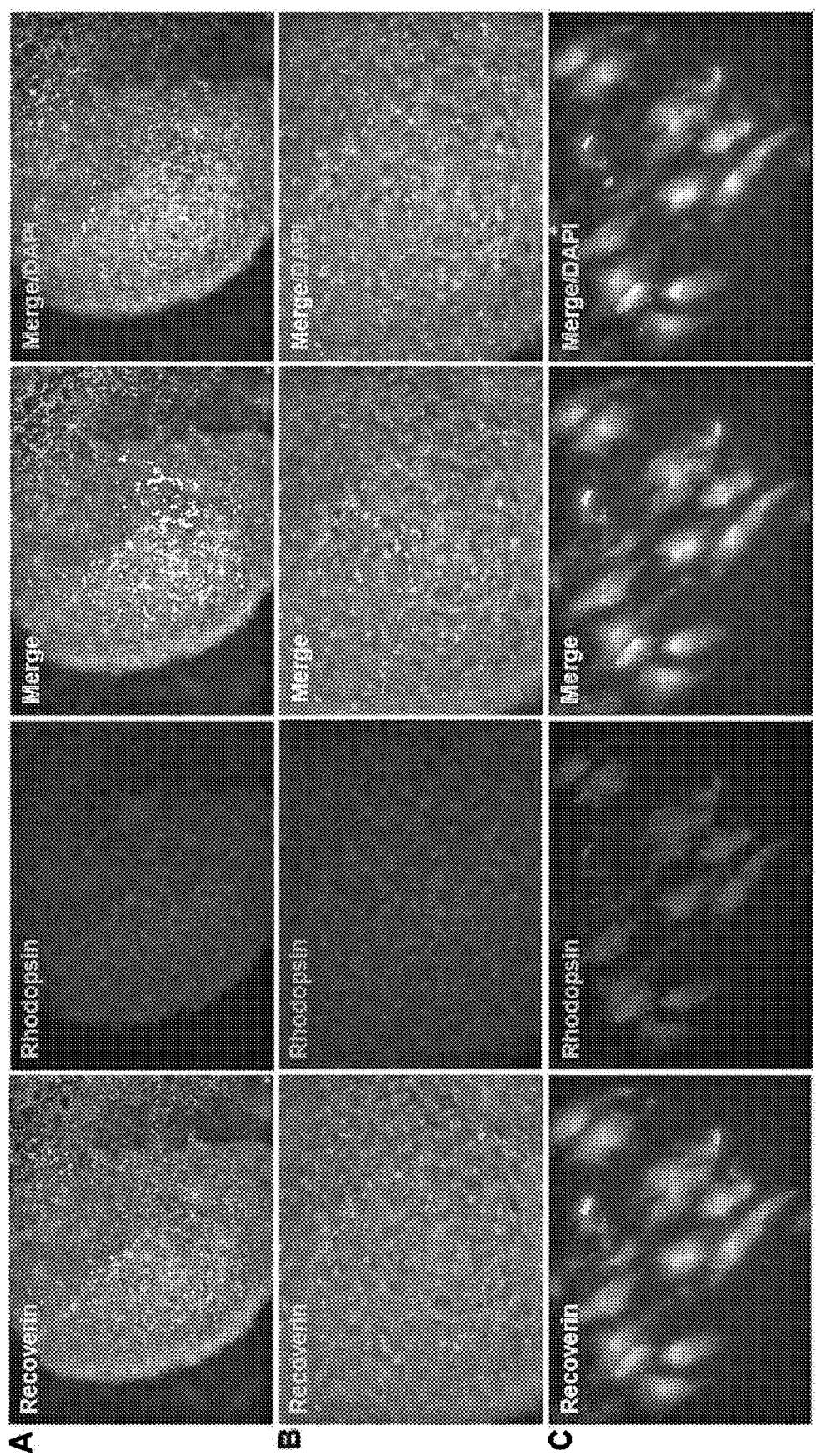

FIG. 3 is a set of microphotographs showing the cells obtained by differentiation into retinal cells for 29 days, which were immunostained for recoverin and rhodopsin, both indicative of photoreceptor cells.

After hESCs were induced to differentiate into photoreceptor cells, an examination was made of the expression of photoreceptor cell-specific proteins. More than 80% of the differentiated cells tested positive to both recoverin (a universal photoreceptor cell marker) and rhodopsin (characteristic of rod photoreceptor cells).

(A) and (B). Flocs of differentiated photoreceptor cells.

(C). Individual cells in scarcely populated regions.

Recoverin and rhodopsin are distinctively expressed in the differentiated photoreceptor cells.

*Microscopic field: (A) 100× magnification; (B) 200× magnification; (C) 400× magnification.

*Merge: superimposed photographs of cells which were fluorescent immunostained for recoverin and rhodopsin, cells expressing both the antigens being represented yellow (green+red).

*Merge/DAPI: DAPI is a nucleus-stained cell population. The Merge/DAPI images are of superimposed fluorescence photographs to detect the expression of both recoverin and rhodopsin and the expression of DAPI, showing cell contours and the expression pattern of the two antigens, simultaneously.

Figure 4:
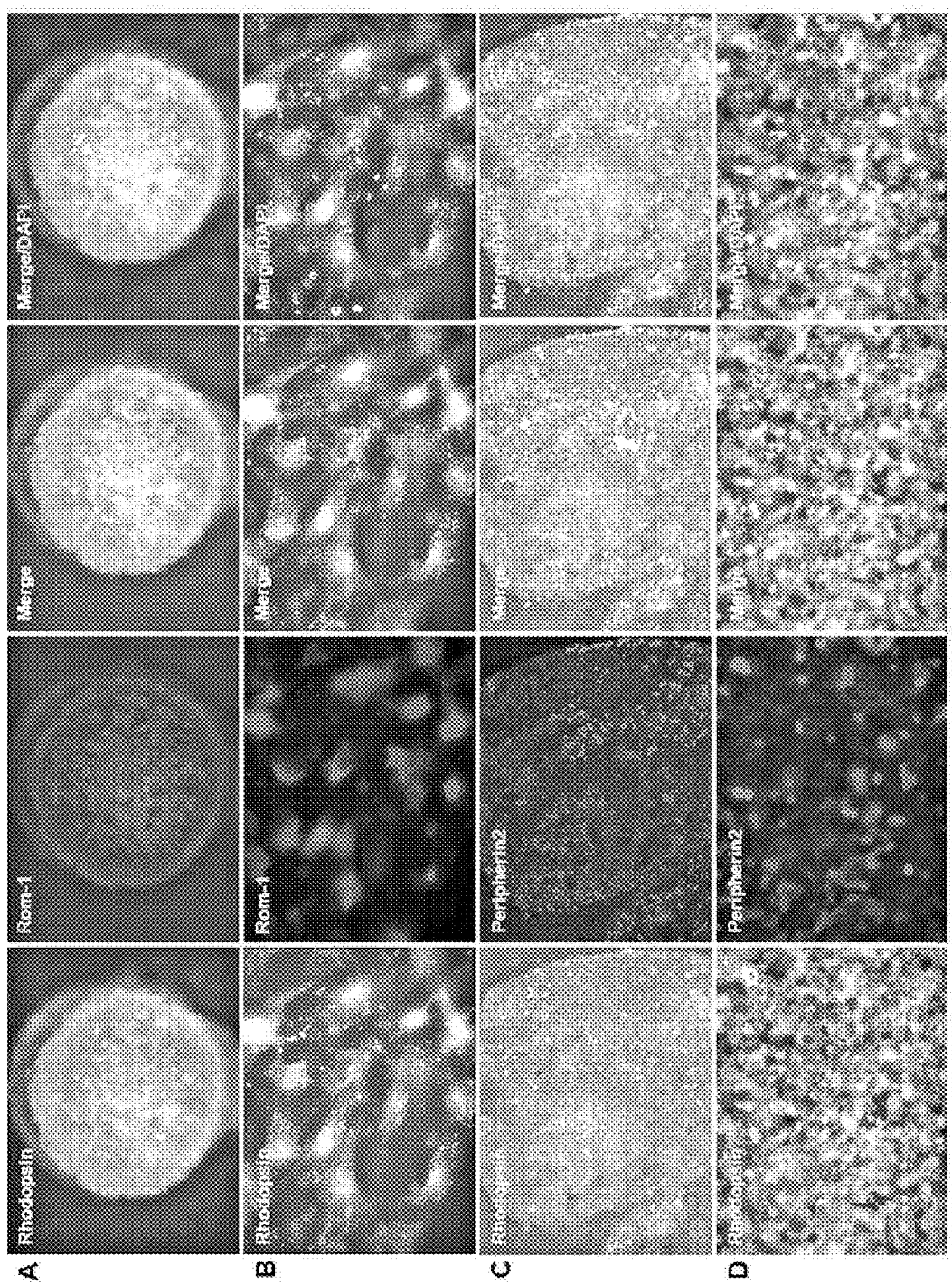

FIG. 4 is of fluorescence microphotographs of the cells obtained after inducing differentiation into retinal cells for 29 days, showing the expression of the photoreceptor cell markers rhodopsin, rom-1 and peripherin2.

The differentiated photoreceptor cells were observed to express Rom-1 and peripherin2, both characteristic of the outer segment of rhodopsin-positive rod photoreceptor cells.

(A). Cell flocs positive to both rhodopsin and rom-1.

(B). Individual cells positive to both rhodopsin and rom-1. Within each cell, rhodopsin and rom-1 were expressed at distinctly different positions. With the progress of differentiation, rhodopsin was expressed in the inner cytoplasm while rom-1 was positioned at the outermost cytoplasm.

(C). Flocs of the differentiated photoreceptor cells which were positive to both rhodopsin and peripherin2.

(D). Individual cells positive to both rhodopsin and peripherin2.

*Microscopic field: (A) 100× magnification; (B) 400× magnification; (C) 100× magnification; (D) 400× magnification.

Figure 5:
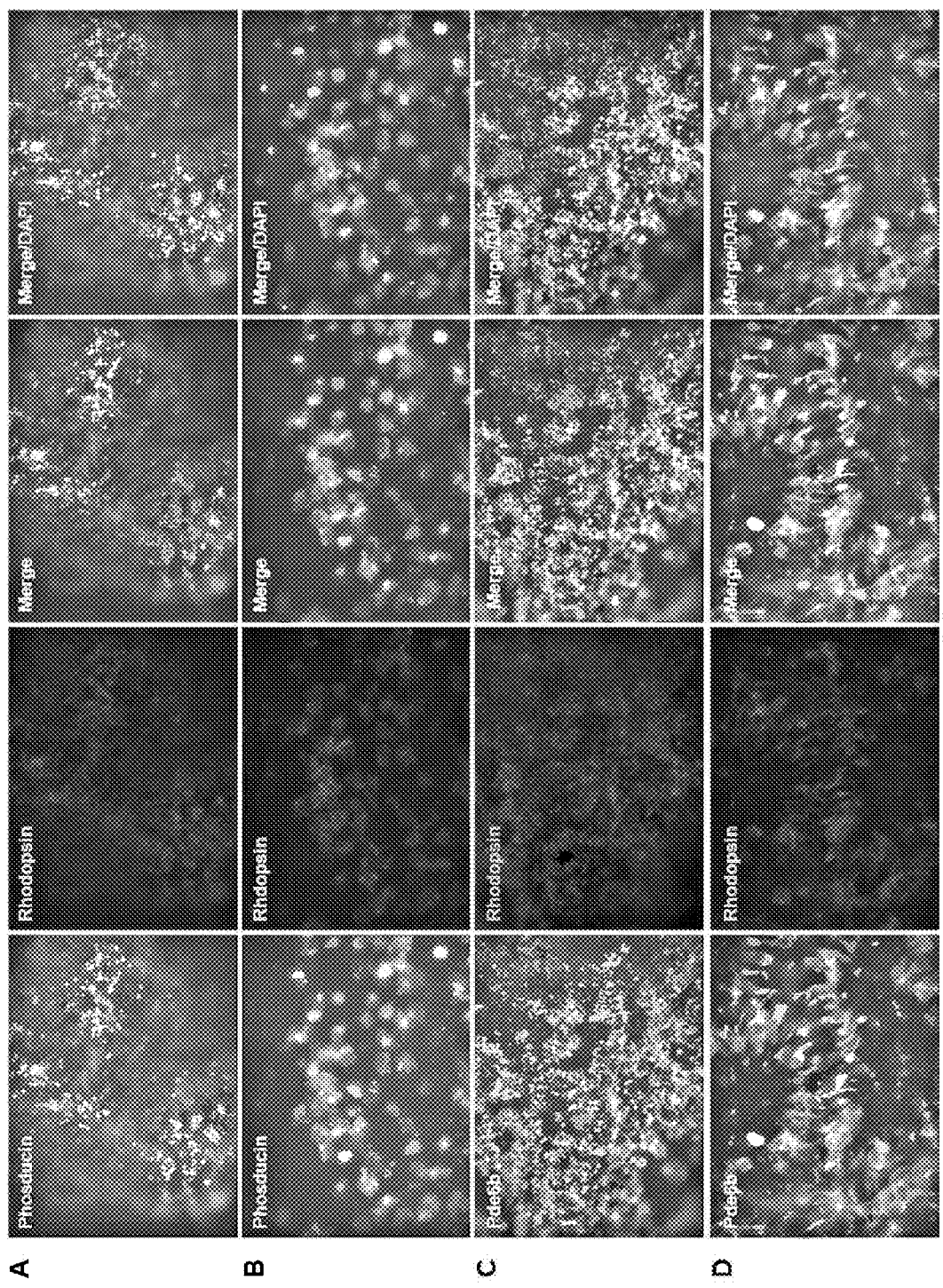

FIG. 5 is of fluorescence microphotographs of the cells obtained after inducing differentiation into retinal cells for 29 days, showing the expression of the photoreceptor cell markers rhodopsin, phosducin and Pde6b. These proteins are responsible for the response to light, demonstrating that the differentiated photoreceptor cells are exhibiting their proper functions.

(A). Flocs of the differentiated photoreceptor cells which are positive to both rhodopsin and phosducin.

(B). Individual cells positive to both rhodopsin and phosducin.

(C). Flocs of the differentiated photoreceptor cells positive to both rhodopsin and Pde6b.

(D). Individual cells positive to rhodopsin and Pde6b.

*Microscopic field: (A) 100× magnification; (B) 400× magnification; (C) 100× magnification; (D) 400× magnification.

Figure 6:
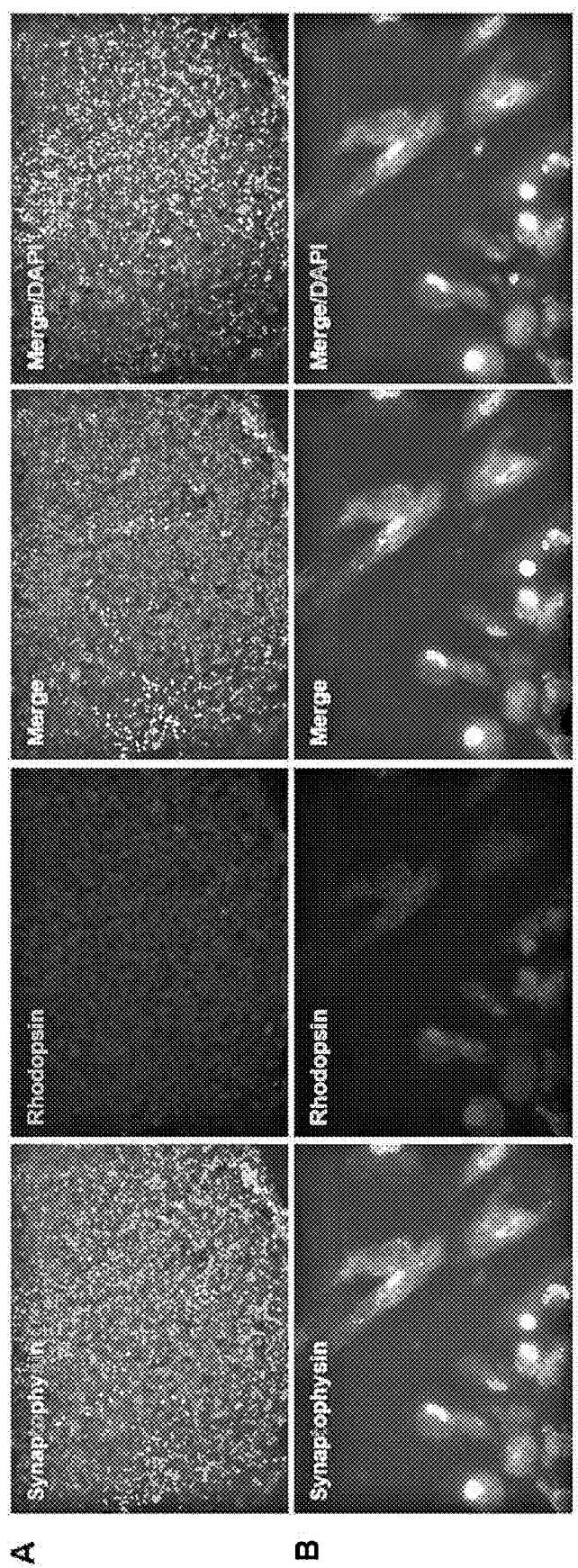

FIG. 6 is of fluorescence microphotographs of cells obtained after inducing differentiation into retinal cells for 29 days, showing the expression of the photoreceptor cell markers rhodopsin and synaptophysin.

(A). Flocs of the differentiated photoreceptor cells positive to both rhodopsin and synaptophysin. The expression of these proteins demonstrates that the differentiated photoreceptor cells are in synapse interaction with other retinal neurons and are participating in the formation of retinal nerve circuits.

(B). Individual cells positive to rhodopsin and synaptophysin.

*Microscopic fields: (A) 100× magnification; (B) 400× magnification.

Figure 7:
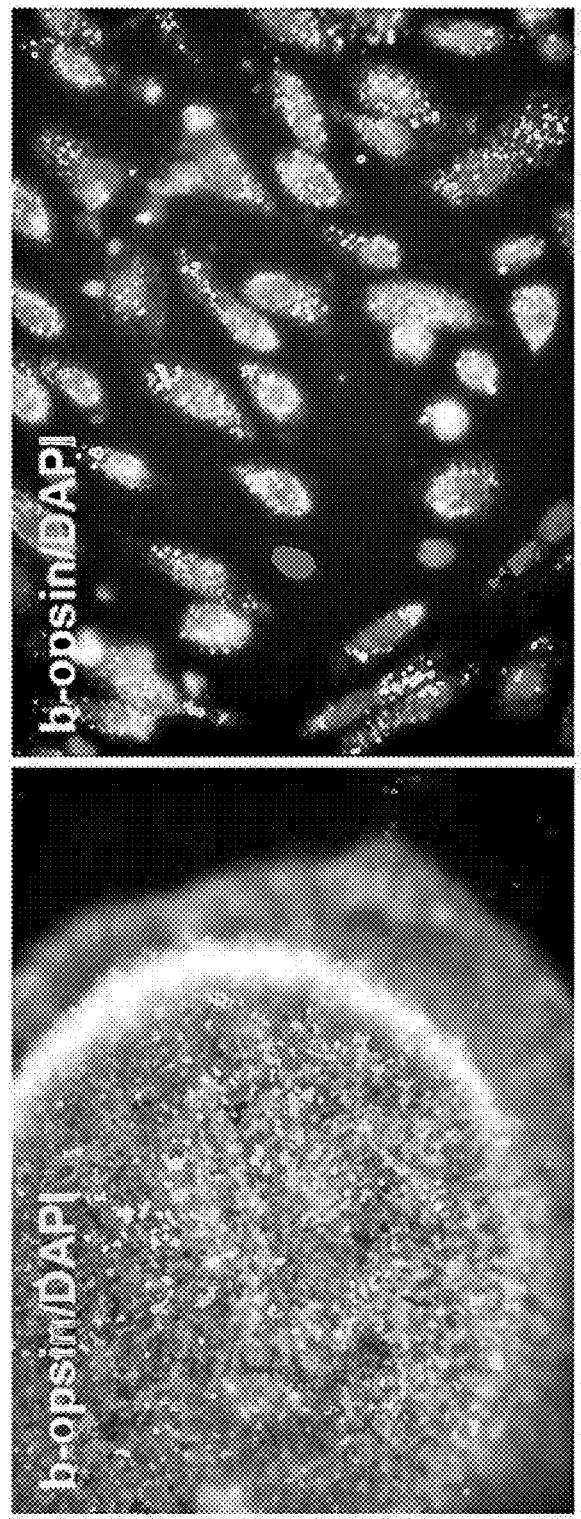

FIG. 7 is of fluorescence microphotographs of cells which were obtained after inducing differentiation into retinal cells for 29 days and immunostained against cone photoreceptor cells.

Left panel. Cell flocs positive to blue opsin.

Right panel. Individual cells positive to blue opsin.

The expression of blue-opsin is evidence that the differentiated cells are blue opsin-cone photoreceptor cells.

*Microscopic field (left) 100× magnification; (right) 400× magnification.

Figure 8:
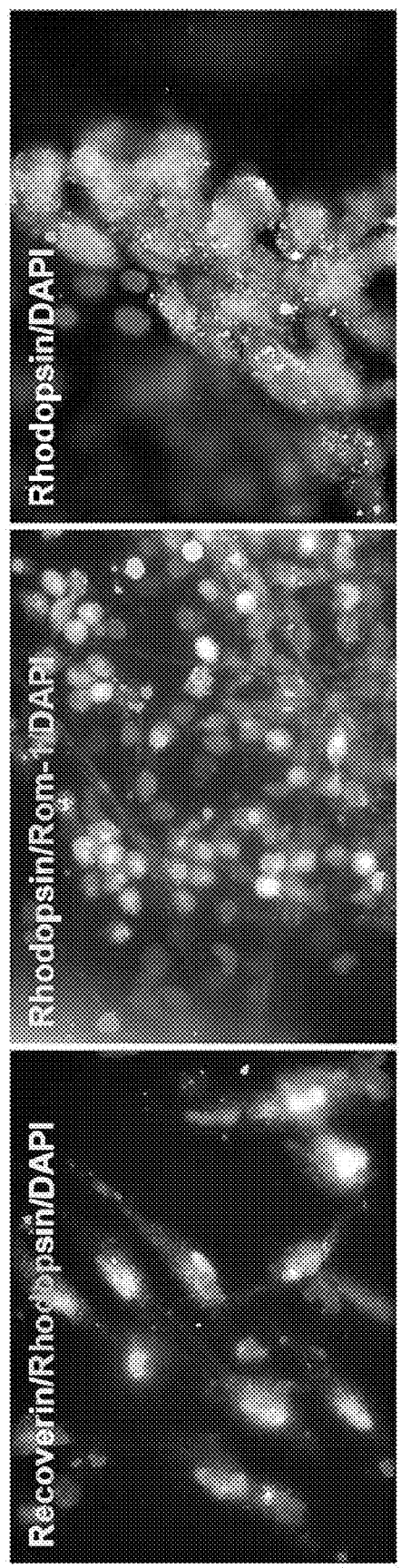

FIG. 8 is of fluorescence microphotographs of cells which were obtained after inducing differentiation into retinal cells for 29 days and which were immunostained against characteristic photoreceptor cells. Various types of cells which had undergone further differentiation were observed.

Left. Cells positive to both recoverin and rhodopsin, showing a morphology characteristic of photoreceptor cells.

Middle. Cells positive to synaptophysin and rhodopsin, showing further mature differentiation.

Right. Rhodopsin-positive cells characterized by rich rhodopsin molecules within the cytoplasm.

*Microscopic field 400× magnification.

Figure 9:
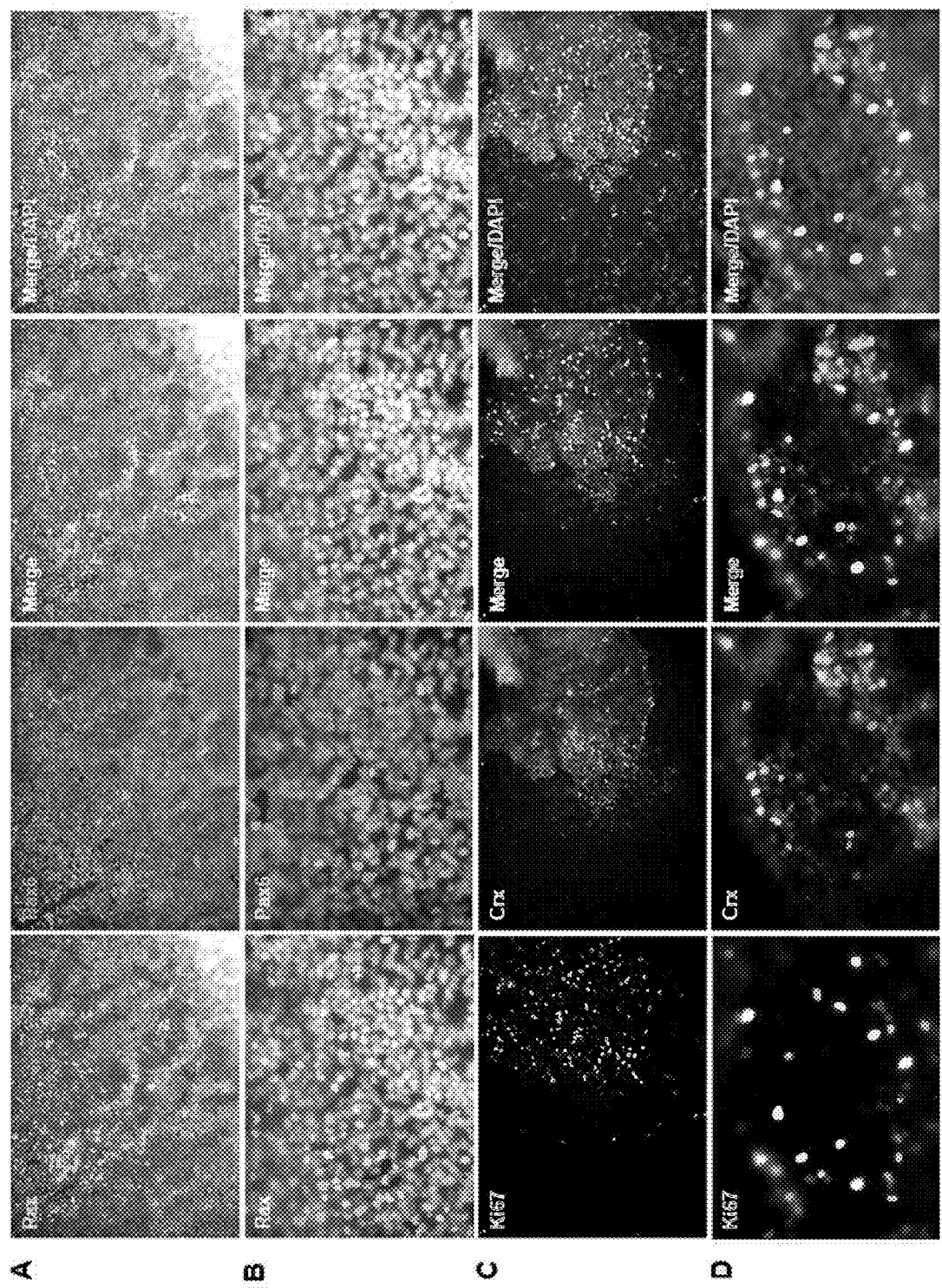

FIG. 9 is of fluorescence microphotographs of cells which were obtained after inducing differentiation into retinal cells for 29 days and which were immunostained against neural retinal progenitor cells and photoreceptor cell precursors.

(A). Cell flocs positive to both Rax and Pax6.

(B). Individual cells positive to both Rax and Pax6.

Most cells were observed to express both the antigens although the expression level was different between them, indicating that the retinal cells obtained after differentiation induction for 29 days were derived from neural retinal progenitor cells.

(C). Cell flocs positive to the proliferative cell marker Ki67 and the photoreceptor cell precursor marker Crx.

(D). Individual cells positive to both Ki67 and Crx.

Most Crx-positive cells do not express Ki67. This coincides with the fact that photoreceptor cell precursors express Crx immediately after leaving the cell proliferation cycle. Sometimes, a minority of Crx-positive cells still continue to express Ki67.

*Microscopic field (A) 100× magnification; (B) 400× magnification; (C) 100× magnification; (D) 400× magnification.

Figure 10:
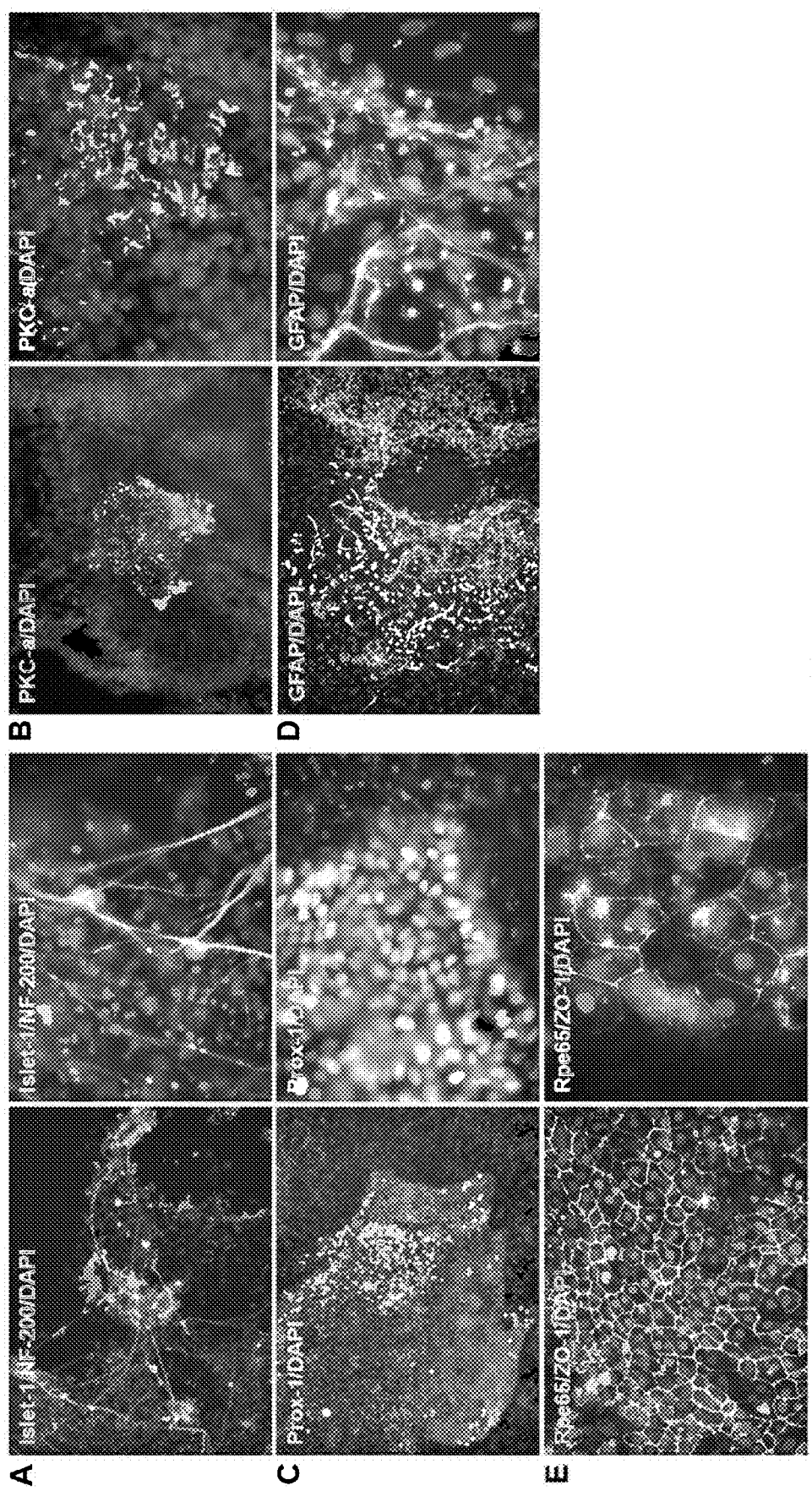

FIG. 10 is of fluorescence microphotographs of cells which were obtained after inducing differentiation into retinal cells for 29 days and immunostained against retinal cells other than photoreceptor cells.

(A). Cell flocs (left) and individual cells, positive to both Islet-1 and NF-200, which gives evidence of retinal ganglion cells because nuclei and axons are positive to Islet-1 and NF-200, respectively.

(B). Cell flocs (left) and individual cells (right) positive to PKC-α, which gives evidence of bipolar cells.

(C). Cell flocs (left) and individual cells (right) positive to Prox-1, which gives evidence of horizontal cells.

(D). Cell flocs (left) and individual cells (right) positive to GFAP, which gives evidence of Muller glial cells.

(E). Cell flocs (left) and individual cells (right) positive to both Rpe65 and ZO-1, which gives evidence of retinal pigmented epithelium.

*Microscopic field: (A). Left. 100× magnification, Right. 400× magnification; (B) Left. 100× magnification, Right. 400× magnification; (C) Left. 100× magnification, Right. 400× magnification; (D) Left. 100× magnification, Right. 400× magnification; (E) Left. 100× magnification, Right. 400× magnification.

Figure 11:
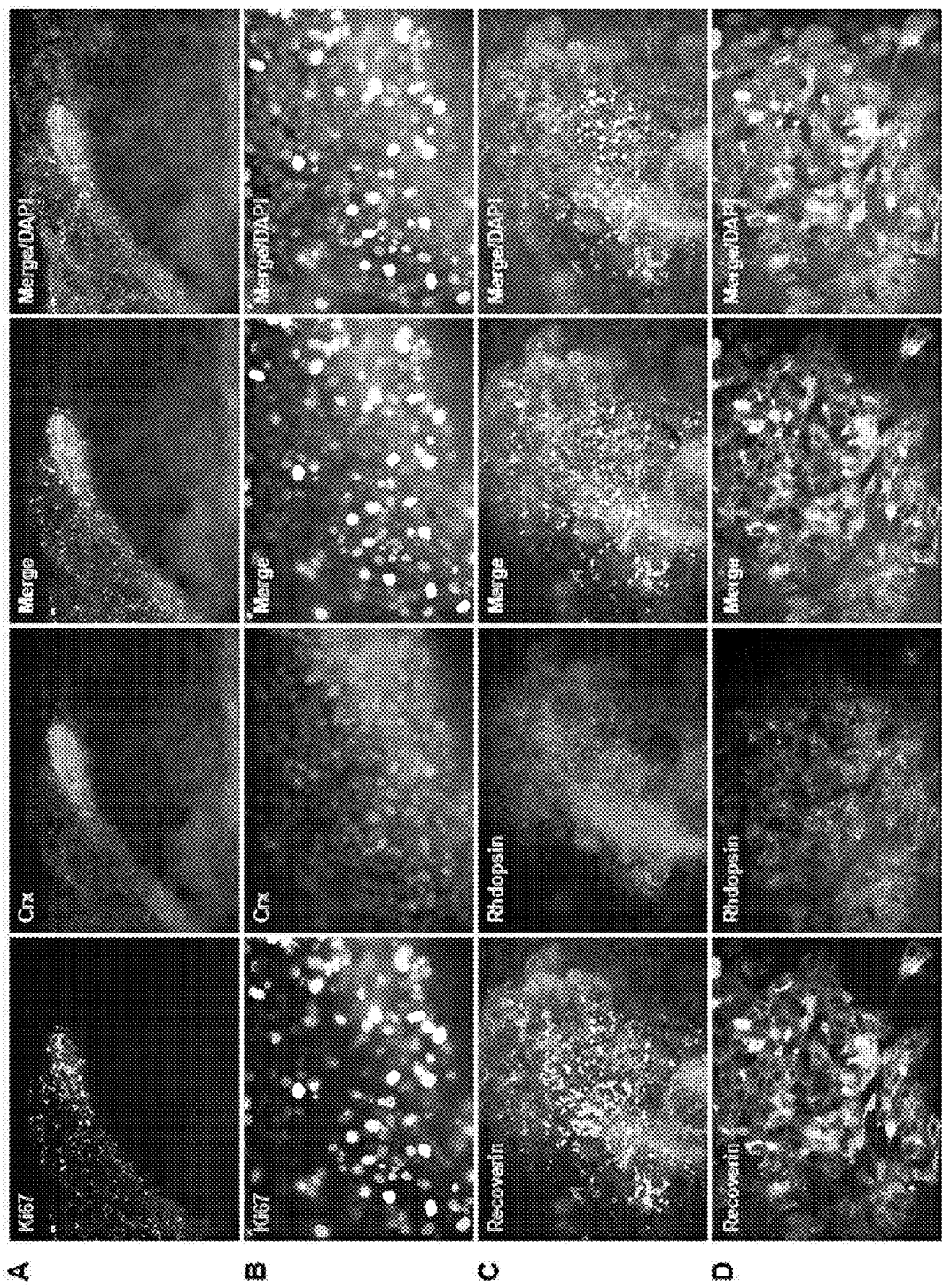

FIG. 11 is of fluorescence microphotographs of the cells resulting from inducing differentiation into retinal cells for 29 days, with BIO and purmorphamine used respectively instead of Wnt3a and Shh, which were immunostained against photoreceptor cell precursors and photoreceptor cells.

(A). Cell flocs positive to both the proliferative cell marker Ki67 and the photoreceptor cell precursor-specific antigen Crx.

(B). Individual cells positive to both Ki67 and Crx.

(C). Cell flocs positive to the photoreceptor cell markers recoverin and rhodopsin.

(D). Individual cells positive to recoverin and rhodopsin.

*Microscopic field (A) 100× magnification; (B) 400× magnification; (C) 100× magnification; (D) 400× magnification.

Figure 12:
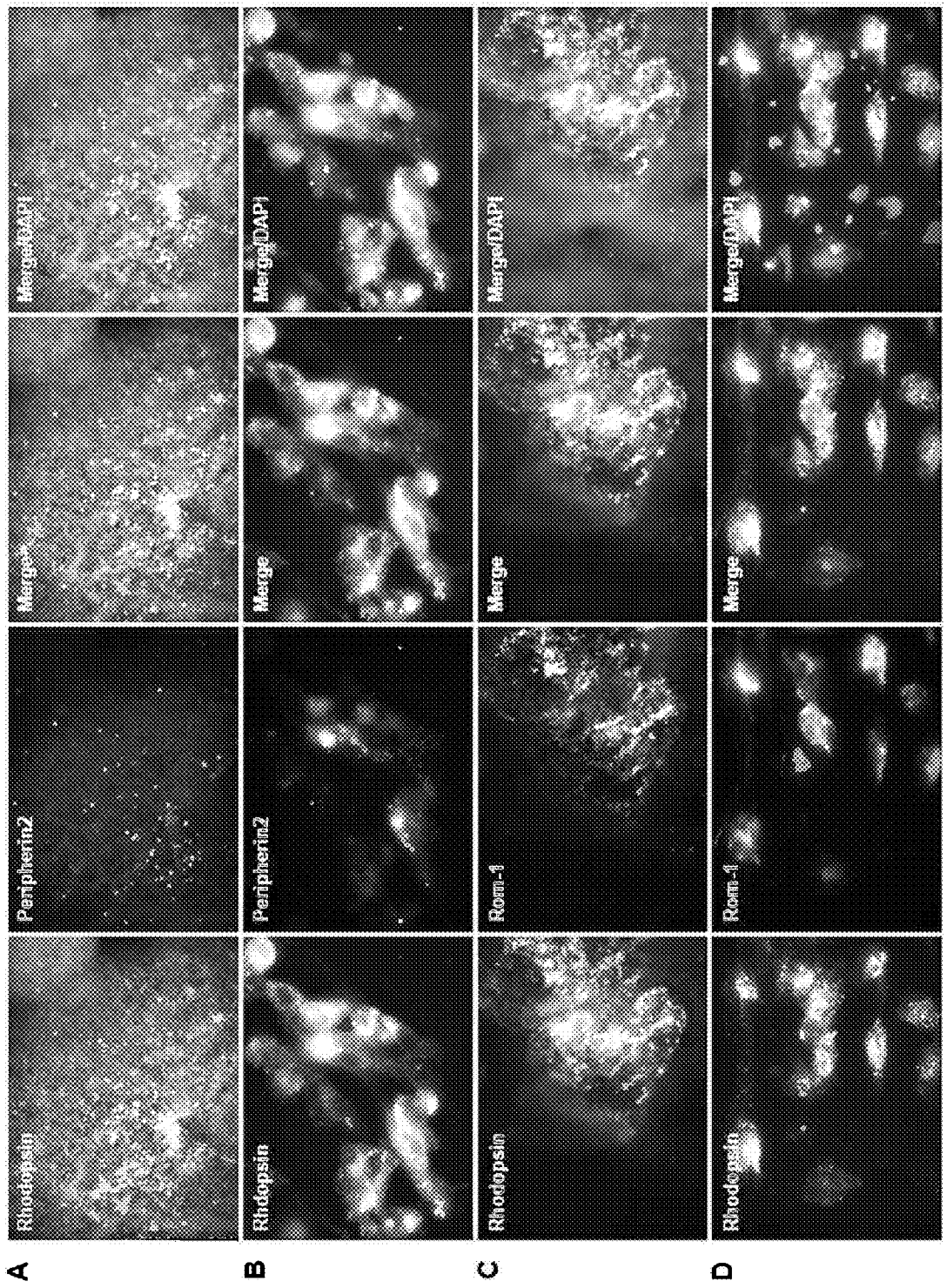

FIG. 12 is of fluorescence microphotographs of the cells resulting from inducing differentiation into retinal cells for 29 days, with BIO and purmorphamine used respectively instead of Want3a and Shh, which were immunostained for the photoreceptor cell markers rhodopsin, peripherin2 and rom-1.

(A). Cell flocs positive to both rhodopsin and peripherin2.

(B). Individual cells positive to both rhodopsin and peripherin2.

(C). Cell flocs positive to both rhodopsin and rom-1.

(D). Individual cells positive to both rhodopsin and rom-1.

*Microscopic field: (A) 100× magnification; (B) 400× magnification; (C) 100× magnification; (D) 400× magnification.

Figure 13:
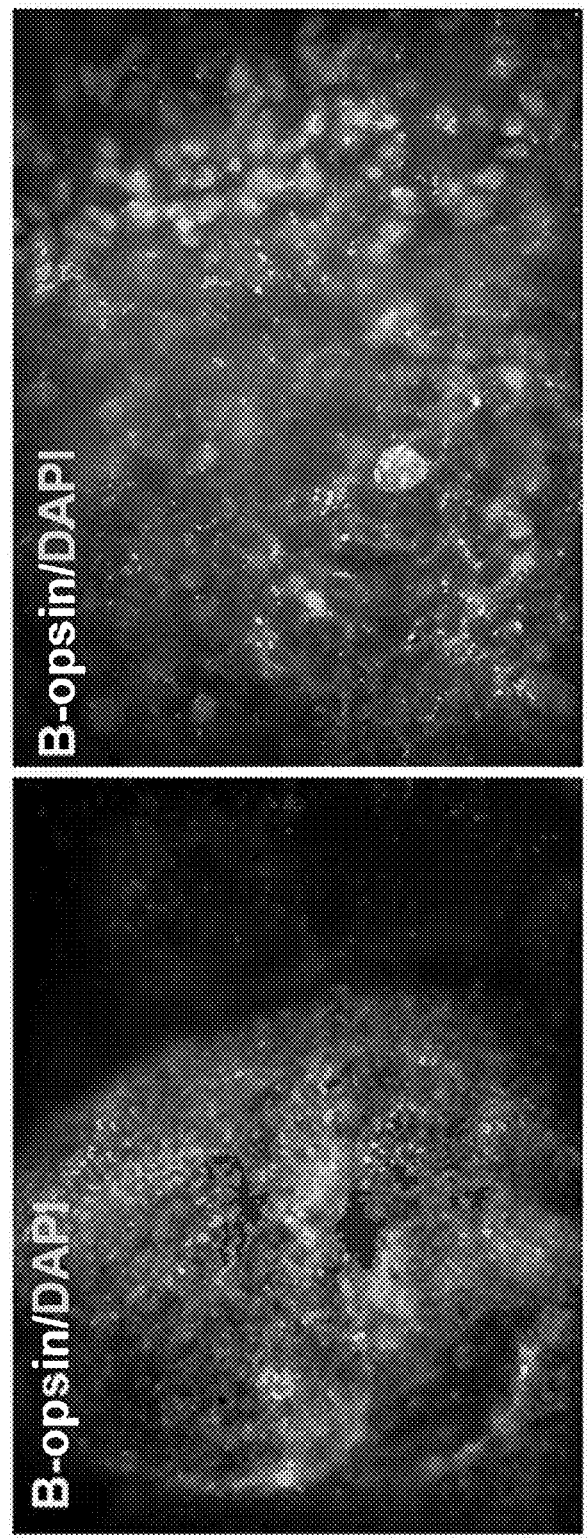

FIG. 13 is of fluorescence microphotographs of the cells resulting from inducing differentiation into retinal cells for 29 days, with BIO and purmorphamine used respectively instead of Want3a and Shh, which were immunostained against cone photoreceptor cells.

Left. Blue-opsin-positive cell flocs.

Right. Blue-opsin-positive individual cells.

*Microscopic field (Left) 100× magnification; (Right) 400× magnification.

Figure 14:
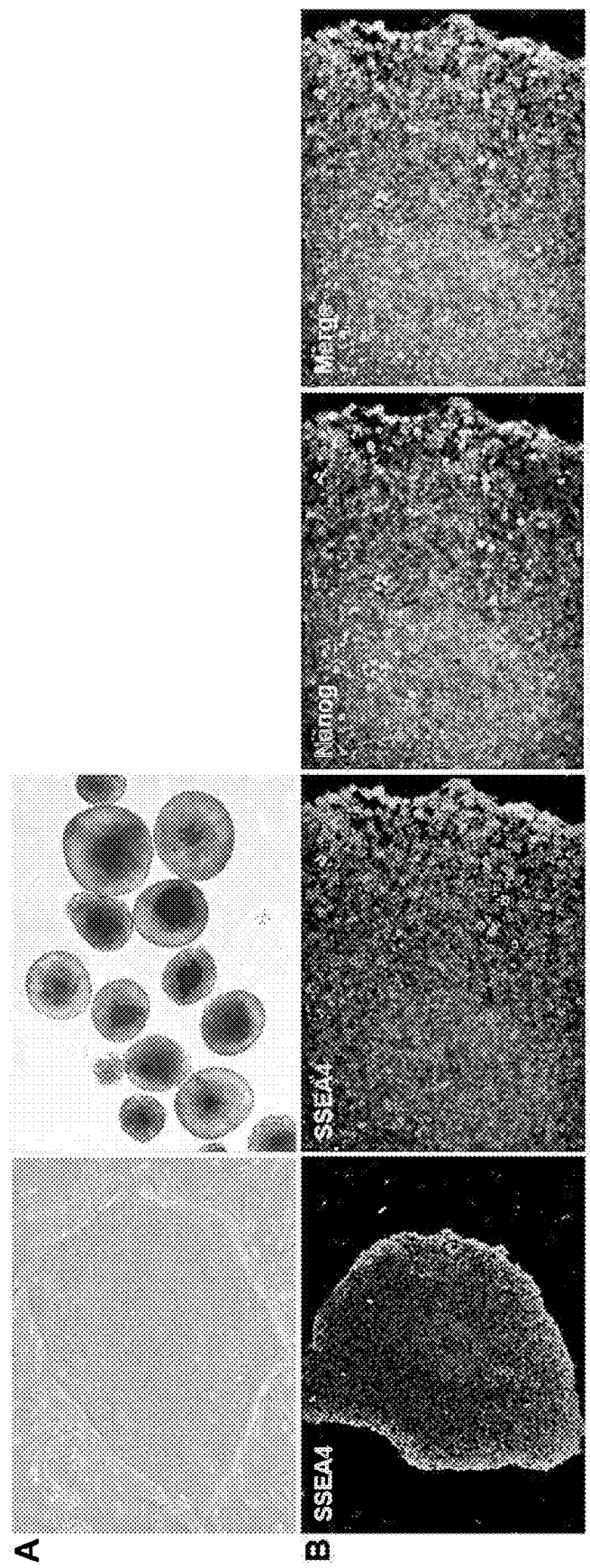

FIG. 14 is of microphotographs of human iPSCs.

(A). Cytomorphological microphotographs. (A) Left. Typical cell floc of human iPSCs in an undifferentiated state (passages 43; Microscopic field: 40 magnifications), after being cultured for 6 days from cells of passages 43. Characterized by definite separation from adjacent MEF feeder cells. Having a plain surface and uniform morphology, which is also characteristic of undifferentiated hESCs. (A) Right. Floating aggregates (Microscopic field: 40× magnification), being cultured for 4 days in ultra-low attachment plates after isolation from the human iPSC floc of FIG. 14A Left.

(B). Fluorescence microphotographs of undifferentiated human iPSCs immunostained for characteristic markers. Cell flocs in which most cells are positive to both SSEA4 and Nanog, which gives evidence of the continuance of undifferentiated states.

*Microscopic field (leftmost) 40× magnification; (the others) 100× magnification.

Figure 15:
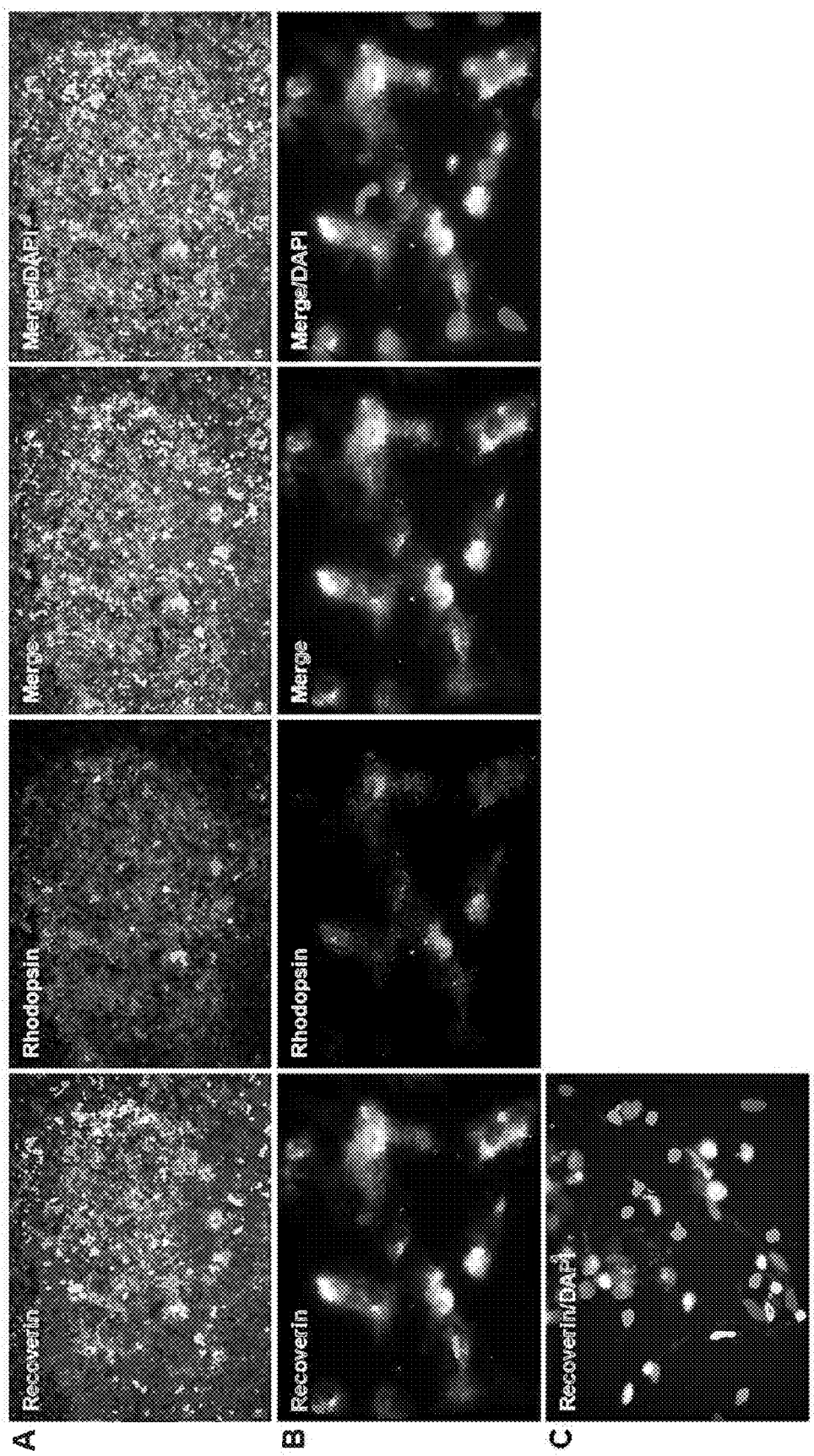

FIG. 15 is a set of fluorescence microphotographs showing the cells obtained by inducing human iPSC to differentiate into retinal cells for 29 days, which were immunostained for recoverin and rhodopsin, both characteristic of photoreceptor cells.

The photoreceptor cells differentiated from human iPSCs were assayed for the expression of photoreceptor cell-specific proteins.

(A). Flocs of differentiated photoreceptor cells.
(B). Individual cells at the low cell density area.
(C). Individual cells in scarcely populated regions.

Recoverin and rhodopsin are distinctively expressed in the differentiated photoreceptor cells.

*Microscopic field: (A) 100× magnification; (B) 400× magnification; (C) 400× magnification.

Figure 16:
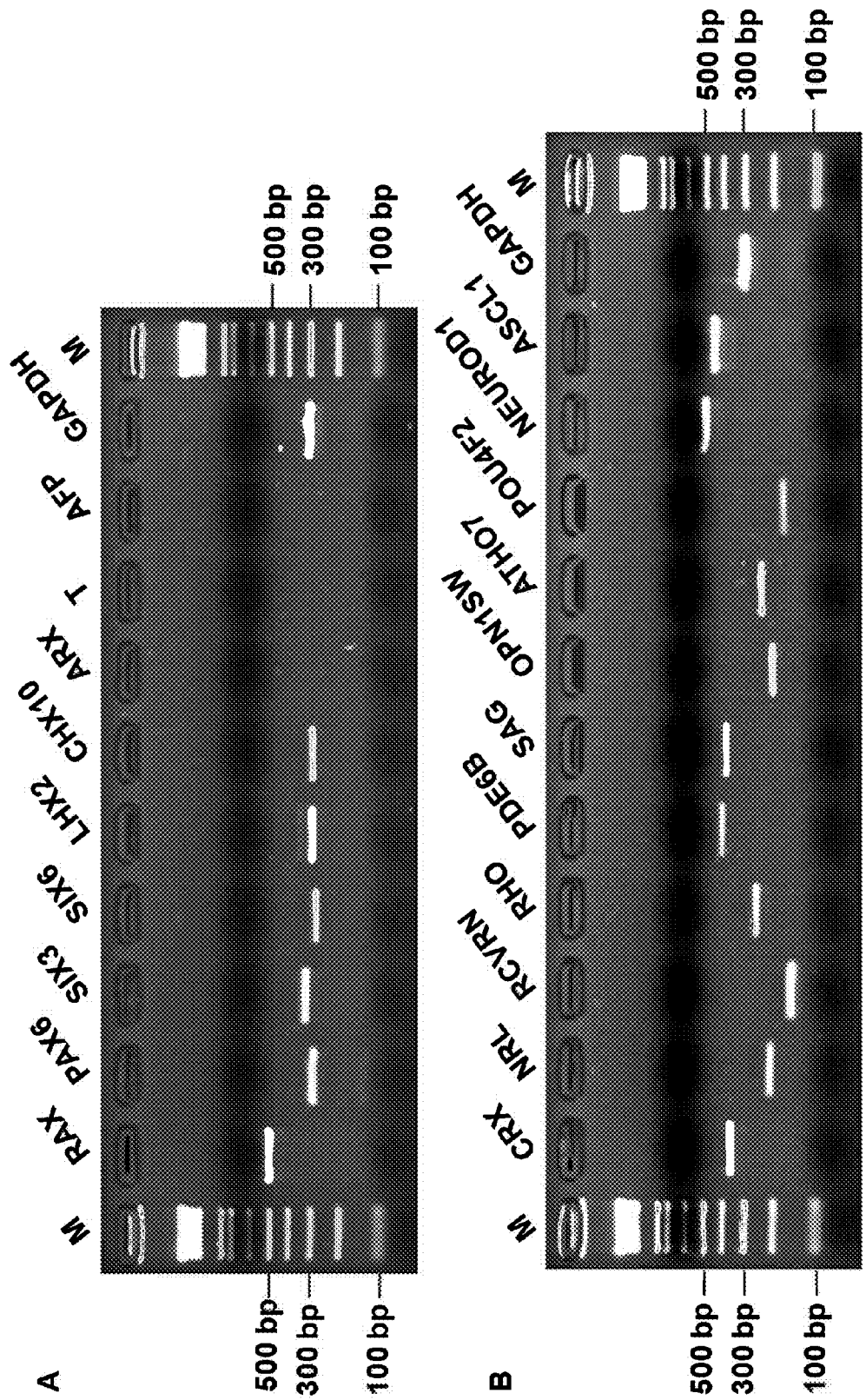

FIG. 16 is of photographs showing RT-PCR for genes specific for retinal cells. The cells generated by inducing undifferentiated hESCs to differentiate into retinal cells for 29 days were assayed for the mRNA expression levels of genes associated with retinal progenitor cells, photoreceptor cells and other retinal cells using RT-PCR.

(A). RT-PCR products of the retinal progenitor cell-specific genes RAX (495 bp), PAX6 (275 bp), SIX3 (307 bp), SIX6 (272 bp), LHX2 (285 bp) and CHX10 (281 bp). Inter alia, RAX and PAX6 were expressed to the same high extent as was the quantitative control gene GAPDH (PCR product size: 302 bp). In contrast, none of the developing cerebral cortex-relevant gene ARX (462 bp), the developing mesodermal gene T (541 bp), or the developing endodermal gene AFP (318 bp) were found in the RT-PCR products, suggesting that the method of the present invention is specifically directed to the mRNA expression of retina-relevant genes.

(B). RT-PCR products of genes associated with photoreceptor cells and other retinal cells. The photoreceptor cell-relevant genes CRX (353 bp), NRL (206 bp), RCVRN (150 bp), RHO (258 bp), PDE6B (409 bp), SAG (400 bp) and OPN1SW (206 bp) were observed to be amplified by RT-PCR. The retinal ganglion cell genes ATHO7 (246 bp) and POU4F2 (175 bp), the amacrine cell gene NEUROD1 (523 bp), and the bipolar cell gene ASCL1 (467 bp) were also found in the RT-PCR products.

Characteristics of photoreceptor cell-relevant genes are as follows: CRX and NRL are transcription genes characteristic of photoreceptor cell precursors and rod photoreceptor cells, respectively. RCVRN (recoverin) is a universal photoreceptor cell gene that tests positive for both cone and rod photoreceptor cells. RHO (rhodopsin) is rod photoreceptor cell specific. PDE6B and SAG (human arrestin) are involved in the phototransduction of photoreceptor cells. The expression of these genes gives evidence of the development and maturation of the photoreceptor cell's own functions. OPN1SW is characteristic of short wave (blue opsin)-cone photoreceptor cells. M: marker.

Figure 17:
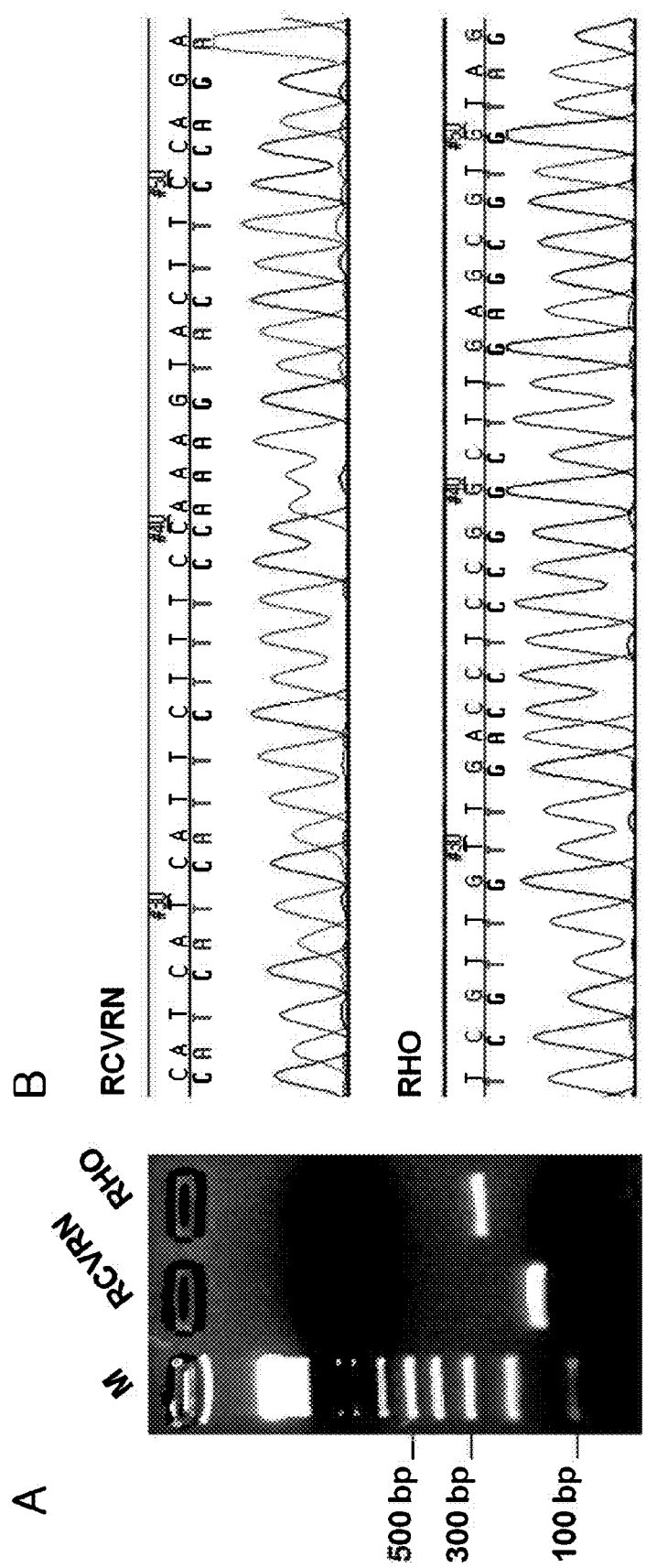

FIG. 17 shows RT-PCR and base sequencing results of genes characteristic of photoreceptor cells.

RT-PCR was performed on the cells generated by inducing undifferentiated hESCs to differentiate into retinal cells for 29 days, so that the photoreceptor cell-specific genes RCVRN (NM_002903.2) and RHO (NM_000539.3) could be detected. The RT-PCR products were identified as RCVRN and RHO by base sequencing.

(A). Agarose gel electrophoresis of the RT-PCR products showing RCVRN at 150 bp and RHO at 258 bp. M: marker.

(B). Chromatogram of base sequencing analysis, showing an RCVRN base sequence (top) and an RHO base sequence (bottom). The RCVRN and RHO gene base sequences were found to perfectly coincide with human standard sequences (http://www.ncbi.nlm.nih.gov/), indicating that the photoreceptor cells express human RCVRN and RHO genes.

FIG. 18 is of electroretinograms of the retinal degeneration mouse rd/SCID which had been or had not been transplanted with the hESC-derived photoreceptor cells.

(A). Electroretinograms of 8-week-old, non-transplanted mice. No characteristic ERG wave forms were found. The ERG b-wave had an amplitude of 6.29 μV for the right eye and 0.0542 μV for the left eye.

(B). Electroretinograms of 8-week-old mice 4 weeks after the transplantation. Compared to the non-transplanted right eye, the EGR b-wave from the photoreceptor cell-transplanted left eye formed characteristic wave forms, with an amplitude of as high as 74.5 μV. The rd/SCID mice transplanted with the hESC-derived photoreceptor cells showed definite responses to light stimuli as measured by electroretinography.

Figure 19:
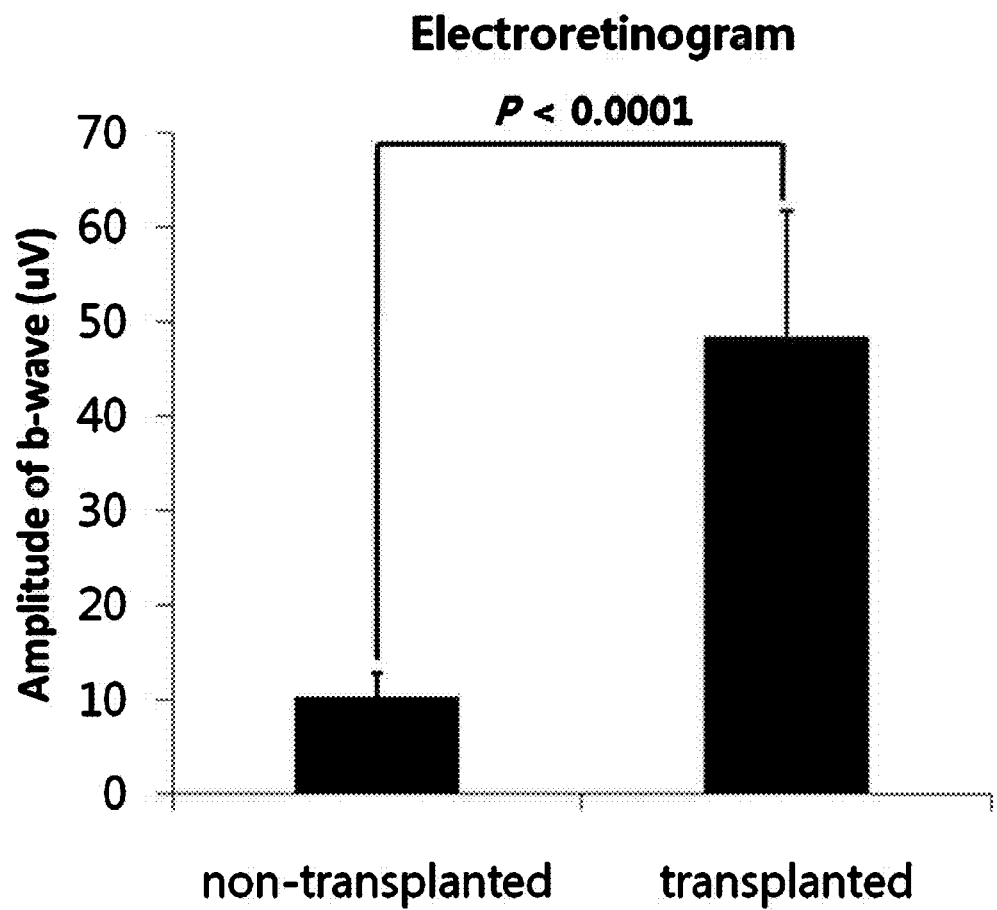

FIG. 19 is a graph comparing the amplitude of the b-wave between rd/SCID mice with retinal degeneration which had been transplanted or had not been transplanted with the hESC-derived photoreceptor cells.

The ERG b-wave from the photoreceptor cell-transplanted rd/SCID mice formed characteristic wave forms, with an amplitude of 48.4 (±3.4) μV (sample size=13). In contrast, characteristic wave forms where nowhere to be found in the ERG of the non-transplanted group, which showed a b-wave amplitude of 10.3 (±2.5) μV (sample size=17) which is different from that of the transplanted group with statistical significance ($p<0.0001$) (Table 6, FIG. 19).

Figure 20:
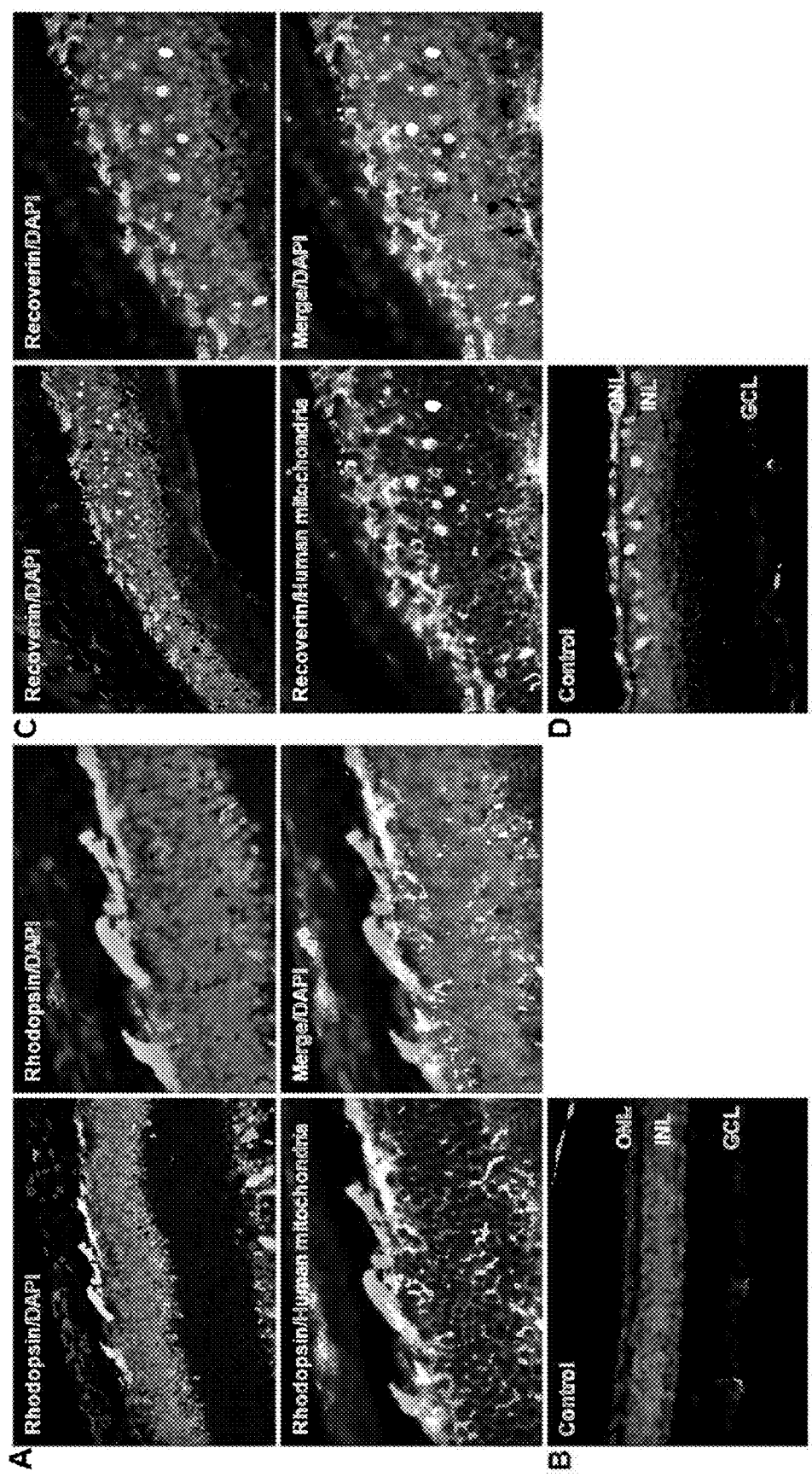

FIG. 20 is of fluorescence microphotographs after the hESC-derived photoreceptor cells had been transplanted into the mouse model of retinal degeneration (rd/SCID).

Four weeks after the transplantation, the hESC-derived photoreceptor cells were analyzed for engraftment into the retina using rhodopsin and recoverin, both characteristic of human mitochondria and photoreceptor cells. When cells positive to rhodopsin and recoverin showed a positive response to a human mitochondrial antigen, they were decided to be hESC-derived photoreceptor cells.

(A). Immunostained human-specific mitochondria and rhodopsin in the transplanted group. A new outer nuclear layer (ONL) was formed of a 4- or 5-fold, rhodopsin-positive photoreceptor cell layer.

(B). Immunostained human-specific mitochondria and rhodopsin in the non-transplanted group of rd/SCID mice of the same age (8 weeks old) which served as a control. Only a single outer nuclear layer was observed, consisting mostly of cone photoreceptor cells. Almost no rod photoreceptor cells were observed due to degeneration while only two residual cells which were undergoing degeneration were detected.

(C). Immunostained human-specific mitochondria and recoverin in the transplanted group. A 4- or 5-fold recoverin-positive cell layer formed a new outer nuclear layer. In the transplanted group, a 4- or 5-fold recoverin-positive cell layer was formed in the outer nuclear layer as well as in the inner nuclear layer (INL).

(D). Immunostained human-specific mitochondria and recoverin in the non-transplanted group used as a control. Positive responses were detected in a total of 40 cells. A single recoverin-positive outer nuclear layer consisted of cone-photoreceptor cells while the recoverin-positive inner nuclear layer was formed of cone-bipolar cells.

*Microscopic field: (A) and (C) Left. 200× magnification; (A)-(D): 400× magnification.

*ONL: outer nuclear layer

INL: inner nuclear layer

RGC: retinal ganglion cell

Figure 21:
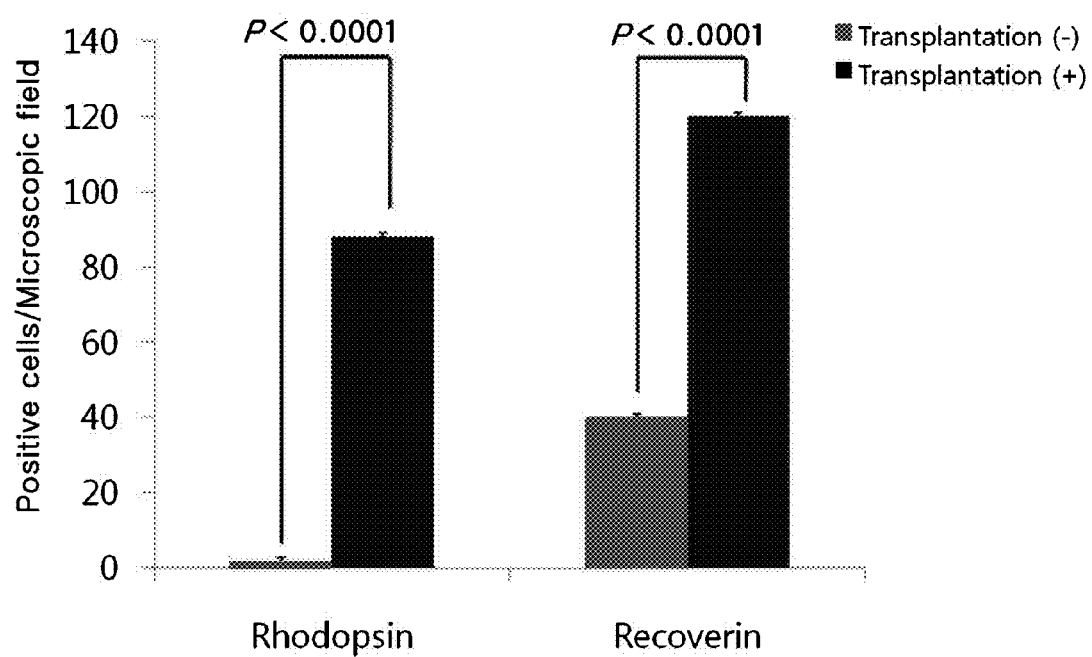

FIG. 21 is a graph showing engraftment results after human ESC-derived photoreceptor cells were transplanted into the mouse model of retinal degeneration (rd/SCID).

In the non-transplanted group, rhodopsin was detected in only two of a total of 199 cells per observation microscopic field (positive rate: 1.0%). On the other hand, 88 of a total of 215 cells per microscopic field were rhodopsin positive in the transplanted group (positive rate: 40.8%) ($p<0.0001$). Accordingly, the transplanted rod photoreceptor cells were found to occupy approximately 40% of the total area of the retinal sections. Positive responses to recoverin were detected in 40 of the total of 168 cells per microscopic field in the non-transplanted group (positive rate: 23.8%), but in 120 of the total 292 cells per microscopic field in the transplanted group (positive rate: 41.0%), with statistical significance ($p<0.0001$).

Figure 22:
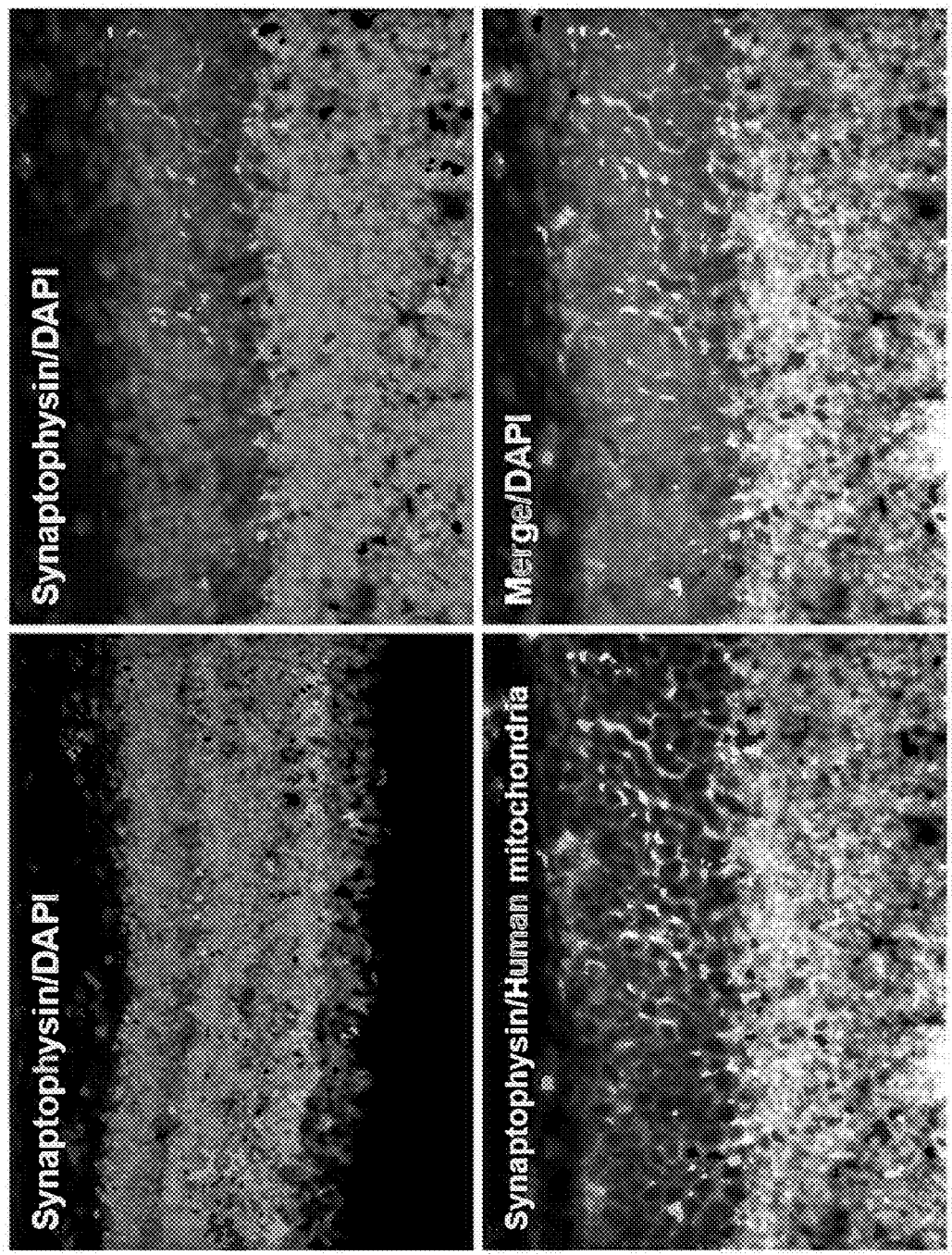

FIG. 22 is of fluorescence microphotographs after the hESC-derived photoreceptor cells had been transplanted into the mouse model of retinal degeneration (rd/SCID).

Four weeks after the transplantation, human mitochondria and the photoreceptor cell antigen synaptophysin were immunostained and analyzed. In the non-transplanted group, recoverin means bipolar cells in the inner nuclear layer and cone photoreceptor cells in the outer nuclear layer. In the transplanted group, a 4- or 5-fold synaptophysin-positive cell layer was found to form a new outer nuclear layer, suggesting that the photoreceptor cells in the newly formed outer nuclear layer are in synaptic interaction with other intraretinal cells within the retinas of the transplanted mice.

*Microscopic field: Left. 200× magnification; the others 400× magnification.

BEST MODE

In accordance with an aspect thereof, the present invention pertains to a method for inducing stem cells to differentiate into retinal cells, comprising:
(a) culturing stem cell-derived retinal progenitor cells in a medium containing an IGF1R (insulin-like growth factor-1 receptor) activator, a BMP (bone morphogenetic protein) signaling pathway inhibitor, an FGF (fibroblast growth factor) signaling pathway activator, and a Wnt signalling pathway activator to differentiate them into neural retinal progenitor cells;
(b) culturing the neural retinal progenitor cells in a medium containing an IGF1R activator, a Wnt signaling pathway activator and an Shh (sonic hedgehog) signaling pathway activator to differentiate them into photoreceptor cell precursors; and
(c) culturing the photoreceptor cell precursors in a medium containing an IGF1R activator, a Wnt signaling pathway activator, an Shh signaling pathway activator and RA (retinoic acid) to differentiate them into retinal cells including photoreceptor cells.

In an embodiment of the method, when cultured in the presence of an IGF1R activator, a BMP signaling pathway inhibitor, an FGF signaling pathway activator and a Wnt signaling pathway activator, stem cell-derived retinal progenitor cells are induced to differentiate into neural retinal progenitor cells.

Further, the neural retinal progenitor cells are induced to differentiate into retinal cells under certain culture conditions (e.g., components making up the medium, contents of the components, culture periods, etc.). No particular limitations are imparted to the culture techniques and conditions as long as they are effective for differentiating the neural retinal progenitor cells into photoreceptor cell precursors, photoreceptor cells and other retinal cells.

As used herein, the term "stem cell" refers to a cell with pluripotency to give rise to all derivatives of the three primary germ layers (the endoderm, mesoderm and ectoderm) or one with multipotency to differentiate into mature cells closely related in tissue type and function.

As used herein, the term "animal" is intended to include humans, primates, cows, pigs, sheep, horses, dogs, mice, rats, and cats, humans being preferred.

As used herein, the term "embryonic stem cell" refers to a pluripotent cell derived from the inner cell mass of the blastocyst immediately before the nidation of a fertilized egg on the uterine wall, which can differentiate into any type of animal cell, and is intended in a broader sense to include stem cell-like cells such as embryoid bodies and induced pluripotent stem (iPS) cells.

The term "adult stem cell", as used herein, is intended to refer to a multipotent cell which is isolated from tissues and cultured ex vivo, and to include bone marrow stem cells, cord blood stem cells, amniotic fluid stem cells, fat stem cells, retinal stem cells, intraretinal Muller glial cells and neural stem cells.

The term "retina", as used herein, refers to light-sensitive tissue. The retina is the innermost (sensory) transparent coat in the eyeball and is directly relevant to vision. Just outside the neurosensory retina is the retinal pigment epithelium consisting of pigmented cells. In a broader sense, the retina includes the inner sensory coat and the outer retinal pigmented epithelium. The retina is located at the back of the eye and originates as outgrowths of the developing brain in embryonic development. The retina is like a five-layered cake, consisting of three nuclear layers with two network layers intercalated therebetween. The three nuclear layers are: the outermost nuclear layer consisting of photoreceptor cells; inner nuclear layer consisting of horizontal cells, bipolar cells, amacrine cells, and Muller glias; and the innermost retinal ganglion layer consisting of the nuclei of retinal ganglion cells. After passing through the cornea and the lens of the eye, light reaches the outer nuclear layer through the retinal ganglion layer and the inner layer in that order, producing neural impulses at photoreceptor cells. These neural impulses are transduced in a reverse direction. That is, when photoreceptor cells are stimulated by the neural impulses, nerve currents are transmitted to the inner nuclear layer and then into optic nerve fibers through the retinal ganglion cell layer.

As used therein, the term "progenitor cell" or "precursor" refers to a cell capable of asymmetric division. Asymmetric division refers to situations in which a progenitor cell or a precursor can, with a certain probability, either produce two further progenitor or precursor cells or differentiate, so that although they have undergone the same rounds of passages, the resulting cells may have different ages and properties.

The term "retinal progenitor cell", as used herein, is intended to refer to a multipotent progenitor cell which can differentiate into cells present in the retina and retinal pigmented epithelial cells. A retinal progenitor cell can, in general, undergo symmetric or asymmetric division and thus can either differentiate into various types of retinal cells or retinal pigmented epithelial cells, or produce two further retinal progenitor cells. Thus, it should be understood that the cells that are used in the culturing step to differentiate into retinal progenitor cells include various types of cells which were generated during differentiation from stem cells into retinal cells, as well as retinal progenitor cells. Retinal progenitor cells include neural retinal progenitor cells and retinal pigmented epithelial progenitor cells and are characterized by at least one, two or three markers selected from among Rax, Pax6, Chx10, Otx2, Sox2, Lhx2, Six3, Six6, and Mitf.

In connection with retinal development, as mentioned above, retinal progenitor cells are able to differentiate into various types of intraretinal cells (rod and cone photoreceptor cells, retinal ganglion cell, horizontal cells, bipolar cells, amacrine cells, Muller glial cells, etc.) and retinal pigmented epithelium, featuring positive expression of markers such as Crx, recoverin, rhodopsin, red/green opsin, blue opsin, peripherin2, PDE6B, SAG, Islet1/NF200, Prox1, PKC-a, Hu C/D, GFAP, and RPE65. However, the expression level and positive ratio of these markers become weaker in retinal progenitor cells than in mature retinal cells or retinal pigmented epithelium.

As used herein, the term "neural retinal progenitor cells" is intended to mean the retinal progenitor cells which favor neurons. That is, neural retinal progenitor cells are herein progenitor cells determined to differentiate into intraretinal neurons (rod and cone photoreceptor cells, retinal ganglion cells, horizontal cells, bipolar cells, amacrine cells, and Muller glial cells). A neural retinal progenitor cell can, in general, undergo symmetric or asymmetric division, either differentiating into various types of retinal cells or retinal pigmented epithelial cells, or producing two further retinal progenitor cells. Thus, it should be understood that the cells in the step of culturing that differentiate into neural retinal progenitor cells include various types of cells generated during the differentiation of stem cells into retinal cells as well as neural retinal progenitor cells. Neural retinal progenitor cells are characterized by expressing at least one, two or three markers selected from among Rax, Pax6, Chx10 and Crx.

In addition to expressing these markers, neural retinal progenitor cells may be characterized by the ability to express Crx, recoverin and rhodopsin, which are the markers of cells of the next differentiation stage, that is, photoreceptor cell precursors and photoreceptor cells. On the contrary, neural retinal progenitor cells are observed to have a decreased expression level of Otx2, Sox2, Lhx2, Six3, Six6 and Mitf, which are markers characteristic of retinal progenitor cells that manifest themselves in the previous differentiation stage.

As used herein, the term "retinal pigmented epithelial progenitor cell" is intended to refer to a differentiated retinal progenitor cell which favors retinal pigmented epithelium. Retinal pigmented epithelial progenitor cells are characterized by expressing one or more markers selected from among Mift and Pax6.

In a preferred embodiment, examples of the stem cells include, but are not limited to, bone marrow stem cells (BMSC), cord blood stem cells, amniotic fluid stem cells, fat stem cells, retinal stem cells (RSC), intraretinal Muller glial cells, embryonic stem cells (ESC), induced pluripotent stem cells (iPSC) and somatic cell nuclear transfer cells (SCNTC), with the greatest preference being for human ESC or iPSC. In an embodiment, iPSC as well as human ESC was successfully induced to differentiate into retinal cells including photoreceptor cells by the differentiation method of the present invention.

As used herein, the term "IGF1R (Insulin-like growth factor 1 receptor) activator" is used to refer to a substance which can bind to and activate IGF-1 (insulin-like growth factor-1) receptor (IGF1R), a member of the tyrosine kinase receptor family. Binding to IGF1R initiates intracellular signaling pathway: activated IGF1R interacts with insulin receptor substrates (IRS) which in turn acts as an activator of two pathways: one consisting of PI3k, Akt and mTOR; the other consisting of Raf, MEK and ERK (Ryan & Goss, Oncologist. 2008; 13: 16-24). IGF-1 and IGF-2 fall within the range of the IGF1R activator useful in the present invention. IGF-1, having a molecular structure similar to insulin, is implicated in cell growth, cell proliferation, differentiation, and cell death.

As long as it activates IGF1R, any IGF1R activator may be used without limitation in an embodiment of the present invention. Preferred is IGF-1 or IGF-2, with a higher preference for IGF-1.

In a preferred embodiment, the medium used for differentiating retinal progenitor cells into neural retinal progenitor cells contains IGF1R in an amount of from 0.01 to 100 ng/ml, preferably in an amount of from 0.1 to 50 ng/ml, more preferably in an amount of from 1 to 20 ng/ml and most preferably in an amount of 10 ng/ml.

The term "BMP (bone morphogenetic protein) signaling pathway inhibitor", as used herein, means a group of substances capable of inhibiting BMP signaling pathway. BMPs belong to a group of growth factors called TGF-β (transforming growth factor-β) superfamily and are involved in early-prenatal differentiation, prenatal tissue formation, and homeostasis of adult tissues. The level of BMP plays a critical role in the formation of the dorsoventral axis particularly in the early prenatal stage when the embryo is being developed. In addition, the inhibition of BMP is essential for the formation of neurons for both vertebrates and invertebrates in the prenatal stage. Extracellular secreted BMPs bind to Type I and Type II serine/threonine kinase receptors, initiating BMP signaling pathway. When activated, a type II receptor recruits and phosphorylates a type I receptor. The type I receptor then phosphorylates the intracellular substrate receptor-regulated Smad (R-Smad), mediating the BMP signal transduction pathway. Among R-Smads are Smad-1, 2, 3, 5 and 8. The phosphorylated R-Smads can now bind the common partner Smad (Co-Smad) Smad-4. R-SMAD/co-SMAD complexes migrate into and accumulate in the nucleus where they act as transcription factors and participate in the regulation of target gene expression (Yamamoto & Oelgeschlager, Naturwissenschaften. 2004; 91: 519-34). A BMP signaling pathway inhibitor refers to a substance which blocks the binding of extracellular BMP to cell-surface receptors. Examples of BMP signal pathway inhibitors include noggin, chordin, twisted gastrulation (Tsg), cerberus, coco, gremlin, PRDC (a protein related to DAN and Cerberus), DAN (a differential screening-selected gene aberrative in neuroblastoma), dante, follistatin, USAG-1 (uterine sensitization-associated gene 1), dorsomorphin and sclerostin. By inhibiting BMP signal transduction, noggin plays a key role in neural induction and in ventralizing dorsal neuroectoderm or mesoderm. Also, acting as an antagonist of the BMPs BMP-2, BMP-4 and BMP-7, noggin blocks these from binding to their receptors (Yanagita, Cytokine Growth Factor Rev. 2005; 16: 309-17).

So long as it inhibits BMP signal transduction, any BMP signaling pathway inhibitor may be employed in a preferred embodiment of the present invention. Preferred are noggin, chordin, twisted gastrulation (Tsg), cerberus, coco, gremlin, PRDC, DAN, dante, follistatin, USAG-1 (uterine sensitization-associated gene 1), dorsomorphin and sclerostin, with noggin being most preferred.

In a preferred embodiment, the medium useful for inducing the retinal progenitor cells to differentiate into neural retinal progenitor cells contains the BMP signaling pathway inhibitor in an amount of from 0.01 to 100 ng/ml, preferably in an amount of from 0.1 to 50 ng/ml, more preferably in an amount of from 0.5 to 20 ng/ml, and most preferably in an amount of 10 ng/ml.

As used herein, the term "FGF (fibroblast growth factor) signaling pathway activator" refers to a multifunctional factor involved in mitogenesis including cell proliferation and cell differentiation, angiogenesis, bone morphogenesis and neural induction. Twenty two members of the FGF family have been identified, so far. There are four members of the FGF receptor family. Alternative mRNA splicing gives rise to variants of the FGF receptors. Each receptor binds to a specific subset of the FGFs. The activated FGFR mediates the signal through Ras/Raf/MeK pathway to MAP kinase which can now migrate into and accumulate in the nucleus where it acts as a transcription factor and participates in the regulation of expression of the target gene (Bottcher & Niehrs, Endocr Rev. 2005; 26: 63-77). Of the FGF family, FGF2, also known as basic FGF (bFGF), binds mainly to FGFR 1b, FGFR 1c, FGFR 2c, FGFR 3c, and FGFR 4Δ and strongly activates FGFR 1c and FGFR 3c inter alia. Activators of FGFR 1c and FGFR 3c as well as FGF1, FGF4, FGF8, FGF9, FGF17 and FGF19 may be used as substitutes for FGF2.

So long as it stimulates FGF signal transduction, any FGF signaling pathway activator may be used without limitation in a preferred embodiment of the present invention. Preferred is an FGFR 1c or FGFR 3c activator, FGF1, FGF2, FGF4, FGF8, FGF9, FGF17 or FGF19, with FGF2 being the most preferred.

In a preferred embodiment, the medium useful for inducing the retinal progenitor cells to differentiate into neural retinal progenitor cells contains the FGF signaling pathway activator in an amount of from 0.01 to 100 ng/ml, preferably in an amount of from 0.1 to 50 ng/ml, more preferably in an amount of from 1 to 20 ng/ml, and most preferably in an amount of 5 ng/ml.

The term "Wnt signaling pathway activator", as used herein, is intended to refer to a substance activating the Wnt signaling pathway which has been found to regulate various processes during embryogenesis, including cell-fate determination, reconstruction of organization, polarity, morphology, adhesion and growth, and the maintenance and proliferation of undifferentiated cells (Logan & Nusse, Annu Rev Cell Dev Biol. 2004; 20: 781-810). As long as it transduces Wnt-mediated or beta-catenin-mediated signals, any activator may be included within the Wnt signaling pathway. The Wnt signaling pathway is a series of processes that are initiated by the binding of the trigger Wnt to its receptor or mediated by the stabilization of the downstream factor β-catenin. The following is a description of how to activate Wnt signaling pathway.

1) By adding a Wnt protein: Wnt, a first trigger of the Wnt signaling pathway, is a family of secreted glycoproteins. 19 Wnts have been identified: Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, and Wnt16b.

2) By increasing the level of β-catenin: most cells respond to Wnt signaling pathway by an increase in the level of β-catenin. That is, an increase in dephosphorylated β-catenin level or the stabilization of β-catenin means the translocation of β-catenin into the nucleus.

3) By phosphorylation of disheveled or phosphorylation of a Wnt-associated receptor, LRP tail.

4) By using GSK3 (glycogen synthase kinase 3) inhibitors: lithium (Li), LiCl, bivalent Zn, BIO (6-bromoindirubin-3' oxime), SB216763, SB415286, QS11 hydrate, TWS119, Kenpaullone, alsterpaullone, indirubin-3'-oxime, TDZD-8, and Ro 31-8220 methanesulfonate salt.

5) By blocking negative regulators of Wnt signaling pathway, such as Axin and APC, or by using RNAi.

6) With activators of the Wnt pathway, such as norrin and R-spondin2: Norrin binds to Frizzled4 receptor while R-spondin2 interacts with Frizzled8 and LRP6.

7) By gene transfer, including transfection: one can activate Wnt signaling pathway using either Wnt overexpression constructs or β-catenin overexpression constructs.

In a preferred embodiment, the Wnt signaling pathway activators may be employed without limitation. Preferred are Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; substances increasing β-catenin levels; GSK3 inhibitors such as lithium, LiCl, bivalent zinc, BIO, SB216763, SB415286, CHIR99021, QS11 hydrate, TWS119, Kenpaullone, alsterpaullone, indirubin-3'-oxime, TDZD-8 and Ro 31-8220 methanesulfonate salt; Axin inhibitors, APC inhibitors, norrin and R-spondin 2, and the most preferred are Wnt3a, Wnt1, Wnt5a, Wnt11, norrin, LiCl, BIO and SB415286.

In a preferred embodiment of the present invention, the medium useful for inducing the retinal progenitor cells to differentiate into neural retinal progenitor cells contains the Wnt signaling pathway activator except for LiCl, BIO and SB415286 in an amount of from 0.01 to 500 ng/ml, preferably in an amount of from 0.1 to 200 ng/ml, and more preferably in an amount of from 1 to 100 ng/ml. Among the Wnt signaling pathway activators, LiCl is used in the medium in an amount of 0.1 to 50 mM, preferably in an amount of 0.5 to 10 mM, and more preferably in an amount of 1 to 10 mM; BIO is used in an amount of 0.1 to 50 μM, preferably in an amount of 0.1 to 10 μM, and more preferably in an amount of 0.5 to 5 μM; SB415286 is used in an amount of 0.1 to 500 μM, preferably in an amount of 1 to 100 μM, and more preferably in an amount of 5 to 50 μM. In a modification of the embodiment, the medium may contain 50 ng/ml of Wnt3a or Wnt1; 50 or 100 ng/ml of Wnt5a and Wnt11; 50 ng/ml of norrin; 2.5 or 5 mM of LiCl; 2 μM of BIO, or 30 μM of SB415286. According to this embodiment, when a GSK3 inhibitor and norrin as well as Wnt proteins were used, the method of the present invention was successfully conducted, thereby achieving the desired differentiation. Therefore, the Wnt signaling pathway activators were found to play an important role in the differentiation into retinal cells.

In a preferred embodiment, the retinal progenitor cells are cultured for one day or longer, preferably for 1 to 30 days, more preferably for 1 to 10 days and most preferably for 5 days in the medium for inducing differentiation into neural retinal progenitor cells.

In a preferred embodiment, the culturing step for inducing the retinal progenitor cells to differentiate into neural retinal progenitor cells may further comprise determining whether the differentiated cells are neural retinal progenitor cells or not. Thus, the time period for this culturing may be adjusted to further include the time period required to carry out this determination.

In order to determine whether the retinal progenitor cells differentiated into neural retinal progenitor cells or not, mRNAs or proteins specific for neural retinal progenitor cells may be analyzed for expression level.

In a preferred embodiment, Rax, Pax6, Chx10 and Crx are among the markers characteristic of the neural retinal progenitor cells.

So long as it is well known in the art, any technique for analyzing specific genes at an mRNA level may be used in the present invention without limitations. Preferred are reverse transcriptase PCR (RT-PCR), competitive RT-PCR, real-time PCR, Rnase Protection Assay, Northern blotting and DNA chip assay.

Well-known techniques for analyzing specific genes at a protein level may be used in the present invention without limitation. Preferred are Western blotting, ELISA, radioimmunoassay, radioimmunodiffusion, Ouchterlony immunodiffusion, rocket immunoelectrophoresis, immunohistostaining, immunoprecipitation assay, complement fixation assay, FACS, and protein chip assay.

Compared to the pre-differentiative retinal progenitor cells, the post-differentiative neural retinal progenitor cells show at least one of the following features: (i) an increased expression level of Rax; (ii) an increased expression level of Pax6; (iii) an increased expression level of Chx10; (iv) a decreased expression level of Otx2; (v) a decreased expression level of Sox2; (vi) a decreased expression level of nestin; (vii) a decreased expression level of Ki67; (viii) an increased expression level of Crx; (ix) an increased expression level of recoverin; (x) an increased expression level of rhodopsin; (xi) an increased expression level of peripherin2; and (xii) a decreased expression level of Mitf.

An increase or decrease in the expression levels of the genes may be identified using antibodies to the proteins encoded by the genes or using methods well known to those skilled in the art, such as RT-PCR. As they show more of the features, the differentiated cells are defined as being closer to the neural retinal progenitor cells. The neural retinal progenitor cells differentiated according to the present invention show at least two of the features, preferably at least three, and more preferably at least five. Preferably, more than approximately 40%, 60%, 80%, 90%, 95% or 98% of the population of the cells after differentiation have the desired features. Higher ratios are more preferable.

In an embodiment of the method, when cultured in the presence of an IGF1R activator, a Wnt signaling pathway activator and an Shh (sonic hedgehog) signaling pathway activator, the neural retinal progenitor cells are induced to differentiate into photoreceptor cell precursors.

Furthermore, the photoreceptor cell precursors are induced to differentiate into retinal cells under certain culture conditions (e.g., components of the medium, contents of the components, culture periods, etc.). No particular limitations are imparted to the culture techniques and conditions as long as they effectively allow for the differentiation of the photoreceptor cell precursors into photoreceptor cells and other retinal cells as follows.

Examples of the stem cell useful in a preferred embodiment of the present invention include, but are not limited to, bone marrow stem cells (BMSC), cord blood stem cells, amniotic fluid stem cells, fat stem cells, retinal stem cells (RSC), intraretinal Muller glial cells, embryonic stem cells (ESC), induced pluripotent stem cells (iPSC) and somatic cell nuclear transfer cells (SCNTC), with the greatest preference being for human ESC or iPSC. In an embodiment, iPSC as well as human ESC was successfully induced to differentiate into retinal cells including photoreceptor cells by the differentiation method of the present invention.

As used herein, the term "photoreceptor cell precursor" means a precursor favoring differentiation into a photoreceptor cell, characterized by one or more markers selected from among Crx (rod and cone photoreceptor cell precursors) and Nrl (rod photoreceptor cell precursors). A photoreceptor cell precursor can, in general, undergo symmetric or asymmetric division, either differentiating into various types of retinal cells or retinal pigmented epithelial cells, or producing two further photoreceptor cell precursors. Therefore, it should be understood that the cells in the step of culturing to differentiate into photoreceptor cell precursors include various types of cells generated during differentiation from stem cells into retinal cells, as well as photoreceptor cell precursors. In addition to expressing the markers, the photoreceptor cell precursors may also be characterized by the ability to express at least one, two or three of recoverin, rhodopsin, peripherin2, and rom1, which are markers characteristic of differentiating photoreceptor cells.

In a preferred embodiment, any IGF1R activator that activates IGF1R may be used without limitations. Preferred is IGF-1 or IGF-2, with priority given to IGF-1.

In a preferred embodiment, the medium useful for inducing the neural retinal progenitor cells to differentiate into photoreceptor cell precursors contains the IGF1R activator in an amount of from 0.01 to 100 ng/ml, preferably in an amount of from 0.1 to 50 ng/ml, more preferably in an amount of from 1 to 20 ng/ml, and most preferably in an amount of 10 ng/ml.

So long as it activates Wnt signaling pathway, any Wnt signaling pathway activator may be used in the present invention. Examples of the Wnt signaling pathway activators useful in the present invention include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; substances increasing β-catenin levels; GSK3 inhibitors such as lithium, LiCl, bivalent zinc, BIO, SB216763, SB415286, CHIR99021, QS11 hydrate, TWS119, Kenpaullone, alsterpaullone, indirubin-3'-oxime, TDZD-8 and Ro 31-8220 methanesulfonate salt; Axin inhibitors, APC inhibitors, norrin and R-spondin 2, with preference for Wnt3a, Wnt1, Wnt5a, Wnt11, norrin, LiCl, BIO and SB415286.

In a preferred embodiment, the medium useful for inducing the neural retinal progenitor cells to differentiate into photoreceptor cell precursors contains the Wnt signaling pathway activator except for LiCl, BIO and SB415286 in an amount of from 0.01 to 500 ng/ml, preferably in an amount of from 0.1 to 200 ng/ml, and more preferably in an amount of from 1 to 100 ng/ml. Among the Wnt signaling pathway activators, LiCl is used in the medium in an amount of 0.1 to 50 mM, preferably in an amount of 0.5 to 10 mM, and more preferably in an amount of 1 to 10 mM; BIO is used in an amount of 0.1 to 50 µM, preferably in an amount of 1 to 10 µM, and more preferably in an amount of 0.5 to 5 µM; SB415286 is used in an amount of 0.1 to 500 µM, preferably in an amount of 1 to 100 µM, and more preferably in an amount of 5 to 50 µM. In a modification of the embodiment, the medium may contain 50 ng/ml of Wnt3a or Wnt1; 50 or 100 ng/ml of Wnt5a or Wnt11; 50 ng/ml of norrin, 2.5 or 5 mM of LiCl, 2 µM of BIO, or 30 µM of SB415286. According to this embodiment, when a GSK3 inhibitor and norrin as well as Wnt proteins were used, the method of the present invention was successfully conducted, thereby achieving the desired differentiation.

Therefore, the Wnt signaling pathway activators were found to play an important role in differentiation into retinal cells.

As used herein, the term "Shh signaling pathway activator" is intended to refer to a substance activating the Shh signaling pathway which is associated with the regulation of various processes during embryogenesis, including cell-fate determination, reconstruction of organization, polarity, morphology, proliferation, and differentiation (Bertrand & Dahmane, Trends Cell Biol. 2006; 16: 597-605). Sonic hedgehog (Shh) is one of three proteins in the mammalian signaling pathway family called hedgehog, the others being Indian hedgehog (Ihh) and desert hedgehog (Dhh). The Shh signaling pathway involves two transmembrane proteins, Ptc (Patched) and Smo (Smoothened). In the absence of Shh, Ptc's interacts with and inhibits Smo. When Shh binds to Ptc, Ptc's interactions with Smo are altered such that Smo is no longer inhibited, leading to Ci/Gli protein entering the nucleus and acting as a transcriptional activator for target genes. No particular limitations are imparted to the Shh signaling pathway activator if it enhances Shh-mediated signaling pathway. Examples of the Shh signaling pathway activators useful in the present invention include proteins belonging to the hedgehog family (e.g., Shh), inhibitors of Ptc's interaction with Smo, Smo receptor activators, Shh receptor activators (e.g. Hg—Ag, purmorphamine, etc.), substances increasing Ci/Gli family levels, inhibitors of the intracellular degradation of Ci/Gli factors, and Shh overexpression constructs or Ci/Gli overexpression constructs resulting from transfection.

So long as it activates Shh signaling pathway, any Shh signaling pathway activator may be used in the present invention. Preferred are Shh, Smo receptor activators, inhibitors of Ptc's interaction with Smo, substances increasing Ci/Gli family levels, inhibitors of the intracellular degradation of Ci/Gli factors, and Shh receptor effects such as Hg—Ag and purmorphamine, the most preferred being Shh or purmorphamine.

In a preferred embodiment, the medium useful for inducing the neural retinal progenitor cells to differentiate into photoreceptor cell precursors contains the Shh signaling pathway activator in an amount of from 0.1 to 5,000 ng/ml, preferably in an amount of from 1 to 2,500 ng/ml, more preferably in an amount of from 10 to 1,000 ng/ml, and most preferably in an amount of 250 ng/ml. In an embodiment of the present invention, the medium contains Shh in an amount of 250 ng/ml or purmorphamine in an amount of 1 µM.

In a preferred embodiment, the neural retinal progenitor cells are cultured for one day or longer, preferably for 1 to 30 days, more preferably for 1 to 10 days and most preferably for 3 days in the medium for inducing differentiation into photoreceptor cell precursors.

In a preferred embodiment, the culturing step for inducing the neural retinal progenitor cells to differentiate into photoreceptor cell precursors may further comprise determining whether the differentiated cells are photoreceptor cell precursors or not. Thus, the time period for this culturing may be adjusted to further include the time period required to carry out this determination.

In order to determine whether the neural retinal progenitor cells successfully differentiated into photoreceptor cell precursors or not, the expression level of mRNAs or proteins specific for photoreceptor cell precursors may be analyzed.

In a preferred embodiment, Crx and Nrl are among the markers characteristic of the photoreceptor cell precursors.

So long as it is well known in the art, any technique for analyzing specific genes at an mRNA level may be used in the present invention without limitation. Preferred are reverse transcriptase PCR (RT-PCR), competitive RT-PCR, real-time PCR, Rnase Protection Assay, Northern blotting and the DNA chip assay.

Well-known techniques for analyzing specific genes at the protein level may be used in the present invention without limitations. Preferred are Western blotting, ELISA, radioimmunoassay, radioimmunodiffusion, Ouchterlony immunodiffusion, rocket immunoelectrophoresis, immunohistostaining, immunoprecipitation assay, complement fixation assay, FACS, and protein chip assay.

Compared to the pre-differentiated neural retinal progenitor cells, the post-differentiated photoreceptor cell precursors show at least one of the following features: (i) a decreased expression level of Pax6; (ii) a decreased expression level of Chx10; (iii) a decreased expression level of Sox2; (iv) an increased expression level of Ki67; (vi) a decreased expression level of Crx; (vi) an increased expression level of rhodopsin; and (vii) an increased expression level of peripherin2.

An increase or decrease in the expression level of the genes may be identified using antibodies to the proteins encoded by the genes or using methods well known to those skilled in the art, such as RT-PCR. As they show more of the features, the differentiated cells are defined as being closer to photoreceptor cell precursors. The photoreceptor cell precursors differentiated according to the present invention show at least two of the features, preferably at least three, and more preferably at least five. Preferably, more than approximately 40%, 60%, 80%, 90%, 95% or 98% of the population of the cells after the differentiation have the desired features. Higher ratios are more preferable.

In an embodiment of the method, when cultured in the presence of an IGF1R activator, a Wnt signaling pathway activator, an Shh signaling pathway activator and RA (retinoic acid), the photoreceptor cell precursors are induced to differentiate into photoreceptor cells.

Further, the photoreceptor cells are induced to differentiate into retinal cells under certain culture conditions (e.g., components of the medium, contents of the components, culture periods, etc.). No particular limitations are put on the culture techniques and conditions as long as they effectively differentiate the photoreceptor cells into other retinal cells as follows.

Examples of the stem cells useful in a preferred embodiment of the present invention include, but are not limited to, bone marrow stem cells (BMSC), cord blood stem cells, amniotic fluid stem cells, fat stem cells, retinal stem cells (RSC), intraretinal Muller glial cells, embryonic stem cells (ESC), induced pluipotent stem cells (iPSC) and somatic cell nuclear transfer cells (SCNTC), with the greatest preference being for human ESC or iPSC. In an embodiment, iPSC as well as human ESC was successfully induced to differentiate into retinal cells including photoreceptor cells by the differentiation method of the present invention.

As used herein, the term "photoreceptor cell" refers to a specialized type of neuron found in the eye's retina that is capable of phototransduction and allowing shapes and colors to be recognized: when light reaches the retina through the cornea and the lens, the photoreceptor cell converts the light energy into electric energy which is then transmitted into the brain. There are two main types of photoreceptor cells: rods and cones, which are adapted for low light and bright light, respectively. Cone cells gradually become denser towards the center of the retina, that is, the yellow spot, and function to perceive images and colors while rod cells are distributed predominantly at the periphery of the retina, allowing the perception of images and light. Photoreceptor cells are characterized by the ability to express at least one, two or three markers selected from among recoverin (rod photoreceptor cells, cone photoreceptor cells), rhodopsin (rod photoreceptor cells), peripherin2 (rod photoreceptor cells), rom1 (rod photoreceptor cells, cone photoreceptor cells), Pde6b (rod photoreceptor cells), arrestin sag (rod photoreceptor cells), phosducin (rod photoreceptor cells, cone photoreceptor cells), synaptophysin (rod photoreceptor cells, cone photoreceptor cells), red/green opsin (cone photoreceptor cells), and blue opsin (cone photoreceptor cells).

In a preferred embodiment, any IGF1R activator that activates IGF1R may be used without limitation. Preferred is IGF-1 or IGF-2, with priority given to IGF-1.

In a preferred embodiment, the medium useful for inducing the photoreceptor cell precursors to differentiate into photoreceptor cells contains the IGF1R activator in an amount of from 0.01 to 100 ng/ml, preferably in an amount of from 0.1 to 50 ng/ml, more preferably in an amount of from 1 to 20 ng/ml, and most preferably in an amount of 10 ng/ml.

So long as it activates Wnt signaling pathway, any Wnt signaling pathway activator may be used in the present invention. Examples of the Wnt signaling pathway activators useful in the present invention include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; substances increasing β-catenin levels; GSK3 inhibitors such as lithium, LiCl, bivalent zinc, BIO, SB216763, SB415286, CHIR99021, QS11 hydrate, TWS119, Kenpaullone, alsterpaullone, indirubin-3'-oxime, TDZD-8 and Ro 31-8220 methanesulfonate salt; Axin inhibitors, APC inhibitors, norrin and R-spondin 2, with preference for Wnt3a, Wnt1, Wnt5a, Wnt11, norrin, LiCl, BIO and SB415286.

In a preferred embodiment, the medium useful for inducing the photoreceptor cell precursors to differentiate into photoreceptor cells contains the Wnt signaling pathway activator except for LiCl, BIO and SB415286 in an amount of from 0.01 to 500 ng/ml, preferably in an amount of from 0.1 to 200 ng/ml, and more preferably in an amount of from 1 to 100 ng/ml. Among the Wnt signaling pathway activators, LiCl is used in the medium in an amount of 0.1 to 50 mM, preferably in an amount of 0.5 to 10 mM, and more preferably in an amount of 1 to 10 mM; BIO is used in an amount of 0.1 to 50 µM, preferably in an amount of 0.1 to 10 µM, and more preferably in an amount of 0.5 to 5 µM; SB415286 is used in an amount of 0.1 to 500 µM, preferably in an amount of 1 to 100 µM, and more preferably in an amount of 5 to 50 µM. In a modification of the embodiment, the medium may contain 50 ng/ml of Wnt3a or Wnt1; 50 or 100 ng/ml of Wnt5a or Wnt11; 50 ng/ml of norrin, 2.5 or 5 mM of LiCl, 2 µM of BIO, or 30 µM of SB415286. According to this embodiment, when a GSK3 inhibitor and norrin as well as Wnt proteins were used, the method of the present invention was successfully conducted, thereby achieving the desired differentiation. Therefore, the Wnt signaling pathway activators were found to play an important role in differentiation into retinal cells.

So long as it activates Shh signaling pathway, any Shh signaling pathway activator may be used in the present invention. Preferred are Shh, Smo receptor activators, inhibitors of Ptc's interaction with Smo, substances increasing Ci/Gli family levels, inhibitors of the intracellular degradation of Ci/Gli factors, and Shh receptor effects such as Hg—Ag and purmorphamine, the most preferred being Shh or purmorphamine.

In a preferred embodiment, the medium useful for inducing the neural retinal progenitor cells to differentiate into photoreceptor cell precursors contains the Shh signaling pathway activator in an amount of from 0.1 to 5,000 ng/ml, preferably in an amount of from 1 to 2,500 ng/ml, more preferably in an amount of from 10 to 1,000 ng/ml, and most preferably in an amount of 250 ng/ml. In an embodiment of the present invention, the medium contains Shh in an amount of 250 ng/ml or purmorphamine in an amount of 1 µM.

As used herein, the term "RA (retinoic acid)" refers to a metabolite of vitamin A, which is a lipophilic molecule involved in various biological processes including cell proliferation, differentiation and death by regulating gene transcription. There are two types of RA: all-trans retinoic acid and 9-cis retinoic acid. RA is translocated into the nucleus where it binds to RARs (retinoic acid receptors) and RXR (retinoid X receptors) respectively and participates in the regulation of target gene transcription.

According to a preferred embodiment of the present invention, RA contained in the medium for inducing the photoreceptor cell precursors to differentiate into photoreceptor cells may be the trans-type or cis-type and may be used in a concentration of from 0.5 to 10,000 nM, preferably a concentration of from 5 to 5,000 nM, more preferably a concentration of from 50 to 2,000 nM, and most preferably in a concentration of 500 nM.

In a preferred embodiment, the photoreceptor cell precursors are cultured for one day or longer, preferably for 1 to 60 days, more preferably for 1 to 30 days and most preferably for 8 to 15 days in the medium for inducing differentiation into photoreceptor cells.

In a preferred embodiment, the culturing step for inducing the photoreceptor cell precursors to differentiate into photoreceptor cells may further comprise determining whether the differentiated cells are photoreceptor cells or not. Thus, the time period for this culturing may be adjusted to further include the time period required to carry out this determination.

In order to determine whether the photoreceptor cell precursors successfully differentiated into photoreceptor cells or not, the expression level of mRNAs or proteins specific for photoreceptor cells may be analyzed.

According to a preferred embodiment, recoverin, rhodopsin, peripherin2, rom1, Pde6b, arrestin sag, phosducin, synaptophysin, red/green opsin and blue opsin are among the markers characteristic of the photoreceptor cells.

Any technique for analyzing specific genes at an mRNA level that is well known in the art may be used in the present invention without limitation. Preferred are reverse transcriptase PCR (RT-PCR), competitive RT-PCR, real-time PCR, Rnase Protection Assay, Northern blotting and DNA chip assay.

Well-known techniques for analyzing specific genes at the protein level may be used in the present invention without limitation. Preferred are Western blotting, ELISA, radioimmunoassay, radioimmunodiffusion, Ouchterlony immunodiffusion, rocket immunoelectrophoresis, immunohistostaining, immunoprecipitation assay, complement fixation assay, FACS, and protein chip assay.

Compared to the pre-differentiated photoreceptor cell precursors, the post-differentiated photoreceptor cells show at least one of the following features: (i) an increased expression level of Pax6; (ii) an increased expression level of Sox2; (iii) a decreased expression level of nestin; (iv) a decreased expression level of Ki67; (v) a decreased expression level of Crx; (vi) an increased expression level of recoverin; (vii) an increased expression level of rhodopsin; and (vii) an increased expression level of peripherin2.

An increase or decrease in the expression level of the genes may be identified using antibodies to the proteins encoded by the genes or using methods well known to those skilled in the art, such as RT-PCR. As they show more of the features, the differentiated cells are defined as being closer to photoreceptor cell precursors. The photoreceptor cell precursors differentiated according to the present invention show at least two of the features, preferably at least three, and more preferably at least five. Preferably, more than approximately 40%, 60%, 80%, 90%, 95% or 98% of the population of the cells after the differentiation have the desired features. Higher ratios are more preferable.

In accordance with an embodiment, the method of the present invention may further comprise differentiating stem cells into retinal progenitor cells. In this context, any technique that is well known in the art or allows the production of retinal progenitor cells may be employed.

Preferably, the retinal progenitor cells may be obtained by: (a') culturing stem cells in a medium containing an IGF1R activator, a Wnt signaling pathway inhibitor and a BMP signaling pathway inhibitor to differentiate them into eye field precursors in the form of floating aggregates; and
(b') culturing the eye field precursors in the form of floating aggregates in a medium containing an IGF1R activator, a Wnt signaling pathway inhibitor, a BMP signaling pathway inhibitor and an FGF signaling pathway activator to differentiate them into retinal progenitor cells.

In a preferred embodiment, when cultured, the floating aggregates of eye field precursors may be grown adhering to a plate. Any cell-adhering plate well known in the art may be employed. Preferably, it is coated with an extracellular matrix, such as poly-D-lysine, laminin, poly-L-lysine, matrigel, agar, polyornithine, gelatin, collagen, fibronectin or vitronectin. Most preferred is a plate coated with poly-D-lysine/laminin.

The cell population per floating aggregate which adheres to the plate is the one that is the most highly efficient. Preferably, a floating aggregate consists of 200-400 cells.

Examples of the stem cells useful in a preferred embodiment of the present invention include, but are not limited to, bone marrow stem cells (BMSC), cord blood stem cells, amniotic fluid stem cells, fat stem cells, retinal stem cells (RSC), intraretinal Muller glial cells, embryonic stem cells (ESC), induced pluipotent stem cells (iPSC) and somatic cell nuclear transfer cells (SCNTC), with the greatest preference being for human ESC or iPSC. In an embodiment, iPSC as well as human ESC was successfully induced to differentiate into retinal cells including photoreceptor cells by the differentiation method of the present invention.

As used herein, the term "eye field precursor" refers to a cell expressing a marker (eye field transcription factors; Zuber, et al., Development, 2003; 130: 5155-67) found in a progenitor for the eye field of the forebrain neural plate. The eye field precursors are characterized by at least one, two or three markers selected from among Six3, Rax, Pax6, Otx2, Lhx2, and Six6.

As used herein, the term "floating aggregate" refers to a cell mass floating in a medium which is generated when a floc of stem cells is cultured for at least one day in a non-adhesive plate without feeding mouse embryonic fibroblasts and sera. Depending on the composition of the medium supplied, the eye field precursors may express eye field transcription factors.

As used herein, the term "Wnt signaling pathway inhibitor" is intended to refer to a factor which interrupts interaction between the extracellular Wnt protein and the membrane protein Frizzled receptor or LRP or inhibits intracellular Wnt-mediated signal transduction (Kawano & Kypta, J Cell Sci. 2003; 116: 2627-34). So long as it inhibits Wnt-mediated signal transduction, any Wnt signaling pathway inhibitor may be used in the present invention. Examples of the Wnt signaling pathway inhibitors useful in the present invention include the Dkk (Dickkopf) family (Dkk-1, Dkk-2, Dkk-3 and Dkk-4), which are Wnt antagonists capable of interacting with the co-receptor LRP, Wise, the sFRP (secreted Frizzled-related protein) family, which functions as Wnt antagonists binding to Wnt receptors, a Frizzled-CRD domain, WIF-1 (Wnt inhibitory factor-1), IWP-2, IWP-3, IWP-4, cerberus, Wnt antibodies, dominant negative Wnt proteins, overexpression of Axin, overexpression of GSK (glycogen synthase kinase), dominant negative TCF, dominant negative disheveled and casein kinase inhibitors (CKI-7, D4476 etc.), with preference for Dkk-1.

Wnt signal transduction may be inhibited by suppressing each component involved in the Wnt pathway with for example RNAi, in addition to the Wnt signaling pathway inhibitor.

In a preferred embodiment, IGF-1 or IGF-2 may be used as an IFG1R activator, with priority given to IGF-2. Examples of the BMP signal pathway inhibitor include noggin, chordin, twisted gastrulation (Tsg), cerberus, coco, gremlin, PRDC, DAN, dante, follistatin, USAG-1, dorsomorphin and sclerostin, with preference for noggin. As the FGF signaling pathway activator, a factor activating FGRR1c or FGFR3c, FGF1, FGF2, FGF4, FGF8, FGF9, FGF17 or FGF19 may be used, with FGF2 being preferred. Examples of the Wnt signaling pathway activator useful in the present invention include Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; substances increasing β-catenin levels; GSK3 inhibitors such as lithium, LiCl, bivalent zinc, BIO, SB216763, SB415286, CHIR99021, QS11 hydrate, TWS119, Kenpaullone, alsterpaullone, indirubin-3'-oxime, TDZD-8 and Ro 31-8220 methanesulfonate salt; Axin inhibitors, APC inhibitors, norrin and R-spondin 2, with preference for Wnt3a, Wnt1, Wnt5a, Wnt11, norrin, LiCl, BIO and SB415286. Examples of the Shh signaling pathway activator useful in the present invention include Shh, Smo receptor activators, inhibitors of the interaction of Ptc with Smo, substances increasing Ci/Gli family levels, inhibitors of the intracellular degradation of Ci/Gli factors, and Shh receptor effects such as Hg—Ag and purmorphamine, the most preferred being Shh or purmorphamine. The RA used in the present invention can be a trans- or cis-type retinoic acid.

As for the period of time for culturing after differentiation starts, it is preferably given 1-30 days for step (a'), 5-15 days for step (b'), 1-30 days for step (a), 1-30 days for step (b), and 1-60 days for step (c), and most preferably 4 days for step (a'), 9 days for step (b'), 5 days for step (a), 3 days for step (b), and 8-15 days for step (c). In a preferred embodiment, it takes as short as approximately 29 days to complete the differentiation of stem cells into retinal cells, allowing the method to be effectively applied to clinical treatment.

Differentiation into eye field precursors in step (a') may be accomplished by inducing and promoting the development of the forebrain during embryogenesis with the concomitant suppression of Wnt and BMP signaling pathways (Piccolo, et al., Nature, 1999; 397: 707-10). Therefore, the culture medium contains Dkk-1 as a Wnt signaling pathway inhibitor, noggin as a BMP inhibitor, and IGF-1 as an IGF1R activator functioning to promote the formation of the eye field in the forebrain. Kinds and medium levels of the Wnt signaling pathway inhibitor, the BMP inhibitor and the IGF1R activator are as defined above.

The medium useful in step (a') contains IGF-1 at a concentration of 0.01-100 ng/ml, Dkk-1 at a concentration of 0.01-

10,000 ng/ml and noggin at a concentration of 0.01-100 ng/ml, and most preferably IGF-1 at a concentration of 5 ng/ml, Dkk-1 at a concentration of 1 ng/ml, and noggin at a concentration of 1 ng/ml.

Any conventional medium for culturing stem cells may be used for inducing differentiation into eye field precursors in step (a'). Preferred is DMEM/F12 containing 10% knockout serum replacement, 1 mM L-glutamine, 0.1 mM non-essential amino acids, 0.1 mM mercaptoethanol, and 1% B27 supplement.

Differentiation into retinal progenitor cells in step (b') may be conducted in a medium containing an FGF signaling pathway activator, preferably FGF2, in combination with the factors of step (a'), that is, an IGF1R activator, a Wnt signaling pathway inhibitor and a BMP inhibitor. Kinds and medium levels of the Wnt signaling pathway inhibitor, the BMP inhibitor, the IGF1R activator and the FGF signaling pathway activator are as defined above.

The medium useful in step (b') contains IGF-1 at a concentration of 0.01-100 ng/ml, Dkk-1 at a concentration of 0.01-10,000 ng/ml, noggin at a concentration of 0.01-100 ng/ml and FGF2 at a concentration of 0.01-100 ng/ml and preferably IGF-1 at a concentration of 10 ng/ml, Dkk-1 at a concentration of 10 ng/ml, noggin at a concentration of 10 ng/ml and FGF2 at a concentration of 5 ng/ml.

The differentiation of the retinal progenitor cells of step (b') into neural retinal progenitor cells in step (a), must be conducted in the absence of Dkk-1, a Wnt signaling pathway inhibitor, for there to be a high level of Pax6 expressed (Pax6 is essential for the generation of neural retinal progenitor cells), and in a medium containing Wnt3a for promoting the Wnt pathway, noggin for converting ventral retinal pigmented epithelium into the neural retina in the development stage of optic vesicles and optic cups during embryogenesis, FGF2 for suppressing the expression of genes necessary for retinal pigmented epithelium and promoting the generation of neural retinal progenitor cells, and IGF-1 responsible for the antiapoptosis of photoreceptor cells.

The medium useful in step (a) contains IGF-1 in a concentration of 0.01-100 ng/ml, noggin in a concentration of 0.01-100 ng/ml, FGF2 in a concentration of 0.01-100 ng/ml, and Wnt3a in a concentration of 0.01-500 ng/ml and most preferably IGF-1 in a concentration of 10 ng/ml, noggin in a concentration of 10 ng/ml, FGF2 at a concentration of 5 ng/ml and Wnt3a at a concentration of 50 ng/ml.

Differentiation into photoreceptor cell precursors in step (b) is conducted in a medium which is free of both noggin and FGF2 that respectively inhibit Shh signaling pathway and Shh-induced rhodopsin expression, and which contains IGF-1 for proliferating rod photoreceptor cell precursors, Wnt3a for promoting the Wnt pathway, and Shh.

The medium useful in step (b) contains IGF-1 in a concentration of 0.01-100 ng/ml, Wnt3a at a concentration of 0.01-500 ng/ml and Shh at a concentration of 0.1-5,000 ng/ml and most preferably IGF-1 at a concentration of 10 ng/ml, Wnt3a at a concentration of 50 ng/ml and Shh at a concentration of 250 ng/ml.

Differentiation into photoreceptor cells in step (c) is conducted in a medium which contains RA (retinoic acid) for further promoting the differentiation in combination with IGF-1, Wnt3a and Shh.

The medium useful in step (c) contains IGF-1 in a concentration of 0.01-100 ng/ml, Wnt3a at a concentration of 0.01-500 ng/ml, Shh at a concentration of 0.01-5,000 ng/ml and RA at a concentration of 0.5-10,000 nM and most preferably IGF-1 at a concentration of 10 ng/ml, Wnt3a at a concentration of 50 ng/ml, Shh at a concentration of 250 ng/ml and RA at a concentration of 500 nM.

In steps (a) to (c), Wnt1, Wnt5a, Wnt11, norrin, LiCl, BIO or SB415286 may be used instead of Wnt3a while purmorphamine may substitute for Shh.

Any conventional medium for culturing embryonic stem cells may be used as a fundamental medium in steps (b'), (a), (b) and (c). Preferred is DMEM/F12 containing 1 mM L-glutamine, 0.1 mM non-essential amino acids, 0.1 mM mercaptoethanol, 1% B27 supplement and 1% N2 supplement.

In an embodiment of the present invention, the retinal cells differentiated according to the method of the present invention may include photoreceptor cells, retinal ganglion cells, horizontal cells, bipolar cells, amacrine cells, Muller glial cells, retinal pigmented epithelial progenitor cells and/or retinal pigmented epithelial cells, with photoreceptor cells constituting preferably more than 50% and most preferably more than 70% of the population of the cells.

According to an embodiment of the present invention, human embryonic stem cell lines H9 and H7 are induced to differentiate into photoreceptor cells by the following five steps. In the first step, human embryonic stem cells or human induce pluripotent stem cells are cultured for 4 days in a medium which is free of serum and FGF2 and contains IGF-1, Dkk-1 and noggin, so as to generate eye field precursors in the form of floating aggregates (Example 2). In the second step, the same medium as in the first step, but supplemented with FGF2, is used to induce the eye field precursors for 9 days to differentiate the precursors into retinal progenitor cells (Example 3). In the third step, the cells are cultured for 5 days in the same medium as in the second step, but free of Dkk-1 and supplemented with Wnt3a, to induce differentiation into neural retinal progenitor cells (Example 4). In the fourth step, Shh is added to the medium in which the cells are induced for three days to promote differentiation into photoreceptor cell precursors (Example 5). In the fifth step, the cells are cultured for 8 days or longer in the medium in the presence of RA to generate and mature photoreceptor cells (Example 6). The cells thus obtained are identified and analyzed for properties using immunochemical assay, RT-PCR and base sequencing (Example 7). The generated photoreceptor cells were transplanted into rd/SCID mice as immunodeficient retinal-degeneration models where they are evaluated for properties and clinical applicability (Example 8). As a result, the photoreceptor cells were found to be safely transplanted and engrafted into the mice and function properly. On the other hand, respective substitutes may be used instead of Wnt3a and Shh. In this context, the culturing processes are carried out for the same time period under the same conditions with the exception that 50 ng/ml of Wnt1; 50 or 100 ng/ml of Wnt5a or Wnt11; 50 ng/ml of norrin; 2.5 or 5 mM of LiCl; 2 μM of BIO; or 30 μM of SB415286 is used as a Wnt signaling pathway activator in substitution for Wnt3a and purmorphamine is used as a substitute for Shh. These substitutes, as a result, give rise to the differentiation and maturation of photoreceptor cells in a similar pattern to that obtained with Wnt3a and Shh (Example 9).

In addition, more than 70% of the human embryonic stem cells employed are successfully differentiated into photoreceptor cells by the method of the present invention, with a cell population 257-fold higher than that of the initial human embryonic stem cells. The resulting photoreceptor cells are found to express phosducin (49.8±2.2%), which participates in the regulation of visual phototransduction, and synaptophysin (43.0±2.0%), which is responsible for synaptic interactions with other intraretinal neurons, as well as the structural proteins recoverin (82.4±4.6%), rhodopsin (81.2±2.5%), peripherin2 (41.2±2.0%) and rom1 (76.0±4.6%). In addition to the photoreceptor cells, other retinal cells including retinal ganglion cells (6.0±0.6%), bipolar cells (5.7±1.7%), horizontal cells (7.1±0.6%), Muller glial cells (8.7±2.9%) and retinal pigmented epithelium (12.5±1.4%) are observed. The positive rates of these cells are almost identical to the composition ratios thereof within the human normal retina. After being transplanted into four-week-old rd/SCID mice in which photoreceptor cells have degenerated and completely disappeared, the cells are found to form a 4- or 5-ply photoreceptor layer within the retina of the mice, with the concomitant expression of phosducin and synaptophysin, indicating that the implanted cells participate in the construction of retinal neurons and light circuits in synaptic interaction with preexisting retinal cells. Accordingly, the human embryonic stem cells are successfully induced to differentiate perfectly into an increased population of mature photoreceptor cells at high efficiency by the method of the present invention.

The retinal progenitor cells differentiated in the second step (Example 3) express markers characteristic of eye field precursors as well as of themselves at a positive rate of 86.6±3.0% for Rax, 63.9 0.9% for Pax6, 76.4±2.0% for Otx2, 83.0±1.9% for Sox2, and 46.3±1.0% for Chx10. Mitf, a marker for retinal pigmented epithelial progenitor cells, and nestin, a marker for neural progenitor cells, are expressed at a positive rate of 17.2±0.4% and 65.7±2.7%, respectively (Table 1).

The neural retinal progenitor cells differentiated in the third step (Example 4) are observed to have modulated marker expression levels: there is an increase in the expression levels of the markers Pax6, Rax and Chx10 (all characteristic of both retinal progenitor cells and neural retinal progenitor cells), Crx (characteristic of photoreceptor cell precursors), recoverin (characteristic of universal photoreceptor cells), rhodopsin (characteristic of rod photoreceptor cells), and peripherin2 (characteristic of the outer segment of photoreceptor cells); also, there is a decrease in the expression level of Otx2 and Sox2 (characteristic of retinal progenitor cells), and nestin (characteristic of neural progenitor cells), (Ki67 indicative of cell proliferation) compared to the retinal progenitor cells of the previous step (Tables 1 and 3).

Also, the photoreceptor cell precursors resulting from the fourth step (Example 5) are observed to have modulated marker expression levels: there is a decrease in the expression level of Pax6 and Chx10 (each characteristic of both retinal progenitor cells and neural retinal progenitor cells), and Sox2 (characteristic of retinal progenitor cells); also, there is an increase in the expression level of K167 (indicative of cell proliferation), and rhodopsin and peripherin2 (both characteristic of photoreceptor cells) compared to the neural retinal progenitor cells of the previous step (Tables 1 and 3).

Modulation in marker expression levels is also detected in the photoreceptor cells differentiated in the fifth step (Example 6): there is an increase in the expression levels of Pax6 characteristic of both retinal progenitor cells and neural retinal progenitor cells, Sox2 characteristic of retinal progenitor cells, and recoverin, rhodopsin and peripherin2, all characteristic of photoreceptor cells; also, there is a decrease in the expression level of nestin characteristic of neural progenitor cells, Ki67 indicative of cell proliferation and Crx characteristic of photoreceptor cell precursors (Tables 1 and 3).

In accordance with another aspect thereof, the present invention provides the neural retinal progenitor cells generated according to the method of the present invention.

In accordance with a further aspect thereof, the present invention provides the photoreceptor cell precursors generated according to the method of the present invention.

In accordance with still a further aspect thereof, the present invention provides the photoreceptor cells generated according to the method of the present invention.

In accordance with still another aspect thereof, the present invention provides retinal cells comprising photoreceptor cells, retinal ganglion cells, horizontal cells, bipolar cells, amacrine cells, Muller glial cells, retinal pigmented epithelial progenitor cells or retinal pigmented epithelium, all generated according to the method of the present invention.

In accordance with yet another aspect thereof, the present invention provides a composition for treating retinal degeneration-related diseases, comprising the neural retinal progenitor cells differentiated according to the method of the present invention.

In accordance with yet a still further aspect thereof, the present invention provides a composition for treating retinal degeneration-related diseases, comprising the photoreceptor cell precursors differentiated according to the method of the present invention.

In accordance with yet still another aspect thereof, the present invention provides a composition for treating retinal degeneration-related diseases, comprising the photoreceptor cells differentiated according to the method of the present invention.

In accordance with yet still a further aspect thereof, the present invention provides a composition for treating retinal degeneration-related diseases, comprising retinal cells selected from among photoreceptor cells, retinal ganglion cells, horizontal cells, bipolar cells, amacrine cells, Muller glial cells, retinal pigmented epithelial progenitor cells, retinal pigmented epithelium and a combination thereof, all generated according to the method of the present invention.

The term "retinal degeneration-related disease" is intended to refer to any disease resulting from innate or postnatal retinal degeneration or abnormalities. Examples of retinal degeneration-related diseases include retinal dysplasia, retinal degeneration, aged macular degeneration, diabetic retinopathy, retinitis pigmentosa, congenital retinal dystrophy, Leber congenital amaurosis, retinal detachment, glaucoma, optic neuropathy, and trauma.

Prepared from neural retinal cells comprising neural retinal progenitor cells, photoreceptor cell precursors and/or photoreceptor cells differentiated and proliferated in vitro from human embryonic stem cells using the method of the present invention, the composition for the treatment of retinal degeneration-related diseases may be formulated into typical dosage forms, for example, injections, which can be administered to patients suffering from such a disease. The composition may be directly transplanted into a retinal site using a surgical procedure or may be intravenously injected and migrate to a retinal site. As described above, the composition of the present invention may comprise the completely differentiated retinal cells such as photoreceptor cells, or the differentiating neural retinal progenitor cells or photoreceptor cell precursors as an active ingredient. In the latter case, when administered to the body, the differentiating neural retinal progenitor cells or photoreceptor precursors can undergo further differentiation under the regulation of preexisting factors, thereby exerting therapeutic effects. The composition of the present invention may further comprise an immunosuppressant to suppress immune rejection responses to grafts. The therapeutically effective amount of the composition for a given patient may vary depending on various factors well known in the medical art, including the severity of the disease, regimen, the time and route of administration, regimen, the time period of therapy, the patient's age, body weight, state of health, and sex, and diet, and should be determined by the artisan skilled in the art within the scope of sound medical judgment.

In accordance with another aspect thereof, the present invention provides a method for treating a retinal degeneration-related disease by administering the composition of the present invention to a subject in need thereof. The composition of the present invention may be applied to animals which include livestock or pets such as cow, pigs, sheep, horses, dogs, mice, rats, cats, etc. as well as humans and primates.

The term "administration", as used herein, is intended to refer to the introduction of the composition of the present invention into a patient by a suitable route, including the transplantation of the differentiated cells. Any administration route by which the composition of the present invention reaches a tissue of interest may be employed in the present invention. Preferred is intraretinal injection.

In accordance with another aspect thereof, the present invention provides a method for inducing stem cells to differentiate into retinal cells, comprising treating a differentiation medium with a Wnt signaling pathway inhibitor and removing the Wnt signaling pathway inhibitor from the medium during the differentiation.

Because Wnt proteins play an important role in the development of the hindbrain, a Wnt signaling pathway inhibitor is used at an early stage of the differentiation so as to induce differentiation into the forebrain and retina with the concomitant restraint of differentiation into the hindbrain.

In a preferred embodiment, so long as it is well known in the art, any Wnt signaling pathway inhibitor may be employed without limitation. Dkk-1 is preferred.

In a preferred embodiment, a Wnt signaling pathway inhibitor is added to a medium at an early stage of differentiation to suppress differentiation into the hindbrain and, after the generation of retinal progenitor cells from the stem cells, is removed from the medium with the aim of differentiating and maturing photoreceptor cells in high yield.

In accordance with another aspect thereof, the present invention provides a method for inducing stem cell to differentiate into retinal cells, comprising treating a differentiation medium with a BMP signaling pathway inhibitor and removing the BMP signaling pathway inhibitor from the medium during the differentiation.

The BMP signaling pathway inhibitor is used at an early stage of differentiation to induce and promote the development of the forebrain during embryogenesis and then is removed at a late stage lest it should inhibit the Shh pathway.

In a preferred embodiment, so long as it is well known in the art, any BMP signaling pathway inhibitor may be employed without limitation. Noggin is preferred.

In a preferred embodiment, a BMP signaling pathway inhibitor is added to a medium at an early stage of differentiation and, after the generation of photoreceptor cell precursors from the stem cells, is removed from the medium.

In accordance with another aspect thereof, the present invention provides a method for inducing stem cells to differentiate into retinal cells, comprising treating a differentiation medium with an FGF signaling pathway activator and removing the FGF signaling pathway activator from the medium during the differentiation.

The FGF signaling pathway activator is used at an early stage of differentiation to promote the proliferation of retinal progenitor cells and then is removed at a late stage lest it should inhibit Shh-induced rhodopsin expression.

In a preferred embodiment, so long as it is well known in the art, any FGF signaling pathway activator may be employed without limitation. FGF2 is preferred.

In a preferred embodiment, an FGF signaling pathway activator is added to a medium after differentiation from the stem cell into retinal progenitor cells, and then removed from the medium after the generation of photoreceptor cell precursors from the stem cells.

MODE FOR INVENTION

A better understanding of the present invention may be obtained through the following examples which are set forth to illustrate, but are not to be construed as limiting the present invention.

Example 1

Culture of Stem Cells

<1-1> Culture of Human Embryonic Stem Cells

The human embryonic stem cell (hESC) lines H9 (WA09, normal karyotype XX) and H7 (WA07, normal karyotype, XX) were purchased from the WiCell Research Institute (Madison, Wis., USA).

The hESCs were allowed to proliferate undifferentiated (H9 cells: passages 25~33; H7 cells: passages 23~28) by culturing over feeder cells, such as radiated mouse embryonic fibroblasts (MEF, ATCC, Manassas, Va., USA) or mitomycin-treated mouse embryonic fibroblasts (EmbryoMax Primary Mouse Embryo Fibroblasts, Millipore, Billerica, Mass., USA) in the following medium: DMEM/F12 (Invitrogen, Grand Island, N.Y., USA), 20% (v/v) KnockOut serum replacement, Invitrogen, Carlsbad, Calif., USA), 1 mM L-glutamine (Invitrogen), 0.1 mM nonessential amino acids (Invitrogen), 0.1 mM mercaptoethanol (Sigma-Aldrich, St. Louis, Mo., USA), and 4 ng/ml human recombinant basic fibroblast growth factor (FGF2, Invitrogen).

While the medium was replaced with a fresh one every day, the undifferentiated stem cells were passaged at a ratio of 1:9-1:15 every six or seven days manually or with collagenase IV (Invitrogen), and then transferred onto fresh MEF feeder cells. During the passage of the hESCs, immunochemical staining with OCT-4 and SSEA-4 (Chemicon, Temecula, Calif., USA), antigens characteristic of undifferentiated hESCs, was conducted at regular intervals of time to monitor the degree of differentiation. Cells that were found to have undergo differentiation were removed.

The presence of mycoplasma contamination in the hESC culture, which could have an undesirable effect on the differentiation of hESCs, was regularly monitored with a kit (MycoAlert mycoplasma detection kit, Lonza, Rockland, Me., USA).

<1-2> Culture of Induced Pluipotent Stem Cells (iPSCs)

The human iPSC line iPS (Foreskin)-1 (Clone 1) (normal karyotype XY) was purchased from the WiCell Research Institute (Madison, Wis., USA).

The human iPSCs were allowed to proliferate undifferentiated (passages 37-47) by culturing them over feeder cells, such as radiated mouse embryonic fibroblasts (MEF, ATCC, Manassas, Va., USA) or mitomycin-treated mouse embryonic fibroblasts (EmbryoMax Primary Mouse Embryo Fibroblasts, Millipore, Billerica, Mass., USA) in the following medium: DMEM/F12 (Invitrogen, Grand Island, N.Y., USA), 20% (v/v) KnockOut serum replacement (Invitrogen, Carlsbad, Calif., USA), 1 mM L-glutamine (Invitrogen), 0.1 mM nonessential amino acids (Invitrogen), 0.1 mM mercaptoethanol (Sigma-Aldrich, St. Louis, Mo., USA), and 10 ng/ml human recombinant FGF2 (Invitrogen).

While the medium was replaced with a fresh one every day, the undifferentiated stem cells were passaged at a ratio of 1:4-1:6 every six or seven days manually or with collagenase IV (Invitrogen), and then transferred onto fresh MEF feeder cells. During the passage of the hESCs, immunochemical staining with SSEA-4 (Chemicon, Temecula, Calif., USA) and Nanog (abcam, Cambridge, Mass., USA), which are antigens characteristic of undifferentiated human iPSCs, was conducted at regular intervals of time to monitor the degree of differentiation. Cells that were identified to have undergone differentiation were removed.

The presence of mycoplasma contamination in the hESC culture, which could have an undesirable effect on the differentiation of hESCs, was regularly monitored with a kit (MycoAlert mycoplasma detection kit, Lonza, Rockland, Me., USA).

Example 2

Differentiation from hESCs or Human iPSCs into Eye Field Precursors

The hESCs or human iPSCs cultured in Example 1 were separated from the MEF cells (FIGS. 1 and 14) and seeded into 6-well ultra-low attachment plates (Corning Incorporated, Corning, N.Y., USA).

Figure 1:
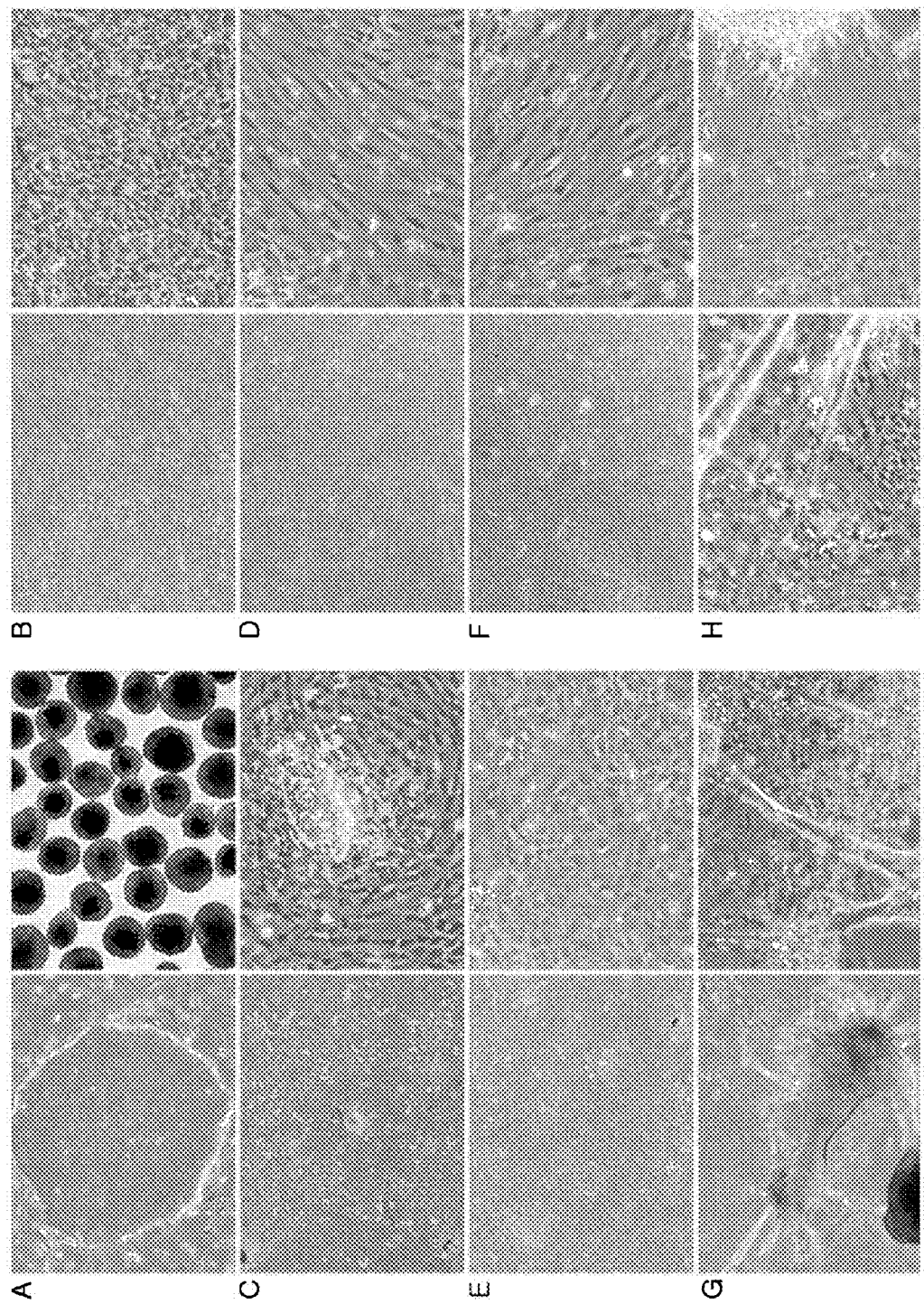
FIG. 1 is of cytomorphological microphotographs.

To the hESCs or human iPSCs in the 6-well ultra-low attachment plates was added a medium for inducing differentiation into eye field precursors [DMEM/F12, 10% Knock-Out serum replacement, 1 mM L-glutamine, 0.1 mM nonessential amino acids, 0.1 mM mercaptoethanol, 1% B27 supplement (Invitrogen), 1 ng/ml recombinant noggin (R&D Systems), 1 ng/ml recombinant Dkk-1 (Dickkopf-1, R&D Systems), and 5 ng/ml recombinant IGF-1 (insulin-like growth factor-1, R&D Systems)]. The cells were cultured for 4-5 days to generate eye field precursors in the form of floating aggregates with the replacement of the medium with a fresh one every third day (FIG. 1).

Example 3

Differentiation from Eye Field Precursors into Retinal Progenitor Cells

The eye field precursors (floating aggregates) generated in Example 2 were seeded at a density of 53±8 cells per well (292±53 cells/floating aggregate) into 6-well poly-D-lysine/laminin-coated plates (BD Biosciences) and at a density of 12±4 cells per well on 8-well poly-D-lysine/laminin-coated plates and then cultured for 9 days to generate retinal progenitor cells, with the supply of a medium for inducing differentiation into retinal progenitor cells [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement, 1% N2 supplement (Invitrogen), 10 ng/ml Dkk-1, 10 ng/ml noggin, 10 ng/ml IGF-1, and 5 ng/ml FGF2].

Example 4

Differentiation from Retinal Progenitor Cells into Neural Retinal Progenitor Cells The retinal progenitor cells generated in Example 3 were cultured in a medium for inducing differentiation into neural retinal progenitor cells [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/ml noggin, 10 ng/ml IGF-1, 5 ng/ml FGF2, 50 ng/ml recombinant Wnt3a (R&D Systems)] supplied thereto for 5 days, thus giving neural retinal progenitor cells (FIG. 1).

Example 5

Differentiation from Neural Retinal Progenitor Cells into Photoreceptor Cell Precursors The neural retinal progenitor cells generated in Example 4 were induced to differentiate into photoreceptor cell precursors by supplying a medium [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/ml IGF-1, 50 ng/ml Wnt3a, and 250 ng/ml recombinant Shh (Sonic Hedgehog amino terminal peptide, Shh, R&D Systems)] for 3 days. Noggin and FGF2, both used in the previous step, were excluded from the medium (FIG. 1).

Example 6

Differentiation from Photoreceptor Cell Precursors into Photoreceptor Cells

A specialized medium [DMEM/F12 (Invitrogen), 1 mM L-glutamine (Invitrogen), 0.1 mM nonessential amino acids (Invitrogen), 0.1 mM mercaptoethanol (Sigma-Aldrich), 1% B27 supplement (Invitrogen), 1% N2 supplement (Invitrogen), 10 ng/ml IGF-1, 50 ng/ml Wnt3a, 250 ng/ml Shh, 500 nM (all-trans retinoic acid (RA, Sigma-Aldrich)] were supplied for 8 days or longer to induce the photoreceptor cell precursors to differentiate into photoreceptorcells.

All the media were replaced with fresh ones every two or three days in Examples 2 to 6, and the cells were cultured at 37° C. in a 5% $CO_2$ atmosphere. All induction and differentiation experiments were repeated at least three times and the same results were obtained therefrom.

Example 7

Assay for Cellular Differentiation-Related Markers

<7-1> Immunochemical Staining and Identification of Cellular Differentiation-Related Marker Expression The differentiation of the cells obtained in Examples 3 to 6 was examined using an immunochemical staining method as follows.

The eye field precursors (floating aggregates) were cultured in 8-well poly-D-lysine/laminin-coated slides (BD Biosciences, Bedford, Mass.) under the same conditions that were used for differentiation into the retinal progenitor cells, the neural retinal progenitor cells, the photoreceptor cell precursors and the photoreceptor cells. The cells completely cultured in each step were fixed with 4% paraformaldehyde (Sigma-Aldrich), after which non-specific reactions were blocked with PBS containing 3% BSA (Jackson Immunoresearch Laboratory, Bar Harbor, Me., USA) and 0.25% Triton X-100 (Sigma-Aldrich).

After being blocked for 90 min, the slides in each differentiation step were incubated overnight at 4° C. with the following antibodies specific for cells of each differentiation step: rabbit-Blue-opsin (1:500, Chemicon), sheep-Chx10

(1:100, Chemicon), rabbit-Crx (1:200, Santa Cruz Biotechnology, Santa Cruz, Calif., USA), rabbit-GFAP (1:200, Invitrogen), mouse-human specific mitochondria (1:50, Chemicon), rabbit-human specific mitochondria (1:200, Chemicon), mouse-Islet1 (1:10, Developmental Studies Hydroma Bank, DSHB; Iowa City, Iowa, USA), mouse-Ki67 (1:100, Vector Laboratories, Peterborough, England), mouse-Mitf (1:1,000, abcam, Cambridge, Mass., USA), mouse-nestin (1:250, BD Sciences), rabbit-neurofilament-200 (1:1,000, Sigma-Aldrich), rabbit-Otx2 (1:100, abcam), rabbit-Pax2 (1:250, abcam), mouse-Pax6 (1:2, DSHB), mouse-peripherin2 (1:500, GenScript, Piscataway, N.J., USA), rabbit-Rax (1:250, abcam), rabbit-recoverin (1:1,000, Chemicon), retinal pigment epithelium 65 (RPE65, 1:100, Chemicon), rabbit-rhodopsin (1:500, Sigma-Aldrich), mouse-rhodopsin (1:500, Ret-P1, Lab Vision, Fremont, Calif., USA), mouse-rhodopsin (1:2,000, Ret-P1, Sigma-Aldrich), mouse-rom1 (1:50, ABR-Affinity Bioreagents, Golden, Colo., USA), rabbit-PDE6 beta (1:100, abcam), rabbit-phosducin (1:500, Santa Cruz Biotechnology), mouse-PKC-alpha (1:500, Sigma-Aldrich), mouse-Prox1 (1:2,000, Chemicon), mouse-Sox2 (1:250, R&D Systems), rabbit-synaptophysin (1:2,000, Santa Cruz Biotechnology), and rabbit-ZO-1 (1:100, Zymed-Invitrogen).

Before use, these antibodies were diluted in a PBS solution containing 1% BSA and 0.25% Triton X-100. The cells cultured on the slides in each step were washed three times for 5 min with PBS and incubated at room temperature for 2 hrs with species-specific secondary antibody conjugated with Cy3 (1:800, Jackson Immunoresearch Laboratory) or Alexa488 (1:500, Invitrogen). A standard material suitable for the primary and the secondary antibody was used to examine non-specific staining or interaction between the antibodies. Afterwards, the cells were washed three times for 5 min with PBS, counterstained with DAPI (4',6-diamidino-2 phenylindole) and mounted in Vectashield (Vector Laboratories), followed by visualization under an epifluorescence microscope (Nikon Eclipse, E800, Tokyo, Japan) and a confocal microscope (Leica, Leica Microsystems Inc, Bannockburn, Ill., USA or Zeiss LSM510, Carl Zeiss, Inc, Thornwood, N.Y., USA).

500 cells were counted from 20 microscopic fields randomly selected at 200 magnification and evaluated for positive responses to each antibody. Positive responses to antibodies were determined after at least three evaluations. Statistical analysis of the data was done using the Kruskal-Wallis test and the Bland-Altman plot (Bland and Altman, 1986) of MedCalc version 8.1.1.0 as well as the GEE (Generalized Estimating Equations) model of SAS version 9.1. All data were represented as mean standard error of the mean (S.E.M) with a statistical significance of $p<0.05$.

With regard to the markers characteristic of both forebrain eye field precursors and retinal progenitor cells, Rax was found to be expressed on the retinal progenitor cells generated in Example 3 at a positive rate of 86.6±3.0%, Pax6 at a positive rate of 63.9±0.9%, Otx2 at a positive rate of 76.4±2.0%, Sox2 at a positive rate of 83.0±1.9%, and Chx10 at a positive rate of 46.3±1.0%. The cells were also found to express the marker Mitf characteristic of retinal pigmented epithelial progenitor cells at a positive rate of 17.2±0.4%, and the marker nestin characteristic of neural progenitor cells at a positive rate of 65.7±2.7% (Tables 1 and 2).

TABLE 1

Change in Marker Level with Culture Time Period

| Marker | Mean ± Mean Standard Deviation (%, Sample size = 3) | | | |
|---|---|---|---|---|
| | 13 Days | 18 Days | 21 Days | 30 Days |
| Rax | 86.6 (±3.0) | 98.2 (±0.9) | 97.6 (±0.6) | 97.8 (±0.7) |
| Pax6 | 63.9 (±0.9) | 89.1 (±2.5) | 61.6 (±0.5) | 89.7 (±1.9) |
| Otx2 | 76.4 (±2.0) | 61.5 (±0.6) | 63.3 (±2.9) | 57.2 (±2.4) |
| Sox2 | 83.0 (±1.9) | 68.1 (±1.1) | 49.1 (±1.6) | 69.1 (±4.0) |
| Chx10 | 46.3 (±1.0) | 64.5 (±1.6) | 48.5 (±3.9) | 41.6 (±2.0) |
| Nestin | 65.7 (±2.7) | 18.0 (±1.4) | 14.3 (±2.3) | 8.5 (±0.9) |
| Mitf | 17.2 (±0.4) | 2.7 (±1.0) | 18.6 (±1.3) | 24.7 (±0.3) |

On the neural retinal progenitor cells generated in Example 4, the positive rates were increased simultaneously from 63.9% to 89.1% for Pax 6, from 86.6% to 98.2% for Rax, and from 46.3% to 64.5% for Chx10 ($p<0.0001$), indicating that the increase in the positive rate of Pax6 resulted from the proliferation of neural retinal progenitor cells (both Rax+ and Pax6+ positive) (Tables 1 and 2).

TABLE 2

Statistical Significance of Retinal Cell Markers between Culture Periods of Time

| Marker | Statistical Significance (p values) | | |
|---|---|---|---|
| | 13 Days vs. 18 Days | 18 Days vs. 21 Days | 21 Days vs. 30 Days |
| Rax | <0.0001 | 0.5308 | 0.7897 |
| Pax6 | <0.0001 | <0.0001 | <0.0001 |
| Otx2 | <0.0001 | 0.4596 | 0.0505 |
| Sox2 | <0.0001 | <0.0001 | <0.0001 |
| Chx10 | <0.0001 | <0.0001 | 0.0531 |
| Nestin | <0.0001 | 0.1077 | 0.0010 |
| Mitf | <0.0001 | <0.0001 | 0.0134 |

Statistical significance : $p < 0.05$

As shown in Tables 1 and 2, the positive rate of the neural progenitor cell marker nestin greatly decreased from 65.7% to 18.0% ($p<0.0001$), from which it is understood that on differentiation day 18, the proliferation of neural progenitor cells was restrained while the proliferation and differentiation of neural retinal cells were promoted.

On the other hand, the proliferative cell marker Ki67 rapidly decreased from 87.5% to 31.5% ($p<0.0001$), indicating that differentiation was more active than proliferation (FIG. 2 and Tables 3 and 4).

TABLE 3

Change in Expression Level of Retinal Cell Markers with Culture Period of Time

| Marker | Mean ± S.E.M. (%, sample size = 3) | | | |
|---|---|---|---|---|
| | 13 Days | 18 Days | 21 Days | 30 Days |
| Crx | 12.8 (±1.6) | 80.1 (±0.2) | 54.8 (±4.2) | 39.5 (±7.4) |
| Recoverin | 35.8 (±0.4) | 68.5 (±2.6) | 61.3 (±1.8) | 82.4 (±4.6) |
| Rhodopsin | 35.3 (±1.7) | 52.9 (±3.4) | 60.4 (±3.2) | 81.2 (±2.5) |
| Peripherin2 | 5.6 (±0.3) | 13.9 (±2.4) | 26.0 (±0.4) | 41.2 (±2.0) |
| Ki67 | 87.5 (±1.3) | 31.5 (±0.5) | 58.4 (±4.1) | 30.2 (±6.1) |

TABLE 4

Statistical Significance of Retinal Cell Markers between Culture Periods of Time

| | Statistical Significance (p values) | | |
|---|---|---|---|
| Marker | 13 Days vs. 18 Days | 18 Days vs. 21 Days | 21 Days vs. 30 Days |
| Crx | <0.0001 | <0.0001 | 0.0326 |
| Recoverin | <0.0001 | 0.0079 | <0.0001 |
| Rhodopsin | <0.0001 | 0.0489 | <0.0001 |
| Peripherin2 | <0.0001 | <0.0001 | <0.0001 |
| Ki67 | <0.0001 | <0.0001 | <0.0001 |

*Statistical significance: p < 0.05

The positive rate of the photoreceptor cell precursor marker Crx showed a drastic increase from 12.8% before Wnt3a addition to 80.1% after Wnt3a addition (p<0.0001) (FIG. 2 and Tables 3 and 4). An increase in the expression level from 35.8% to 68.5% (p<0.0001) was also found in the universal photoreceptor cell marker recoverin, in the rod photoreceptor cell marker rhodopsin from 35.3% to 52.9% (p<0.0001), and in the photoreceptor cell's outer segment marker peripherin2 from 5.6% to 13.9% (p<0.0001) (FIG. 2, Tables 3 and 4). Mitf, an antigen marker of early pigmented epithelial progenitor cells (Baumer, et al., Development, 2003; 130: 2903-15), showed a decrease in positive rate from 17.2% to 2.7% (p<0.0001) (Tables 1 and 2). Also, a decrease in positive rate was found in the retinal progenitor cell markers Otx2 (p<0.0001) and Sox2 (p<0.0001), implying differentiation into neural retinal progenitor cells.

In the photoreceptor cell precursors generated in Example 5, decreased expression levels were detected for the markers of both retinal progenitor cells and neural retinal progenitor cells, including Pax6 (from 89.1% to 61.6%, p<0.0001), Chx10 (from 64.5% to 48.5%, p<0.0001) and Sox2 (from 68.1% to 49.1%, p<0.0001) (Tables 1 and 2). The photoreceptor cell precursor marker Crx also decreased from 80.1% to 54.8% (p<0.0001) (FIG. 2, Tables 3 and 4). On the other hand, an increase in expression level was detected in the photoreceptor cell marker rhodopsin (from 52.9% to 60.5%, p=0.0489) and in the photoreceptor cell's outer segment marker peripherin2 (from 13.9% to 26.0%, p<0.0001), indicating the differentiation and maturation of photoreceptor cells (FIG. 2, Tables 3 and 4). Further, the decreasing positive rate of Ki67 was reversed into increasing from 31.5% to 58.4% (p<0.0001) (FIG. 2, Tables 3 and 4), from which it is understood that Shh started to promote cell proliferation.

As high as 82.4±4.6% of the population of cells generated by the method of Example 6 for differentiation into photoreceptor cells were found to react positive to recoverin, a universal marker of photoreceptor cells (rod photoreceptor cells and cone photoreceptor cells), as measured by a quantitative antigen assay (FIG. 3). Also, the quantitative antigen assay showed that 81.2±2.5% of the cell population was positive to rhodopsin, an antigen characteristic of rod photoreceptor cells (FIG. 3). The fact that almost all of the rhodopsin-positive cells show a positive reaction to recoverin ensures the reliability of the positive responses.

More precise determination of the existence and integrity of the rhodopsin molecules formed by the method of the present invention was carried out using human-specific recombinant rhodoptin (consisting of the amino acids of the second extracellular loop in human rhodopsin) and Ret-P1 (consisting of N-terminal amino acids at positions 4 to 10 in rhodopsin), both of which are rhodopsin antibodies which recognize different epitopes.

The human-specific recombinant rhodopsin and the Ret-P1 were found to have identical positive rates, with a statistically significant difference therebetween, as measured by the Bland-Altman plot (average of difference in positive rate between the two antibodies: −1.00, 95% confidence interval: −13.6-11.6). The cells reacted with almost no difference in the positive rate with both human-specific recombinant rhodopsin and Ret-P1 antibodies. This implies that the rhodopsin molecule formed according to the method of the present invention retains two different epitopes therein.

The rod photoreceptor cell's outer segment markers peripherin2 (Prph2) and rom1 (retinal outer segment membrane protein 1) were positively detected in 41.2±2.0% and 76.0±4.6% of the population of the cells cultured, respectively (FIG. 4). Both of these two markers were observed only in rhodopsin-positive cells (FIG. 4). Positive rates in the photoreceptor cells were measured to be 49.8±2.2% for phosducin, which responds to light, that is, participates in the regulation of visual phototransduction (FIG. 5) and 43.0±2.0% for synaptophysin which is responsible for synaptic interactions with other intraretinal neurons (FIG. 6). These facts prove that these cells participate in the neural circuits of the retina and perform the function of transducing light stimuli into neural electric stimuli. Taken together, the data obtained above demonstrate that the method of the present invention can differentiate with high efficiency human embryonic stem cells into photoreceptor cells.

Blue opsin-cone photoreceptor cells were observed in 80.2±0.6% of all the cells (FIG. 7). These cells were found from rhodopsin-positive cell flocs or in the vicinity thereof, some of which were positive to both rhodopsin and blue opsin. Accordingly, the method of the present invention was proven capable of inducing human embryonic stem cells to differentiate into both rod and cone photoreceptor cells.

Of the total population of the cells, 39.5±7.4% were positive to Crx, a marker characteristic of photoreceptor cell precursors, and 30.2±6.1% were positive to Ki67, a nuclear marker of proliferating cells (late G1 phase to M phase in the cell cycle). Photoreceptor cell precursors are reported to express Crx immediately after leaving the cell proliferation cycle. Also in the present invention, most of the human ESC-derived, Crx-positive cells were observed to be negative to K167, a marker associated with cell proliferation. However, the Crx-positive cells were found to express Ki67 at a positive rate of 5.5±1.7% (FIG. 9).

From the data obtained above, it is apparent that the method of the present invention can effectively differentiate photoreceptor cells from human ESC-derived retinal progenitor cells in the same multi-step induction pattern as they do from embryonic retinal progenitor cells, where differentiation progresses in steps along the early and late embryonic stage. The retinal progenitor cell marker Pax6 had a positive rate of 89.7±1.9% and was detected in amacrine cells, which are a type of differentiated retinal neurons. Meanwhile, the retinal progenitor cells expressed Mitf (a marker of retinal pigmented epithelium (RPE) progenitor cells) at a positive rate of 24.7±0.3%, and ZO-1 (a marker of differentiated RPE) at a positive rate of 12.5±1.4%, and were also positive to RPE65, a marker of differentiated RPE (FIG. 10).

<7-2> RT-PCR and RNA mRNA Expression of Cellular Differentiation-Associated Markers To examine the differentiation of the photoreceptor cells generated in Example 6, a reverse transcriptase-polymerase chain reaction (RT-PCR) was performed on Day 29 of differentiation induction.

Total RNA was isolated with an RNeasy minikit (Qiagen, Valencia, Calif., USA) and DNA was removed from the RNA isolate using DNaseI (Applied Biosystems/Ambion, Austin, Tex., USA). 500 g of the RNA was reverse transcribed into cDNA in the presence of reverse transcriptase (Omniscript reverse transcriptase, Qiagen), with random hexamers (Invitrogen) serving as primers. For the PCR, 1×PCR buffer, 1.5 mM $MgCl_2$, 0.2 mM dNTPs, 50 ng DNA, 0.5 U AmpliTaq Gold (Applied Biosystems, Foster City, Calif., USA) and 10 pmoles of each of the primers given in Table 5, below, were used.

TABLE 5

Forward and Reverse Primer Sequences for RT-PCR

| Gene | SEQ ID NO | Primer sequence (5' to 3') | Amplified product (bp) |
|---|---|---|---|
| PAX6 | 1 | Forward: aacagacacagccctcacaaaca | 275 |
| PAX6 | 2 | Reverse: cgggaacttgaactggaactgac | 275 |
| SIX3 | 3 | Forward: cgggagtggtacctacagga | 307 |
| SIX3 | 4 | Reverse: ttaccgagaggatggaggtg | 307 |
| SIX6 | 5 | Forward: cctgcaggatccataccta | 272 |
| SIX6 | 6 | Reverse: tgatggagtggctgaagtg | 272 |
| LHX2 | 7 | Forward: ccaaggacttgaagcagctc | 285 |
| LHX2 | 8 | Reverse: tgccaggcacagaagttaag | 285 |
| RAX | 9 | Forward: ggcaaggtcaacctaccaga | 495 |
| RAX | 10 | Reverse: gtgctccttggctttcagac | 495 |
| CRX | 11 | Forward: gtgtggatctgatgcaccag | 353 |
| CRX | 12 | Reverse: tgagatgcccagagggtct | 353 |
| CHX10 | 13 | Forward: ggcgacacaggacaatcttt | 281 |
| CHX10 | 14 | Reverse: atccttggctgacttgagga | 281 |
| NRL | 15 | Forward: ggcactgaccacatcctctc | 206 |
| NRL | 16 | Reverse: ggaggcactgagctgtaagg | 206 |
| RCVRN | 17 | Forward: agctccttccagacgatgaa | 150 |
| RCVRN | 18 | Reverse: caaactggatcagtcgcaga | 150 |
| RHO | 19 | Forward: taagcccatgagcaacttcc | 258 |
| RHO | 20 | Reverse: agctgcccatagcagaaaaa | 258 |
| RBP3 | 21 | Forward: cagcccatatccctgagaat | 291 |
| RBP3 | 22 | Reverse: agcacaagatgggaatggag | 291 |
| PDE6B | 23 | Forward: aggagaccctgaacatctacc | 409 |
| PDE6B | 24 | Reverse: atgaagcccacttgcagc | 409 |
| OPN1SW | 25 | Forward: ctgggcactgtagcaggtct | 206 |
| OPN1SW | 26 | Reverse: tgcaggccctcagggatg | 206 |
| ASCL1 | 27 | Forward: catctcccccaactactcca | 467 |
| ASCL1 | 28 | Reverse: cttttgcacacaagctgcat | 467 |
| NEUROD1 | 29 | Forward: gccccagggttatgagactatcact | 523 |
| NEUROD1 | 30 | Reverse: ccgacagagcccagatgtagttctt | 523 |
| ATHO7 | 31 | Forward: tcgcatcatcagacctatgg | 246 |
| ATHO7 | 32 | Reverse: ccgaacaggacaaactcaca | 246 |
| POU4F2 | 33 | Forward: caaccccaccgagcaata | 175 |
| POU4F2 | 34 | Reverse: gtgcacgggatggtattcat | 175 |
| ARX | 35 | Forward: tgaaacgcaaacagaggcgcta | 462 |
| ARX | 36 | Reverse: tgatgaaagctgggtgtcggaaca | 462 |
| AFP | 37 | Forward: tttagctgacctggctaccat | 318 |
| AFP | 38 | Reverse: cagcttgtgacaggttctgg | 318 |
| T | 39 | Forward: ccgtctccttcagcaaagtc | 541 |
| T | 40 | Reverse: caattgtcatgggattgcag | 541 |
| GAPDH | 41 | Forward: agccacatcgctcagacacc | 302 |
| GAPDH | 42 | Reverse: gtactcagcgccagcatcg | 302 |
| SAG | 43 | Forward: aaaaagtgccaccaaacagc | 400 |
| SAG | 44 | Reverse: acgtcattcttgtctctcttcc | 400 |

After initial DNA denaturation at 94° C. for 10 min, all PCR was performed over 35 cycles starting with initial DNA denaturation (94° C. for 30 sec, 60° C. for 30 sec, 72° C. for 1 min) and terminating with extension at 72° C. for 10 min. The PCR products thus obtained were isolated by electrophoresis on 2% agarose gel and analyzed.

All experiments were conducted in triplicate and human GAPDH was used as a reference molecule for standard mRNA calculation.

The retinal progenitor cell-related genes RAX, PAX6, SIX3, SIX6, LHX2 and CHX10 were detected in the RT-PCR products. Inter alia, RAX and PAX6 were expressed to as the same high extent as was the quantitative control gene GAPDH. Genes relevant to photoreceptor cells and other retinal cells were also examined for mRNA expression. The PCR products were observed to include the photoreceptor cell-associated genes CRX, NRL, RCVRN, RHO, PDE6B, SAG and OPN1SW, the retinal ganglion cell-related genes ATHO7 and POU4F2, and the amacrine cell-related gene NEUROD1, and the bipolar cell-related gene ASCL1 (FIG. 16).

<7-3> Base Sequencing for Identifying mRNA Expression of Recoverin and Rhodopsin, Both Specific for Differentiated Photoreceptor Cells In order to investigate the differentiation of the photoreceptor cells generated in Example 6, base sequencing was conducted on the photoreceptor cell-specific genes recoverin (RCVRN: NM_002903.2) and rhodopsin (RHO: NM_000539.3) on Day 29 of differentiation.

The PCR products were purified with a QIAquick 96-well PCR purification kit (Qiagen, Valencia, Calif.) and sequenced using the forward and reverse primers listed in Table 5, with the aid of a base sequencing kit (BigDye terminator cycle sequencing ready reaction kit, Applied Biosystems, Foster City, Calif., USA). The fluorescent labeled fragments thus produced were purified by ethanol precipitation, resuspended in distilled water, and electrophoresed in an ABI PRISM 3700 DNA analyzer (Applied Biosystems, Foster City, Calif., USA), followed by analysis of the base sequences with a sequencer (Gene Codes Corporation, Ann Arbor, Mich., USA).

The RCVRN and RHO genes expressed in the photoreceptor cells differentiated according to the present invention were found to perfectly coincide with human standard sequences (http://www.ncbi.nlm.nih.gov/), indicating that the photoreceptor cells express human RCVRN and RHO genes (FIG. 17).

Example 8

Transplantation of Photoreceptor Cells Differentiated from hESCs and Evaluation of Transplanted Cells <8-1> Transplantation of Differentiated Photoreceptor Cells The transplantability and clinical applicability of the photoreceptor cells generated in Example 6 to blind persons were examined on the immunosuppressant retinal-degeneration mouse model rd/SCID.

After getting permission from the institutional Review Board of the Seoul National University College of Medicine/the Seoul National University Hospital and the Institutional Animal Care and Use Committee (IACUC) of Seoul National University/the Seoul National University Hospital, all animal experiments were conducted according to the ARVO Statement for the Use of Animals in Ophthalmic and Vision Research. For the transplantation, four-week-old C3H/Prkdc mice (rd/SCID, Jackson Laboratory, Bar Harbor, Me., USA) were employed. C3H/Prkdc mice were also used as a negative control.

The retinal cells comprising photoreceptor cells differentiated from hESCs according to the present invention were detached with accutase and suspended in Dulbecco's PBS (D-PBS, Invitrogen) to form a single-cell suspension with a density of $6\text{-}10 \times 10^4$ cells/μL. A surgical procedure was carried out under a dissecting microscope (SZ51, Olympus, Tokyo, Japan). After the mice were anesthetized by intraperitoneal injection of a mixture of zoletil (7.5 mg/kg, Virbac Laboratoires, Carros, France) and xylazine (10 mg/kg, BayerKorea, Korea), drops of a cycloplegic-mydriatic agent (Mydrin-P, Santen Pharmaceutical Co., Osaka, Japan) and 0.5% proparacaine (Alcaine 0.5%, Alcon, Inc., Puurs, Belgium) were put into the eyes. 1 μL of the cell suspension was transplanted into each mouse by subretinal injection using a 10 μL injector (NanoFil microsyringe, World Precision Instruments, WPI, Sarasota, Fla., USA) equipped with a 35-gauge needle (WPI).

<8-2> Electroretinography Retinal Degeneration after Transplantation into Mice with Retinal Degeneration The retinal function of the mice transplanted with the photoreceptor cells differentiated from hESCs according to the present invention was evaluated by electroretinography (ERG, Roland Consult, Wiesbaden, Germany) 3-5 weeks after transplantation. For this, the mice were acclimated to darkness for one day before the test. Prior to the electroretinography, the mice were anesthetized by intraperitoneal injection of a mixture of zoletil (7.5 mg/kg, Virbac Laboratoires, Carros, France) and xylazine (10 mg/kg, BayerKorea, Korea) and drops of Mydrin-P (Santen Pharmaceutical Co., Osaka, Japan) and 0.5% proparacaine (Alcaine 0.5%, Alcon, Inc., Puurs, Belgium) were applied to the eyes. Simultaneously, vidisic Gel (Dr. Mann Parma, Berlin, Germany) was also put into the eyes so as to prevent eye dryness.

While the body temperature of the mice was maintained at 37° C. on a mouse table (Roland Consult, Wiesbaden, Germany), the responses of retinal nerves to light at intensities of −25, −10, and 0 dB were recoded with the RETIport System (Roland Consult, Wiesbaden, Germany), and the records were analyzed with the RETI-scan System (Roland Consult, Wiesbaden, Germany). The same electroretinography was performed on non-transplanted C57BL6 mice for positive control and on non-transplanted C3H/Prkdc mice (rd/SCID) for negative control.

After the retinoelectrography, the mice were subjected to euthanasia by $CO_2$ injection and cervical dislocation. The eyeballs were excised, followed by immunofluorescent staining. In detail, the eyeballs excised immediately after euthanasia were fixed overnight at 4° C. with 4% paraformaldehyde, cryoprotected in 10% and 30% sucrose (Sigma-Aldrich), embedded in OCT (Tissue-Tek, Sakura, Tokyo, Japan), and immediately stored at −80° C. Four weeks after the transplantation, some of the mice were subjected to euthanasia by $CO_2$ injection and cervical dislocation without electroretinography before the excision of the eyeballs. Then, immunofluorescent staining was performed on the eyeballs as described above.

Recovered signals in the electroretinograms reflect the effects and efficacies of the cells transplanted into injured retinas. Particularly, the existence of rhodopsin within the retina of the photoreceptor cell-transplanted mice is closely associated with the amplitude of b-waves. In the electroretinography, non-transplanted rd/SCID mice of the same age (7-9 weeks old) did not respond to light stimuli (FIG. 18A). In contrast, photoreceptor cell-transplanted rd/SCID mice gave definite responses to light stimuli (FIG. 18B). The ERG b-wave from the eyes of the photoreceptor cell-transplanted rd/SCID mice showed characteristic wave forms (FIG. 18B) with an amplitude of 48.4 (±13.4) μV (sample size=13) (FIG. 19). Nowhere were characteristic wave forms found in the ERG of the non-transplanted group, which showed a b-wave amplitude of 10.3 (±2.5) μV (sample size=17) different from that of the transplanted group with statistical significance ($p<0.0001$) (Table 6, FIG. 19).

TABLE 6

Electroretinography of Mice with Retinal Degeneration After Transplantation with hESC-Derived Photoreceptor Cells

| | Non-Transplanted Group (Mean ± S.E.M.) (Sample Size = 17) | Transplanted Group (Mean ± S.E.M.) (Sample Size = 13) |
| --- | --- | --- |
| b-Wave Amplitude (μV) | 10.3 (±2.5) | 48.4 (±13.4) |

<8-3> Immunochemistry and Evaluation of Transplanted Cells

The cryoprotected segments were sectioned at a thickness of 16 μm and fixed onto glass slides (Muto Pure Chemicals Co., Tokyo, Japan), followed by immunochemical staining with antibodies to human mitochondria and photoreceptor cells (no. of mouse models=13).

When the photoreceptor cells were transplanted into the retina of the mice suffering from retinal degeneration, a new 4- or 5-fold photoreceptor cell layer was formed, comprising the outer nuclear layer consisting of cells characterized by rhodopsin and recoverin (FIG. 20). There was a remarkable difference in the positive rate of rhodopsin and recoverin between photoreceptor cell-transplanted group and non-transplanted cells. In the non-transplanted group, rhodopsin was detected in only two of a total of 199 cells per observation microscopic field (positive rate: 1.0%). In contrast, 88 of a total of 215 cells per microscopic field were rhodopsin positive in the transplanted group, with an outer nuclear layer consisting of a 4- or 5-fold rhodopsin-positive cell layer formed therein (positive rate: 40.8%) ($p<0.0001$) (Table 7 and FIG. 21).

As a result, the transplanted rod photoreceptor cells were found to occupy approximately 40% of the total area of the retinal sections. Rhodopsin discs, which are embedded in the membrane of the outer segment of photoreceptor cells in the normal retina, were also found in the photoreceptor cells of the transplanted mice (FIG. 20). Primarily structured to convert light energy into electric energy, rhodopsin discs are responsible for the first events in the perception of light. The engrafted/differentiated photoreceptors of the transplanted mice, particularly, the rhodopsin discs of the outer segment were thought to include responses to light stimuli in the electroretinography, amplifying the amplitude of the b-wave.

Recoverin expression was observed in 40 of the total of 168 cells per microscopic field in the non-transplanted group (positive rate: 23.8%), but in 120 of the total 292 cells per microscopic field in the transplanted group (positive rate: 41.0%) ($p<0.0001$) (Table 7 and FIG. 21). In the non-transplanted group, recoverin means bipolar cells in the inner nuclear layer and cone photoreceptor cells in the outer nuclear layer. In the transplanted group, a 4- or 5-fold recoverin-positive cell layer was formed in the outer nuclear layer as well as in the inner nuclear layer. From these observations, it is understood that when transplanted into an injured retina, hESC-derived photoreceptor cells can graft at proper loci onto the retina and effectively reconstruct the outer nuclear layer which has been lost due to degeneration.

TABLE 7

Evaluation of hESC-Derived Photoreceptor Cells Transplanted into Mice with Retinal Degeneration

| Marker | Non-transplanted Group | | | Transplanted Group | | |
|---|---|---|---|---|---|---|
| | No. of Positive Cells | Total Cell Count | Positive Rate (%) | No. of Positive Cells | Total Cell Count | Positive Rate (%) |
| rhodopsin | 2 | 199 | 1 | 88 | 215 | 40.8 |
| recoverin | 40 | 168 | 23.8 | 120 | 292 | 41.0 |

In addition, the engrafted cells were observed to express synaptophysin, suggesting that they constructed, in synaptic interaction with other intraretinal cells, retinal neurons and light circuits (FIG. 22). That is, the expression of synaptophysin indicates that the photoreceptor cells in the newly formed outer nuclear layer are using synapses to interact with other intraretinal cells to function as a circuit in response to light.

Taken together, the data obtained above implies that when transplanted, the photoreceptor cells differentiated from hESCs according to the present invention can participate in the construction of retinal circuits, exert their own functions in the transplanted subject, and open up the new possibility of giving vision to patients suffering from blindness that is attributed to the loss of photoreceptor cells.

Example 9

Positive Rates of Retinal Cell Markers Upon Use of Substitutes for Wnt3a and Shh Differentiation from retinal progenitor cells into neural retinal progenitor cells, from neural retinal progenitor cells into photoreceptor cell precursors, and from photoreceptor cells into photoreceptor cells was induced in the same manner as in Examples 4 to 6, with the exception that the media used in Examples 4 to 6 contained 50 ng/ml recombinant Wnt1 (PeproTech, Rocky Hill, N.J., USA), 50 and 100 ng/ml recombinant Wnt5A (R&D Systems), 50 and 100 ng/ml recombinant Wnt11 (R&D Systems), 50 ng/ml recombinant Norrin (R&D Systems), 2.5 and 5 mM LiCl (Sigma-Aldrich), 2 µM BIO (Sigma-Aldrich), or 30 µM SB415286 (Sigma-Aldrich), instead of the recombinant Wnt3a, and with the further exception that the media used in Examples 5 and 6 contained 1 µM purmorphamine (Stemgent, Cambridge, Mass., USA) instead of the recombinant Shh.

The cells differentiated with various substitutes for Wnt3a and Shh were subjected to immunochemical staining in the same manner as in Example 7-1 and assayed for positive rates of retinal cell markers, and the results are summarized in Tables 8 and 9, below.

TABLE 8

Positive Rates of Retinal Cell Markers upon Use of Wnt3a Substitutes

| | Mean ± S.E.M (%, Sample size = 3) | | | | | | | |
|---|---|---|---|---|---|---|---|---|
| Substitute | recoverin | rhodopsin | Rom | peripherin2 | Crx | Ki67 | Pax6 | b-opsin |
| Wnt1 (50 ng/ml) | 70.9 (±1.8) | 66.2 (±5.4) | 55.9 (±2.9) | 3.8 (±2.0) | 60.3 (±1.3) | 23.8 (±1.2) | ND | 61.6 (±6.8) |
| Wnt5A (50 ng/mL) | 61.0 (±3.2) | 59.5 (±2.0) | 58.8 (±2.7) | 20.7 (±0.8) | 67.3 (±1.9) | 41.3 (±3.9) | ND | 55.0 (±4.4) |
| Wnt5A (100 ng/ml) | 61.6 (±2.5) | 56.1 (±1.8) | ND | 14.2 (±2.8) | ND | ND | ND | ND |
| Wnt11 (50 ng/ml) | 65.3 (±2.7) | 51.8 (±7.7) | 50.2 (±7.4) | 0.5 (±0.3) | 65.9 (±5.8) | 40.1 (±5.2) | ND | 30.6 (±6.2) |
| Wnt11 (100 ng/ml) | 61.8 (±4.1) | 59.1 (±5.4) | ND | 10.7 (±2.9) | ND | ND | ND | ND |
| Norrin (50 ng/ml) | 85.0 (±7.2) | 82.9 (±7.1) | 69.5 (±2.7) | 24.9 (±4.5) | 39.3 (±0.8) | 42.2 (±6.8) | ND | 71.1 (±0.6) |
| BIO (2 uM) | 77.1 (±0.8) | 71.5 (±1.2) | 60.3 (±0.9) | 33.9 (±0.1) | 65.8 (±1.0) | 17.2 (±0.6) | 92.8 (±1.0) | 77.5 (±1.8) |

TABLE 8-continued

Positive Rates of Retinal Cell Markers upon Use of Wnt3a Substitutes

Mean ± S.E.M (%, Sample size = 3)

| Substitute | recoverin | rhodopsin | Rom | peripherin2 | Crx | Ki67 | Pax6 | b-opsin |
|---|---|---|---|---|---|---|---|---|
| SB415286 (30 uM) | 70.0 (±0.6) | 69.3 (±0.5) | 59.5 (±0.7) | 9.1 (±0.6) | 53.7 (±2.7) | 13.3 (±1.2) | 89.1 (±0.6) | 53.7 (±2.7) |
| LiCl (2.5mM) | 64.1 (±2.9) | 56.2 (±1.7) | ND | ND | ND | ND | ND | ND |
| LiCl (5 mM) | 78.9 (±4.4) | 68.5 (±2.2) | ND | 1.5 (±0.9) | 5.0 (±1.7) | 33.3 (±2.2) | ND | ND |

*ND: Non-determined.

TABLE 9

Positive Rates of Retinal Cell Markers upon Use of Shh Substitutes

Mean ± S.E.M (%, Sample size = 3)

| Substitute | recoverin | rhodopsin | peripherin2 | Crx | Ki67 |
|---|---|---|---|---|---|
| purmorphamine (1 uM) | 76.5 (±0.9) | 73.5 (±1.2) | 41.5 (±1.2) | 71.6 (±0.8) | 24.3 (±0.5) |

As is apparent from the data of Tables 8 and 9, the Wnt3a substitutes, Wnt1, Wnt5a, Wnt11, norrin, LiCl, BIO and SB415286 and the Shh substitute purmorphamine allowed the retinal cell markers to be expressed at similar positive rates to those when Wnt3a and Shh were used.

---

The invention claimed is:

1. A method for differentiating stem cells into retinal cells, comprising:
   (i) inducing stem cells to differentiate into eye field precursors in a form of floating aggregates by culturing stem cells in a medium containing an IGF1R activator, a Wnt signaling pathway inhibitor and a BMP signaling pathway inhibitor;
   (ii) inducing the eye field precursors of step (i) to differentiate into retinal progenitor cells by culturing the eye field precursors in a medium containing IGF1R activator, a BMP signaling pathway inhibitor, an FGF signaling pathway activator and a Wnt signaling pathway inhibitor;
   (iii) inducing the retinal progenitor cells of step (ii) to differentiate into neural retinal progenitor cells by culturing the retinal progenitor cells in a medium containing IGF1R activator, a BMP signaling pathway inhibitor, an FGF signaling pathway activator and a Wnt signaling pathway activator;
   (iv) inducing the neural retinal progenitor cells of step (iii) to differentiate into photoreceptor cell precursors by culturing the neural retinal progenitor cells in a medium containing an IGF1R activator, a Wnt signaling pathway activator and an Shh (sonic hedgehog) signaling pathway activator; and
   (v) inducing the photoreceptor cell precursors of step (iv) to differentiate into retinal cells, including photoreceptor cells, by culturing the photoreceptor cell precursors in a medium containing an IGF1R activator, a Wnt signaling pathway activator, an Shh signaling pathway activator and RA (retinoic acid).

2. The method as set forth in claim 1, wherein the neural retinal progenitor cells are cultured for 1 to 30 days to generate the photoreceptor cell precursors.

3. The method according to claim 1 or 2, wherein the stem cells are selected from the group consisting of bone marrow stem cells (BMSs), cord blood stem cells, amniotic fluid stem cells, fat stem cells, retinal stem cells (RSCs), intraretinal Müller glial cells, embryonic stem cells (ESCs), induced pluripotent stem cells (iPSCs) and somatic cell nuclear fusion cells (SCNT).

4. The method according to claim 1 or 2, wherein the IGF1R activator is IGF-1 or IGF-2.

5. The method according to claim 1 or 2, wherein the medium contains the IGF1R activator at a concentration of 0.01 to 100 ng/mL.

6. The method according to claim 1 or 2, wherein the Wnt signaling pathway activator is selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; β-catenin expression level-increasing substances; GSK3 (glycogen synthase kinase 3) inhibitors selected from the group consisting of lithium (Li); LiCl, bivalent zinc (bivalent Zn), BIO (6-bromoindirubin-3'-oxime), SB216763, SB415286, CHIR99021, QS11 hydrate, TWS119, kenpaullone, alsterpaullone, indirubin-3'-oxime, TDZD-8, Ro 31-8220 methanesulfonate salt and a combination thereof; Axin inhibitors; APC (adenomatous polyposis coli) inhibitors; norrin; R-spondin 2; and a combination thereof.

7. The method as set forth in claim 6, wherein the medium contains the Wnt signaling pathway activator selected from the group consisting of Wnt1, Wnt2, Wnt2b, Wnt3, Wnt3a, Wnt4, Wnt5a, Wnt5b, Wnt6, Wnt7a, Wnt7b, Wnt8a, Wnt8b, Wnt9a, Wnt9b, Wnt10a, Wnt10b, Wnt11, Wnt16b; β-catenin expression level-increasing substances; GSK3 (glycogen synthase kinase 3) inhibitors selected from the group consisting of lithium (Li), bivalent zinc (bivalent Zn), SB216763, CHIR99021, QS11 hydrate, TWS119, kenpaullone, alsterpaullone, indirubin-3'-oxime, TDZD-8, Ro 31-8220 methanesulfonate salt and a combination thereof; Axin inhibitors; APC (adenomatous polyposis coli) inhibitors; norrin; R-spondin 2; and a combination thereof at a concentration of 0.01 to 500 ng/ml.

8. The method as set forth in claim 6, wherein when LiCl, BIO or SB415286 is used as a Wnt signaling pathway activator, the medium contains LiCl at a concentration of 0.1 to 50 mM; BIO at a concentration of 0.1 to 50 μM; and SB415286 at a concentration of 0.1 to 500 μM.

9. The method as set forth in claim 1, wherein the Shh signaling pathway activator is selected from the group consisting of Shh, Smo (smoothened) receptor activators, inhibitors of Ptc (Patched) interaction with Smo, substances increasing Ci/Gli family levels, inhibitors of the intracellular degradation of Ci/Gli factors, Hg—Ag, purmorphamine, and a combination thereof.

10. The method as set forth in claim 1, wherein the medium contains the Shh signaling pathway activator at a concentration of 0.1 to 5000 ng/mL.

11. The method as set forth in claim 1, further comprising determining whether the differentiated cells are target cells or not.

12. The method as set forth in claim 11, wherein the determining step is carried out by analyzing a gene characteristic of retinal progenitor cells, neural retinal progenitor cells, photoreceptor cell precursors or photoreceptor cells for mRNA or protein expression levels.

13. The method as set forth in claim 12, wherein the gene characteristic of neural retinal progenitor cells is a combination of at least two genes selected from the group consisting of Rax, Pax6, Chx10 and Crx.

14. The method as set forth in claim 12, wherein the gene characteristic of photoreceptor cell precursors is Crx or Nrl.

15. The method as set forth in claim 12, wherein the gene characteristic of photoreceptor cells is selected from the group consisting of recoverin, rhodopsin, peripherin2, rom1, Pde6b, arrestin sag, phosducin, synaptophysin, red/green-opsin, blue-opsin and a combination thereof.

16. The method according to claim 1 or 2, wherein the retinal cells are selected from the group consisting of photoreceptor cells, retinal ganglion cells, horizontal cells, bipolar cells, amacrine cells, Müller glial cells, retinal pigmented epithelial progenitor cells, retinal pigmented epithelium and combinations thereof.

17. The method as set forth in claim 16, wherein the photoreceptor cells constitute more than 50% of a population of the retinal cells.

* * * * *

SEQUENCE LISTING

```
<160> NUMBER OF SEQ ID NOS: 44

<210> SEQ ID NO 1
<211> LENGTH: 23
<212> TYPE: DNA
<213> ORGANISM: Artificial Sequence
<220> FEATURE:
<223> OTHER INFORMATION: Forward primer for PAX6

<400> SEQUENCE: 1
aacagacaca gccctcacaa aca                                              23

<210> SEQ ID NO 2
<211> LENGTH: 23
<212> TYPE: DNA
<213> ORGANISM: Artificial Sequence
<220> FEATURE:
<223> OTHER INFORMATION: Reverse primer for PAX6

<400> SEQUENCE: 2
cgggaacttg aactggaact gac                                              23

<210> SEQ ID NO 3
<211> LENGTH: 20
<212> TYPE: DNA
<213> ORGANISM: Artificial Sequence
<220> FEATURE:
<223> OTHER INFORMATION: Forward primer for SIX3

<400> SEQUENCE: 3
cgggagtggt acctacagga                                                  20

<210> SEQ ID NO 4
<211> LENGTH: 20
<212> TYPE: DNA
<213> ORGANISM: Artificial Sequence
<220> FEATURE:
<223> OTHER INFORMATION: Reverse primer for SIX3

<400> SEQUENCE: 4
```

```
ttaccgagag gatggaggtg                                          20

<210> SEQ ID NO 5
<211> LENGTH: 20
<212> TYPE: DNA
<213> ORGANISM: Artificial Sequence
<220> FEATURE:
<223> OTHER INFORMATION: Forward primer for SIX6

<400> SEQUENCE: 5
cctgcaggat ccatacccta                                          20

<210> SEQ ID NO 6
<211> LENGTH: 20
<212> TYPE: DNA
<213> ORGANISM: Artificial Sequence
<220> FEATURE:
<223> OTHER INFORMATION: Reverse primer for SIX6

<400> SEQUENCE: 6
tgatggagat ggctgaagtg                                          20

<210> SEQ ID NO 7
<211> LENGTH: 20
<212> TYPE: DNA
<213> ORGANISM: Artificial Sequence
<220> FEATURE:
<223> OTHER INFORMATION: Forward primer for LHX2

<400> SEQUENCE: 7
ccaaggactt gaagcagctc                                          20

<210> SEQ ID NO 8
<211> LENGTH: 20
<212> TYPE: DNA
<213> ORGANISM: Artificial Sequence
<220> FEATURE:
<223> OTHER INFORMATION: Reverse primer for LHX2

<400> SEQUENCE: 8
tgccaggcac agaagttaag                                          20

<210> SEQ ID NO 9
<211> LENGTH: 20
<212> TYPE: DNA
<213> ORGANISM: Artificial Sequence
<220> FEATURE:
<223> OTHER INFORMATION: Forward primer for RAX

<400> SEQUENCE: 9
ggcaaggtca acctaccaga                                          20

<210> SEQ ID NO 10
<211> LENGTH: 20
<212> TYPE: DNA
<213> ORGANISM: Artificial Sequence
<220> FEATURE:
<223> OTHER INFORMATION: Reverse primer for RAX

<400> SEQUENCE: 10
gtgctccttg gctttcagac                                          20

<210> SEQ ID NO 11
<211> LENGTH: 20
<212> TYPE: DNA
```

```
<213> ORGANISM: Artificial Sequence
<220> FEATURE:
<223> OTHER INFORMATION: Forward primer for CRX

<400> SEQUENCE: 11
gtgtggatct gatgcaccag                                                 20

<210> SEQ ID NO 12
<211> LENGTH: 19
<212> TYPE: DNA
<213> ORGANISM: Artificial Sequence
<220> FEATURE:
<223> OTHER INFORMATION: Reverse primer for CRX

<400> SEQUENCE: 12
tgagatgccc agagggtct                                                  19

<210> SEQ ID NO 13
<211> LENGTH: 20
<212> TYPE: DNA
<213> ORGANISM: Artificial Sequence
<220> FEATURE:
<223> OTHER INFORMATION: Forward primer for CHX10

<400> SEQUENCE: 13
ggcgacacag gacaatcttt                                                 20

<210> SEQ ID NO 14
<211> LENGTH: 20
<212> TYPE: DNA
<213> ORGANISM: Artificial Sequence
<220> FEATURE:
<223> OTHER INFORMATION: Reverse primer for CHX10

<400> SEQUENCE: 14
atccttggct gacttgagga                                                 20

<210> SEQ ID NO 15
<211> LENGTH: 20
<212> TYPE: DNA
<213> ORGANISM: Artificial Sequence
<220> FEATURE:
<223> OTHER INFORMATION: Forward primer for NRL

<400> SEQUENCE: 15
ggcactgacc acatcctctc                                                 20

<210> SEQ ID NO 16
<211> LENGTH: 20
<212> TYPE: DNA
<213> ORGANISM: Artificial Sequence
<220> FEATURE:
<223> OTHER INFORMATION: Reverse primer for NRL

<400> SEQUENCE: 16
ggaggcactg agctgtaagg                                                 20

<210> SEQ ID NO 17
<211> LENGTH: 20
<212> TYPE: DNA
<213> ORGANISM: Artificial Sequence
<220> FEATURE:
<223> OTHER INFORMATION: Forward primer for RCVRN

<400> SEQUENCE: 17
agctccttcc agacgatgaa                                                 20
```

-continued

<210> SEQ ID NO 18
<211> LENGTH: 20
<212> TYPE: DNA
<213> ORGANISM: Artificial Sequence
<220> FEATURE:
<223> OTHER INFORMATION: Reverse primer for RCVRN

<400> SEQUENCE: 18
caaactggat cagtcgcaga                                              20

<210> SEQ ID NO 19
<211> LENGTH: 20
<212> TYPE: DNA
<213> ORGANISM: Artificial Sequence
<220> FEATURE:
<223> OTHER INFORMATION: Forward primer for RHO

<400> SEQUENCE: 19
taagcccatg agcaacttcc                                              20

<210> SEQ ID NO 20
<211> LENGTH: 20
<212> TYPE: DNA
<213> ORGANISM: Artificial Sequence
<220> FEATURE:
<223> OTHER INFORMATION: Reverse primer for RHO

<400> SEQUENCE: 20
agctgcccat agcagaaaaa                                              20

<210> SEQ ID NO 21
<211> LENGTH: 20
<212> TYPE: DNA
<213> ORGANISM: Artificial Sequence
<220> FEATURE:
<223> OTHER INFORMATION: Forward primer for RBP3

<400> SEQUENCE: 21
cagcccatat ccctgagaat                                              20

<210> SEQ ID NO 22
<211> LENGTH: 20
<212> TYPE: DNA
<213> ORGANISM: Artificial Sequence
<220> FEATURE:
<223> OTHER INFORMATION: Reverse primer for RBP3

<400> SEQUENCE: 22
agcacaagat gggaatggag                                              20

<210> SEQ ID NO 23
<211> LENGTH: 21
<212> TYPE: DNA
<213> ORGANISM: Artificial Sequence
<220> FEATURE:
<223> OTHER INFORMATION: Forward primer for PDE6B

<400> SEQUENCE: 23
aggagaccct gaacatctac c                                            21

<210> SEQ ID NO 24
<211> LENGTH: 18
<212> TYPE: DNA
<213> ORGANISM: Artificial Sequence
<220> FEATURE:

<223> OTHER INFORMATION: Reverse primer for PDE6B

<400> SEQUENCE: 24
atgaagccca cttgcagc                                             18

<210> SEQ ID NO 25
<211> LENGTH: 20
<212> TYPE: DNA
<213> ORGANISM: Artificial Sequence
<220> FEATURE:
<223> OTHER INFORMATION: Forward primer for OPN1SW

<400> SEQUENCE: 25
ctgggcactg tagcaggtct                                           20

<210> SEQ ID NO 26
<211> LENGTH: 18
<212> TYPE: DNA
<213> ORGANISM: Artificial Sequence
<220> FEATURE:
<223> OTHER INFORMATION: Reverse primer for OPN1SW

<400> SEQUENCE: 26
tgcaggccct cagggatg                                             18

<210> SEQ ID NO 27
<211> LENGTH: 20
<212> TYPE: DNA
<213> ORGANISM: Artificial Sequence
<220> FEATURE:
<223> OTHER INFORMATION: Forward primer for ASCL1

<400> SEQUENCE: 27
catctccccc aactactcca                                           20

<210> SEQ ID NO 28
<211> LENGTH: 20
<212> TYPE: DNA
<213> ORGANISM: Artificial Sequence
<220> FEATURE:
<223> OTHER INFORMATION: Reverse primer for ASCL1

<400> SEQUENCE: 28
cttttgcaca caagctgcat                                           20

<210> SEQ ID NO 29
<211> LENGTH: 25
<212> TYPE: DNA
<213> ORGANISM: Artificial Sequence
<220> FEATURE:
<223> OTHER INFORMATION: Forward primer for NEUROD1

<400> SEQUENCE: 29
gccccagggt tatgagacta tcact                                     25

<210> SEQ ID NO 30
<211> LENGTH: 25
<212> TYPE: DNA
<213> ORGANISM: Artificial Sequence
<220> FEATURE:
<223> OTHER INFORMATION: Reverse primer for NEUROD1

<400> SEQUENCE: 30
ccgacagagc ccagatgtag ttctt                                     25

```
<210> SEQ ID NO 31
<211> LENGTH: 20
<212> TYPE: DNA
<213> ORGANISM: Artificial Sequence
<220> FEATURE:
<223> OTHER INFORMATION: Forward primer for ATHO7

<400> SEQUENCE: 31
tcgcatcatc agacctatgg                                               20

<210> SEQ ID NO 32
<211> LENGTH: 20
<212> TYPE: DNA
<213> ORGANISM: Artificial Sequence
<220> FEATURE:
<223> OTHER INFORMATION: Reverse primer for ATHO7

<400> SEQUENCE: 32
ccgaacagga caaactcaca                                               20

<210> SEQ ID NO 33
<211> LENGTH: 18
<212> TYPE: DNA
<213> ORGANISM: Artificial Sequence
<220> FEATURE:
<223> OTHER INFORMATION: Forward primer for POU4F2

<400> SEQUENCE: 33
caaccccacc gagcaata                                                 18

<210> SEQ ID NO 34
<211> LENGTH: 20
<212> TYPE: DNA
<213> ORGANISM: Artificial Sequence
<220> FEATURE:
<223> OTHER INFORMATION: Reverse primer for POU4F2

<400> SEQUENCE: 34
gtgcacggga tggtattcat                                               20

<210> SEQ ID NO 35
<211> LENGTH: 22
<212> TYPE: DNA
<213> ORGANISM: Artificial Sequence
<220> FEATURE:
<223> OTHER INFORMATION: Forward primer for ARX

<400> SEQUENCE: 35
tgaaacgcaa acagaggcgc ta                                            22

<210> SEQ ID NO 36
<211> LENGTH: 24
<212> TYPE: DNA
<213> ORGANISM: Artificial Sequence
<220> FEATURE:
<223> OTHER INFORMATION: Reverse primer for ARX

<400> SEQUENCE: 36
tgatgaaagc tgggtgtcgg aaca                                          24

<210> SEQ ID NO 37
<211> LENGTH: 21
<212> TYPE: DNA
<213> ORGANISM: Artificial Sequence
<220> FEATURE:
<223> OTHER INFORMATION: Forward primer for AFP
```

```
<400> SEQUENCE: 37
tttagctgac ctggctacca t                                              21

<210> SEQ ID NO 38
<211> LENGTH: 20
<212> TYPE: DNA
<213> ORGANISM: Artificial Sequence
<220> FEATURE:
<223> OTHER INFORMATION: Reverse primer for AFP

<400> SEQUENCE: 38
cagcttgtga caggttctgg                                                20

<210> SEQ ID NO 39
<211> LENGTH: 20
<212> TYPE: DNA
<213> ORGANISM: Artificial Sequence
<220> FEATURE:
<223> OTHER INFORMATION: Forward primer for T

<400> SEQUENCE: 39
ccgtctcctt cagcaaagtc                                                20

<210> SEQ ID NO 40
<211> LENGTH: 20
<212> TYPE: DNA
<213> ORGANISM: Artificial Sequence
<220> FEATURE:
<223> OTHER INFORMATION: Reverse primer for T

<400> SEQUENCE: 40
caattgtcat gggattgcag                                                20

<210> SEQ ID NO 41
<211> LENGTH: 20
<212> TYPE: DNA
<213> ORGANISM: Artificial Sequence
<220> FEATURE:
<223> OTHER INFORMATION: Forward primer for GAPDH

<400> SEQUENCE: 41
agccacatcg ctcagacacc                                                20

<210> SEQ ID NO 42
<211> LENGTH: 19
<212> TYPE: DNA
<213> ORGANISM: Artificial Sequence
<220> FEATURE:
<223> OTHER INFORMATION: Reverse primer for GAPDH

<400> SEQUENCE: 42
gtactcagcg ccagcatcg                                                 19

<210> SEQ ID NO 43
<211> LENGTH: 20
<212> TYPE: DNA
<213> ORGANISM: Artificial Sequence
<220> FEATURE:
<223> OTHER INFORMATION: Forward primer for SAG

<400> SEQUENCE: 43
aaaaagtgcc accaaacagc                                                20

<210> SEQ ID NO 44
<211> LENGTH: 22
```

```
<212> TYPE: DNA
<213> ORGANISM: Artificial Sequence
<220> FEATURE:
<223> OTHER INFORMATION: Reverse primer for SAG

<400> SEQUENCE: 44
acgtcattct tgtctctctt cc                                              22
```